(12) United States Patent
Su et al.

(10) Patent No.: US 8,222,297 B2
(45) Date of Patent: Jul. 17, 2012

(54) ANILINE OR PHENOL MUSTARDS LINKED TO DNA-AFFINIC MOLECULES OR WATER-SOLUBLE AROMATIC RINGS AND THEIR USE AS CANCER THERAPEUTIC AGENTS

(75) Inventors: Tsann-Long Su, Baldwin Place, NY (US); Ting-Chao Chou, Paramus, NJ (US)

(73) Assignee: Academia Sinica, Taipei (TW)

( * ) Notice: Subject to any disclaimer, the term of this patent is extended or adjusted under 35 U.S.C. 154(b) by 1223 days.

(21) Appl. No.: 12/008,512

(22) Filed: Jan. 11, 2008

(65) Prior Publication Data

US 2008/0171765 A1     Jul. 17, 2008

Related U.S. Application Data

(60) Provisional application No. 60/879,853, filed on Jan. 11, 2007.

(51) Int. Cl.
    *A61K 31/17*     (2006.01)
    *C07C 275/40*     (2006.01)

(52) U.S. Cl. .......................................... 514/597; 564/50

(58) Field of Classification Search .................... 564/50; 514/597

See application file for complete search history.

(56) References Cited

OTHER PUBLICATIONS

Ross et al, Journal of the Chemical Society (1955), 3110-16.*

\* cited by examiner

*Primary Examiner* — Rebecca Anderson
(74) *Attorney, Agent, or Firm* — VLP Law Group LLP

(57) ABSTRACT

New aniline or phenol N-mustards linked to DNA-affinity carriers (such as 9-anilinoacridines, acridines and quinolines), aminobenzamides or aminophenol ethers by a urea, carbamic acid, carbanic acid ester, hydrazineurea, hydrazinecarbamic acid ester, phenoxyurea, phenoxycarbamic acid ester linkage with improved chemical stability and anti-tumor therapeutic efficacy are provided.

4 Claims, 5 Drawing Sheets

4A

4B

ANILINE OR PHENOL MUSTARDS LINKED TO DNA-AFFINIC MOLECULES OR WATER-SOLUBLE AROMATIC RINGS AND THEIR USE AS CANCER THERAPEUTIC AGENTS

RELATED APPLICATIONS

This application claims priority from U.S. Provisional Patent Application Ser. No. 60/879,853 which was filed on Jan. 11, 2007. The content of U.S. Provisional Patent Application Ser. No. 60/879,853 is entirely incorporated herein by reference.

BACKGROUND OF THE INVENTION

1. Field of the Invention

The present application pertains to N-mustard compounds, methods for their preparation, pharmaceutical compositions comprising such compounds, and the use of such compounds and compositions in therapy and treatment, for example, of cancer.

2. Description of the Related Art

Gene-targeting agents, such as N-mustards, have played an important part in anticancer drug development.[1] Drawbacks of using DNA-alkylating agents include their high reactivity resulting in loss of therapeutic activity against malignancy by reacting with other cellular components such as proteins, thiols or genes,[2] lacking of intrinsic DNA binding affinity of the core N,N-bis(2-chloroethyl)amine pharmacophore and a requirement for bifunctional crosslinking of DNA to be fully cytotoxic resulting in lower their potency and producing high ratio of genotoxic monoadducts to crosslinkers (up 20:1).[3] It has demonstrated that the targeting mustards to DNA by attaching to DNA-affinic carriers facilitates in finding compounds of higher cytotoxicity and potency than the corresponding untargeted N-mustard moiety. There is renewed interest in these general class of drugs, following recent demonstrations that both their sequence and regioselectivity of DNA alkylation can be altered by attaching them to a variety of DNA-affinic carriers (such as DNA-intercalators or DNA minor groove binders) and that can result in a modified spectrum of biological activity.[4-14]

Among DNA-targeting mustards using 9-anilinoacridines as a DNA-affinic carrier, compound 1 and 2, were less cytotoxic than amsacrine (3) and the 4-linked analogues (1) showed slightly higher in vivo antileukemic activity than their corresponding 1'-linked analogues (2), indicating that the N-mustard residue would prefer to be linked to the acridone chromophore to have better cytotoxicity.[10] In contrast, our recent research on development of gene-targeting N-mustards demonstrated that alkyl N-mustard linked to the anilino ring or acridine chromophore of 9-anilinoacridines, such as (3-(acridin-9-ylamino)-5-{2-[bis-(2-chloroethyl)amino]-ethoxy}phenylmethanol (4, BO-0742)[15,16] and N1-(4-{2-[bis(2-chloroethyl)-amino]-ethoxy}acridin-9-yl)-5-methoxybenzene-1,3-diamine hydrochloride (5, BO-0940),[17] respectively, were significantly more cytotoxic (>100-time) than 3-(9-acridinyl-amino)-5-hydroxymethylaniline (AHMA, 6)[18,19] in inhibiting various human leukemia and solid tumor in vitro and in vivo. Formulae of the compounds discussed in this paragraph is shown in FIG. 1.

N-mustard derivatives, in general, have a short half-life in mice and human plasma. Our unpublished results showed that the half-life of BO-0742 in mice is about 25 min. To overcome the chemical instability of N-mustards, a number of aziridinylnitrobenzamides[20,21] (i.e., 7, CB 1954, Scheme 1) and 5-[N,N-bis(2-haloethyl)amino]-2,4-dinitrobenzamides (9)[20] or aniline and benzoic acid mustards linked to L-glutamic acid moiety through a urea or carbamic acid ester linkage (11, Scheme 2)[22] or carboxamide (13, CMDA)[22] have been synthesized as candidate prodrugs for gene-directed enzyme prodrug therapy (GDEPT).[23] The electro-withdrawing aromatic nitro function of the aziridinyinitrobenzamides can be reduced efficiently to the active electron-donating hydroxyamino by E. coli nitro-reductase (NR) (Scheme 1). The activation of the glutamic acid containing mustards requires carboxypeptidase G2 (CPG2). It has demonstrated that these prodrugs were effective substrates for the enzyme and showed to have improved therapeutic activity in CPG2-expressing xenografts.[24-32]

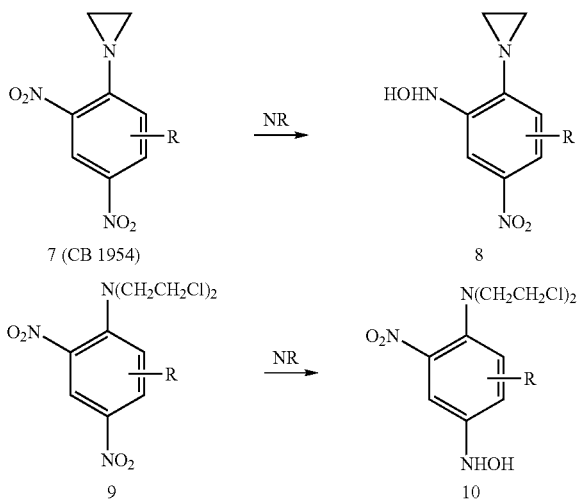

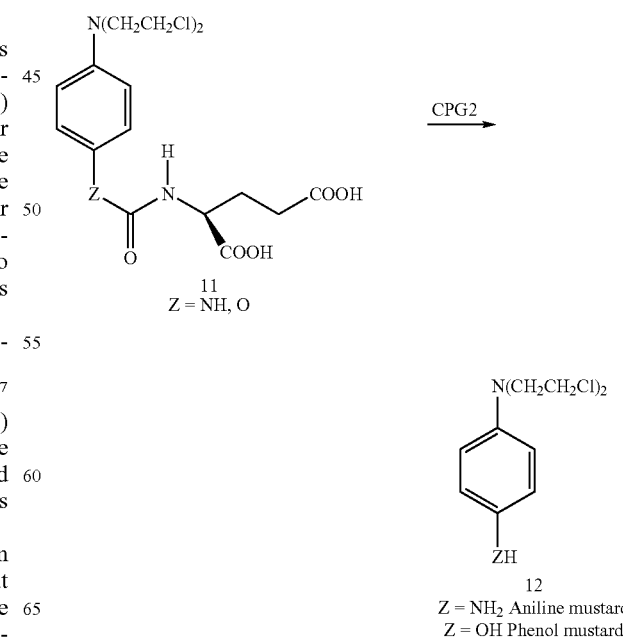

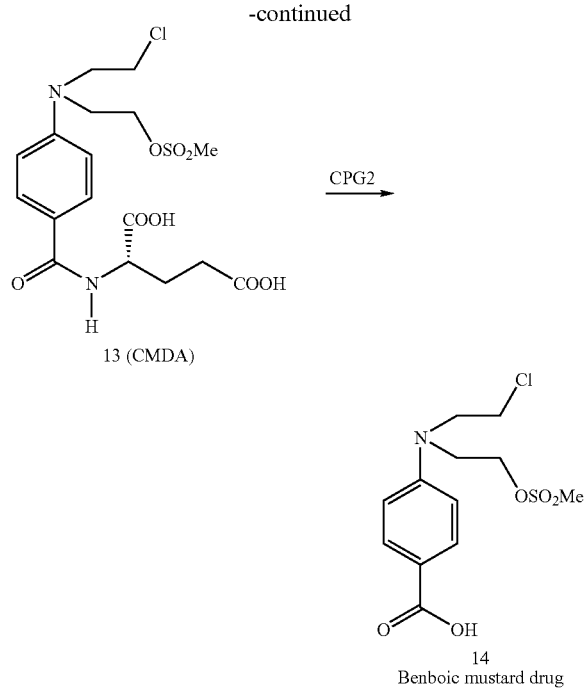

13 (CMDA)

14 Benboic mustard drug

Therefore, there is a need for a new potent DNA-targeting alkylating agents having a long half-life in human plasma.

SUMMARY OF THE INVENTION

One aspect of the present application pertains to a compound of the following formula

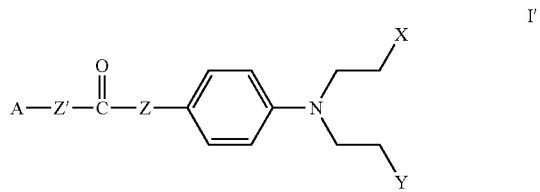

where X and Y are independently selected from the group consisting of Cl, Br, I, and $OSO_2Me$ X; Z is NH or O; Z' is NH, NHNH, O—Ar—NH or O; Ar is a substituted benzene; A is an aromatic residue selected from substituted or unsubstituted 9-anilinoacridines, acridines, qunilones, amino benzamides, and amino phenol ethers residues.

Another aspect of the present application pertains to a composition comprising a compound of Formula (I') as described above and a pharmaceutically acceptable carrier.

Yet another aspect of the present application pertains to use of the compound of formula (I') or pharmaceutically acceptable salt thereof in treating cancer, such as brain tumor, breast cancer, colon cancer, leukemia, and neuroblastoma.

Still another aspect of the present application pertains to process of making a compound of formula (I'), as illustrated below in detail.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
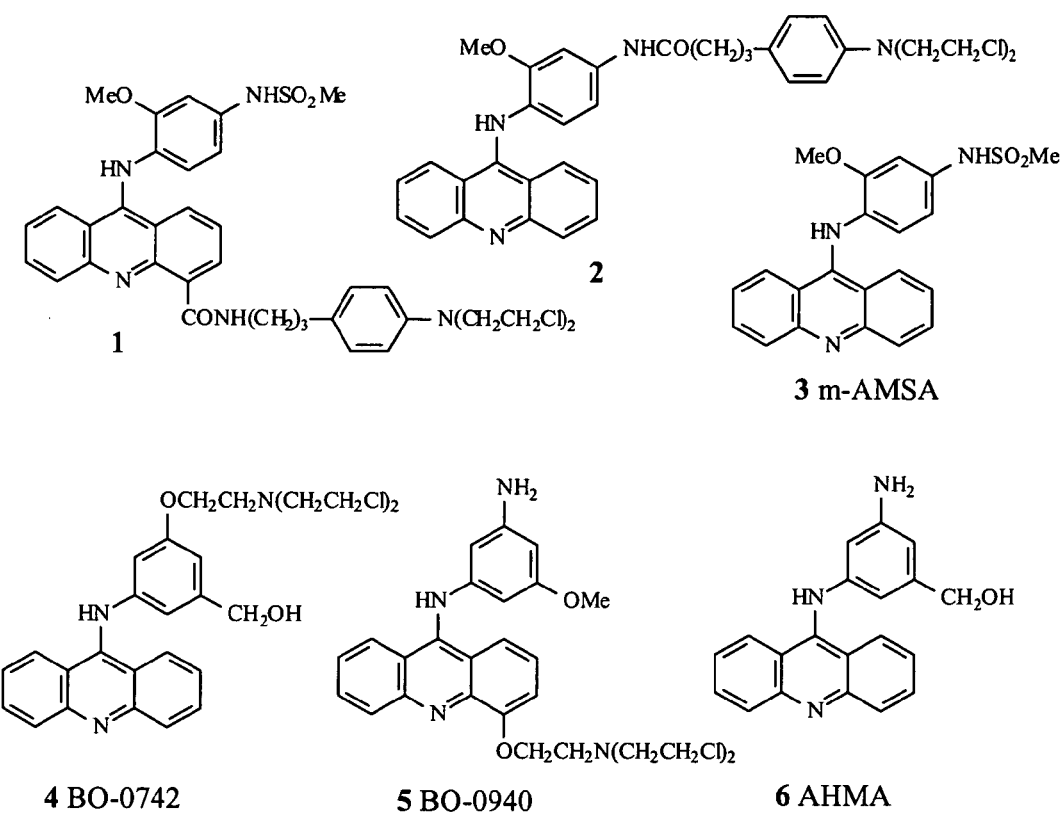
FIG. 1 shows the formulae of compounds 1-6 discussed above in Section "Description of the Related Art."

We have designed and synthesized aniline mustard or phenol mustard derivatives, in which the N-mustard pharmacophore is linked to a DNA-affinic carrier, such as 9-anilinoacridines (DNA intercalating agents, i.e., AHMA derivatives), acridines (DNA intercalating agents) or quinolines (DNA minor groove binder) through a urea, carbamic acid or carbonic acid ester, hydrazinecarboxamide, oxypneylurea, or oxyphenylcarbamic acid ester linkage. The reactivity of the aniline or phenol N-mustard can be reduced by these linkers to form more stable N-mustard derivatives. Therefore, the new compounds in accordance with the present application include:

9-Anilinoacridine-N-mustard conjugates (Formula I-Formula III shown below). Compounds belong to this class are: 1) AHMA-N-mustard conjugates (Formula I): the N-mustard residue is linked to the anilino ring of 9-anilinoacridines (i.e., AHMA or its derivatives) via a urea, carmabic acid ester, or carbonic acid ester linker (Formula I); 2) N-acyl-AHMA-N-mustard conjugates (Formula II): the N-mustard residue is linked to the hydroxymethyl function of N-acyl-AHMA; and (3) AHMA-alkylcarbamate-N-mustard conjugates (Formula III): the N-mustard residue is linked to the hydroxymethyl function of AHMA-alkylcarbamates. These 9-anilinoacridines were previously synthesized in our laboratory.[18,19,33,34]

Acridine-N-mustard conjugates (Formula IV shown below). The N-mustard residue is linked to the DNA-intercalating agents, 9-aminoacridines.

Quinoline-N-mustard conjugates (Formula V-VII). The N-mustard residue is linked to 4-aminoquinolines (DNA minor-groove binder) bearing urea (Formula V), hydrazinecarboxamide and hydrazinecarboxylic acid ester (Formula VII), oxyphenylurea and oxyphenylcarbamic acid ester (Formula VII) linkage.

Water-soluble benzamide- or phenol ether-N-mustard derivatives (Formula VIII and Formula IX). Compounds belong to this category are designed as water-soluble congeners of N-mustard. The reactive N-mustard residue is deactivated by the urea or carbamic acid ester function. While the hydrophilic side-chain on the benzamides or phenol ethers will increase the water-solubility of the conjugates.

The compounds of the present application include compounds of Formula I:

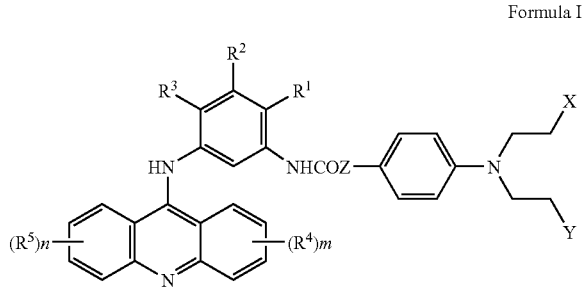

Formula I where Z is NH or O;
each of X and Y is, independently, Cl, Br, I, or $OSO_2Me$;
each of $R^1$, $R^2$ and $R^3$ is, independently, hydrogen, $C_1$-$C_6$ alkyl, $OR^a$ ($R^a$ is $C_1$-$C_3$ alkyl), or $CH_2OH$; and
each of $R^4$ and $R^5$ is, independently, hydrogen, $C_1$-$C_6$ alkyl, $OR^{a'}$, nitro, halo, $N(R^b)_2$, $NH(CH_2)_pN(R^b)_2$, $(CH_2)_qOH$, $(CH_2)_qX$, $CONHR^b$, $CONH(CH_2)_pN(R^b)_2$, $SO_3R^b$, or $SO_2R^b$ Each of m and n is, independently, 0-4, $R^{a'}$ is $C_1$-$C_{10}$ alkyl, $R^b$ is hydrogen or $C_1$-$C_{10}$ alkyl; p is 1-5; and q is 1-3.

Preferably, in Formula I, $R^2$ is $CH_2OH$, and $R^1$ and $R^3$ are hydrogen, respectively.

Also preferably, in Formula I, at least one of $R^1$, $R^2$ and $R^3$ is $C_1$-$C_4$ alkyl or $OR^a$ and at least one of $R^1$, $R^2$ and $R^3$ is hydrogen.

One or several of $R^1$, $R^2$ and $R^3$ can be $C_1$-$C_4$ alkyl. One or several of $R^1$, $R^2$ and $R^3$ and $OR^a$ can be e.g., $CH_3$ or $OCH_3$.

Each of $R^4$ and $R^5$ can be independently, hydrogen, $C_1$-$C_6$ alkyl, $OR^b$ or $CONHR^b$, or $CONH(CH_2)_pN(R^b)_2$ and each of m and n can be, independently, 1. $R^b$ can be $C_1$-$C_4$ alkyl, and p can be 2. $R^4$ and $R^5$ can occupy the C-4 and C-5 positions of the acridine ring, respectively. For example, $R^4$ can be $CONH(CH_2)_2N(CH_3)_2$ and $R^5$ can be $CH_3$.

The term "halo" refers to any radical of fluorine, chlorine, bromine and iodine.

The following are some examples of compounds of Formula I.

AHMA-Aniline Mustard Conjugates (urea linkage):
1-[3-(Acridin-9-ylamino)-5-hydroxymethylphenyl]-3-{4-[bis(2-chloroethyl)amino]-phenyl}urea;
1-{4-[Bis(2-chloroethyl)-amino]phenyl}-3-[3-hydroxymethyl-5-(4-methylacridin-9-ylamino)phenyl]urea;
1-{4-[Bis(2-chloroethyl)amino]-phenyl}-3-[3-hydroxymethyl-5-(4-methoxyacridin-9-ylamino)phenyl]urea;
9-[3-(3-{4-[Bis(2-chloroethyl)-amino]phenyl}ureido)-5-hydroxymethyl-phenylamino]-acridine-4-carboxylic acid methylamide;
9-[3-(3-{4-[Bis(2-chloroethyl)amino]phenyl}ureido)-5-hydroxymethylphenylamino]-acridine-4-carboxylic acid (2-dimethylaminoethyl)amide;
9-[3-(3-{4-[Bis(2-chloroethyl)amino]phenyl}ureido)-5-hydroxymethylphenylamino]-5-methyl-acridine-4-carboxylic acid methylamide;
9-[3-(3-{4-[Bis(2-chloroethyl)amino]phenyl}ureido)-5-hydroxymethylphenylamino]-5-methyl-acridine-4-carboxylic acid (2-dimethylaminoethyl)amide;
9-[3-(3-{4-[Bis(2-chloroethyl)amino]phenyl}ureido)-5-hydroxymethylphenylamino]-5-methoxyacridine-4-carboxylic acid methylamide; and
9-[3-(3-{4-[Bis(2-chloroethyl)amino]phenyl}ureido)-5-hydroxymethylphenylamino]-5-methoxyacridine-4-carboxylic acid (2-dimethylaminoethyl)amide;

3-(Acridin-9-ylamino)-m-toluidine (AMT)-Aniline Mustard Conjugates (urea linkage):
1-[3-(Acridin-9-ylamino)-5-methylphenyl]-3-{4-[bis(2-chloroethyl)-amino]phenyl}-urea;
1-{4-[Bis(2-chloroethyl)amino]phenyl}-3-[3-methyl-5-(4-methylacridin-9-ylamino)-phenyl]urea;
1-{4-[Bis(2-chloroethyl)amino]phenyl}-3-[3-(4-methoxyacridin-9-ylamino)-5-methylphenyl]urea;
9-[3-(3-{4-[Bis(2-chloroethyl)amino]phenyl}ureido)-5-methyl-phenylamino]acridine-4-carboxylic acid methylamide;
9-[3-(3-{4-[Bis(2-chloroethyl)amino]phenyl}ureido)-5-methylphenylamino]acridine-4-carboxylic acid (2-dimethylaminoethyl)amide;
9-[3-(3-{4-[Bis(2-chloroethyl)amino]phenyl}ureido)-5-methyl-phenylamino]-5-methylacridine-4-carboxylic acid methylamide;
9-[3-(3-{4-[Bis(2-chloroethyl)amino]phenyl}ureido)-5-methylphenylamino]-5-methylacridine-4-carboxylic acid (2-dimethylaminoethyl)amide;
9-[3-(3-{4-[Bis(2-chloroethyl)amino]phenyl}ureido)-5-methylphenylamino]-5-methoxyacridine-4-carboxylic acid methylamide; and
9-[3-(3-{4-[Bis(2-chloroethyl)amino]phenyl}ureido)-5-methyl-phenylamino]-5-methoxyacridine-4-carboxylic acid (2-dimethylaminoethyl)amide;

3-(Acridin-9-ylamino)-o-toluidine (AOT)-Aniline-Mustard Conjugates (urea linkage):
1-[5-(Acridin-9-ylamino)-2-methyl-phenyl]-3-{4-[bis(2-chloroethyl)amino]phenyl}-urea;
1-{4-[Bis(2-chloroethyl)amino]phenyl}-3-[2-methyl-5-(4-methylacridin-9-ylamino)-phenyl]urea;
1-{4-[Bis(2-chloroethyl)amino]phenyl}-3-[5-(4-methoxyacridin-9-ylamino)-2-methylphenyl]urea;
9-[3-(3-{4-[Bis(2-chloroethyl)amino]phenyl}ureido)-4-methylphenylamino]acridine-4-carboxylic acid methylamide;
9-[3-(3-{4-[Bis(2-chloroethyl)amino]phenyl}ureido)-4-methylphenylamino]acridine-4-carboxylic acid (2-dimethylaminoethyl)amide;
9-[3-(3-{4-[Bis(2-chloroethyl)amino]phenyl}ureido)-4-methylphenylamino]-5-methylacridine-4-carboxylic acid methylamide;
9-[3-(3-{4-[Bis(2-chloro-ethyl)amino]phenyl}ureido)-4-methyl-phenylamino]-5-methylacridine-4-carboxylic acid (2-dimethylaminoethyl)amide;
9-[3-(3-{4-[Bis(2-chloroethyl)amino]phenyl}ureido)-4-methylphenylamino]-5-methylacridine-4-carboxylic acid methylamide; and
9-[3-(3-{4-[Bis(2-chloroethyl)amino]phenyl}ureido)-4-methylphenylamino]-5-methoxyacridine-4-carboxylic acid (2-dimethylaminoethyl)amide;

3-(Acridin-9-ylamino)-p-toluidine (APT)-Aniline Mustard Conjugates (urea linkage):
1-[3-(Acridin-9-ylamino)-4-methylphenyl]-3-{4-[bis-2-chloroethyl]amino}phenyl}urea;
1-{4-[Bis(2-chloroethyl)amino]-phenyl}-3-[4-methyl-3-(4-methy-acridin-9-ylamino)-phenyl]urea;
1-{4-[Bis(2-chloroethyl)amino]phenyl}-3-[3-(4-methoxyacridin-9-ylamino)-4-methylphenyl]urea;
9-[5-(3-{4-[Bis(2-chloroethyl)amino]phenyl}ureido)-2-methylphenylamino]acridine-4-carboxylic acid methylamide;

9-[5-(3-{4-[Bis(2-chloroethyl)amino]phenyl}ureido)-2-methylphenylamino]acridine-4-carboxylic acid (2-dimethylaminoethyl-amide;

9-[5-(3-{4-[Bis(2-chloroethyl)amino]phenyl}ureido)-2-methylphenylamino]-5-methylacridine-4-carboxylic acid methylamide;

9-[5-(3-{4-[Bis(2-chloroethyl)amino]phenyl}ureido)-2-methylphenylamino]-5-methylacridine-4-carboxylic acid (2-dimethylaminoethyl)amide;

9-[5-(3-{4-[Bis(2-chloroethyl)amino]phenyl}ureido)-2-methylphenylamino]-5-methoxyacridine-4-carboxylic acid methylamide; and 9-[5-(3-{4-[Bis(2-chloroethyl)amino]phenyl}ureido)-2-methylphenylamino]-5-methoxyacridine-4-carboxylic acid (2-dimethylaminoethyl)amide;

3-(Acridinylamino)-m-anisidine (AMA)-Aniline Mustard Conjugates (urea linkage):

1-[3-(Acridin-9-ylamino)-5-methoxyphenyl]-3-{4-[bis(2-chloroethyl)-amino]phenyl}-urea;

1-{4-[Bis(2-chloroethyl)-amino]phenyl}-3-[3-methoxy-5-(4-methyl-acridin-9-ylamin)-phenyl]-urea;

1-{4-[Bis(2-chloroethyl)amino]phenyl}-3-[3-methoxy-5-(4-methoxyacridin-9-ylamino)phenyl]-urea;

9-[3-(3-{4-[Bis-2-chloroethyl]amino}phenyl)ureido]-5-methoxyphenylamino]-acridine-4-carboxylic acid methylamide;

9-[3-(3-{4-[Bis-2-chloroethyl]amino}phenyl)ureido]-5-methoxyphenylamino]-acridine-4-carboxylic acid (2-dimethylaminoethyl)amide;

9-[3-(3-{4-[Bis(2-chloroethyl)amino]phenyl}ureido)-5-methoxyphenylamino]-5-methylacridine-4-carboxylic acid methylamide;

9-[3-(3-{4-[Bis(2-chloroethyl)amino]phenyl}ureido)-5-methoxyphenylamino]-5-methylacridine-4-carboxylic acid (2-dimethylamino-ethyl)amide;

9-[3-(3-{4-[Bis(2-chloroethyl)amino]phenyl}ureido)-5-methoxyphenylamino]-5-methoxyacridine-4-carboxylic acid methylamide; and 9-[3-(3-{-[Bis(2-chloroethyl)amino]phenyl}ureido)-5-methoxyphenylamino]-5-methoxyacridine-4-carboxylic acid (2-dimethylaminoethyl)amide;

3-(Acridinylamino)-o-anisidine (AOA)-Aniline Mustard Conjugates (urea linkage):

1-[5-(Acridin-9-ylamino)-2-methoxyphenyl]-3-{4-[bis(2-chloroethyl)-amino]-phenyl}urea;

1-{4-[Bis(2-chloroethyl)amino]phenyl}-3-[2-methoxy-5-(4-methylacridin-9-ylamino)phenyl]urea;

1-{4-[Bis(2-chloroethyl)amino]phenyl}-3-[2-methoxy-5-(4-methoxy-acridin-9-ylamino)phenyl]urea;

9-[3-(3-{4-[Bis(2-chloroethyl)amino]phenyl}ureido)-4-methoxyphenylamino]-acridine-4-carboxylic acid (2-dimethylaminoethyl)amide;

9-[3-(3-{4-[Bis(2-chloroethyl)amino]phenyl}ureido)-4-methoxy-phenylamino]-5-methylacridine-4-carboxylic acid methylamide;

9-[3-(3-{4-[Bis(2-chloroethyl)amino]phenyl}ureido)-4-methoxyphenylamino]-5-methyl-acridine-4-carboxylic acid (2-dimethylaminoethyl)amide;

9-[3-(3-{4-[Bis(2-chloroethyl)amino]phenyl}ureido)-4-methoxy-phenylamino]-5-methoxyacridine-4-carboxylic acid methylamide; and 9-[3-(3-{4-[Bis(2-chloroethyl)amino]phenyl}ureido)-4-methoxyphenylamino]-5-methoxyacridine-4-carboxylic acid (2-dimethylaminoethyl)amide;

3-(Acridinylamino)-p-anisidine (APA)-Aniline Mustard Conjugates (urea linkage):

1-[3-(Acridin-9-ylamino)-4-methoxyphenyl]-3-{4-[bis(2-chloroethyl)amino]phenyl}-urea;

1-{4-[Bis(2-chloroethyl)amino]phenyl}-3-[4-methyl-3-(4-methylacridin-9-ylamino)-phenyl]urea;

1-{4-[Bis(2-chloroethyl)amino]phenyl}-3-[3-(4-methoxyacridin-9-ylamino)-4-methylphenyl]urea;

9-[5-(3-{4-[Bis(2-chloroethyl)amino]phenyl}ureido)-2-methoxyphenylamino]-acridine-4-carboxylic acid (2-dimethylaminoethyl)-mide;

9-[5-(3-{4-[Bis(2-chloroethyl)amino]phenyl}ureido)-2-methoxyphenylamino]-5-methylacridine-4-carboxylic acid methylamide;

9-[5-(3-{4-[Bis(2-chloroethyl)amino]phenyl}ureido)-2-methoxyphenylamino]-5-methylacridine-4-carboxylic acid (2-dimethylaminoethyl)amide;

9-[5-(3-{4-[Bis(2-chloroethyl)amino]phenyl}ureido)-2-methoxyphenylamino]-5-methoxyacridine-4-carboxylic acid methylamide; and 9-[5-(3-{4-[Bis(2-chloroethyl)amino]phenyl}ureido)-2-methoxyphenylamino]-5-methoxyacridine-4-carboxylic acid (2-dimethylamino-ethyl)amide;

AHMA-Phenol Mustard Conjugates (carbamic acid ester linkage):

[3-(Acridin-9-ylamino)-5-hydroxymethylphenyl]carbamic acid 4-[bis(2-chloroethyl)-amino]phenyl ester;

[3-Hydroxymethyl-5-(4-methylacridin-9-ylamino)phenyl]carbamic acid 4-[bis(2-chloroethyl)amino]phenyl ester;

[3-Hydroxymethyl-5-(4-methoxyacridin-9-ylamino)phenyl]carbamic acid 4-[bis-(2-chloroethyl)amino]phenyl ester;

[3-Hydroxymethyl-5-(4-methylcarbamoyl-acridin-9-ylamino)phenyl]carbamic acid 4-[bis-(2-chloroethyl)amino]phenyl ester;

{3-[4-(2-Dimethylaminoethylcarbamoyl)acridin-9-ylamino]-5-hydroxymethylphenyl}carbamic acid 4-[bis(2-chloroethyl)amino]phenyl ester;

[3-Hydroxymethyl-5-(4-methyl-5-methylcarbamoyl-acridin-9-ylamino)phenyl]carbaic acid 4-[bis(2-chloroethyl)amino]phenyl ester;

{3-[4-(2-Dimethylaminoethylcarbamoyl)-5-methylacridin-9-ylamino]-5-hydroxy-methylphenyl}carbamic acid 4-[bis(2-chloroethyl)amino]phenyl ester;

[3-Hydroxymethyl-5-(4-methoxy-5-methylcarbamoyl-acridin-9-ylamino)phenyl]-carbamic acid 4-[bis(2-chloroethyl)amino]phenyl ester; and {3-[4-(2-Dimethylaminoethylcarbamoyl)-5-methoxyacridin-9-ylamino]-5-hydroxymethylphenyl}carbamic acid 4-[bis(2-chloroethyl)amino]phenyl ester;

3-(Acridin-9-ylamino)-m-toluidine (AMT)-Phenol Mustard Conjugates (carbamic acid ester linkage):

3-(Acridin-9-ylamino)-5-methylphenyl]carbamic acid 4-[bis(2-chloroethyl)amino]-phenyl ester;

[3-Methyl-5-(4-methylacridin-9-ylamino)phenyl]carbamic acid 4-[bis(2-chloroethyl)-amino]phenyl ester;

[3-(4-Methoxyacridin-9-ylamino)-5-methylphenyl]carbamic acid 4-[bis(2-chloroethyl)-amino]phenyl ester;

[3-Methyl-5-(4-methylcarbamoyl-acridin-9-ylamino)phenyl]-arbamic acid 4-[bis(2-chloroethyl)-amino]phenyl ester;

{3-[4-(2-Dimethylaminoethylcarbamoyl)acridin-9-ylamino]-5-methylphenyl}-carbamic acid 4-[bis(2-chloroethyl)amino]phenyl ester;

[3-Methyl-5-(4-methyl-5-methylcarbamoylacridin-9-ylamino)phenyl]-carbamic acid 4-[bis(2-chloroethyl)amino]phenyl ester;

{3-[4-(2-Dimethylaminoethylcarbamoyl)-5-methylacridin-9-ylamino]-5-methyl-phenyl}carbamic acid 4-[bis(2-chloroethyl)amino]phenyl ester;

[3-(4-Methoxy-5-methylcarbamoylacridin-9-ylamino)-5-methylphenyl]carbamic acid 4-[bis(2-chloroethyl)amino] phenyl ester; and {3-[4-(2-Dimethylaminoethylcarbamoyl)-5-methoxyacridin-9-ylamino]-5-methylphenyl}carbamic acid 4-[bis(2-chloroethyl)amino]phenyl ester;

3-(Acridin-9-ylamino)-o-toluidine (AOT)-Phenol-Mustard Conjugates (carbamic acid ester linkage):

[5-(Acridin-9-ylamino)-2-methylphenyl]carbamic acid 4-[bis(2-chloroethyl)-amino]phenyl ester;

[2-Methyl-5-(4-methylacridin-9-ylamino)phenyl]carbamic acid 4-[bis(2-chloroethyl)amino]phenyl ester;

[5-(4-Methoxyacridin-9-ylamino)-2-methylphenyl]carbamic acid 4-[bis(2-chloroethyl)amino]phenyl ester;

[2-Methyl-5-(4-methylcarbamoyl-acridin-9-ylamino)phenyl]carbamic acid 4-[bis(2-chloroethyl)amino]phenyl ester;

{5-[4-(2-Dimethylaminoethylcarbamoyl)acridin-9-ylamino]-2-methylphenyl}-carbamic acid 4-[bis(2-chloroethyl)amino]phenyl ester;

[2-Methyl-5-(4-methyl-5-methylcarbamoyl-acridin-9-ylamino)phenyl]-carbamic acid 4-[bis(2-chloroethyl) amino]phenyl ester;

{5-[4-(2-Dimethylaminoethylcarbamoyl)-5-methylacridin-9-ylamino]-2-methyl-phenyl}carbamic acid 4-[bis(2-chloroethyl)amino]phenyl ester;

[2-Methyl-5-(4-methyl-5-methylcarbamoyl-acridin-9-ylamino)phenyl]carbamic acid 4-[bis(2-chloroethyl) amino]phenyl ester; and {5-[4-(2-Dimethylaminoethylcarbamoyl)-5-methoxyacridin-9-ylamino]-2-methyl-phenyl}carbamic acid 4-[bis(2-chloroethyl)amino]phenyl ester;

3-(Acridin-9-ylamino)-p-toluidine (APT)-Phenol Mustard Conjugates (carbamoic acid ester linkage):

[3-(Acridin-9-ylamino)-4-methylphenyl]carbamic acid 4-[bis(2-chloroethyl)-amino]-phenyl ester;

[3-(4-Methoxyacridin-9-ylamino)-4-methylphenyl]carbamic acid 4-[bis(2-chloroethyl)amino]phenyl ester;

[4-Methyl-3-(4-methyl-acridin-9-ylamino)phenyl]carbamic acid 4-[bis(2-chloroethyl)amino]phenyl ester;

[4-Methyl-3-(4-methylcarbamoyl-acridin-9-ylamino)phenyl]carbamic acid 4-[bis(2-chloroethyl)amino]-phenyl ester;

{3-[4-(2-Dimethylaminoethylcarbamoyl)-acridin-9-ylamino]-4-methylphenyl}-carbamic acid 4-[bis(2-chloroethyl)amino]phenyl ester;

[4-Methyl-3-(4-methyl-5-methylcarbamoyl-acridin-9-ylamino)phenyl]carbamic acid 4-[bis(2-chloroethyl) amino]phenyl ester;

{3-[4-(2-Dimethylaminoethylcarbamoyl)-5-methylacridin-9-ylamino]-4-methyl-phenyl}carbamic acid 4-[bis(2-chloroethyl)amino]phenyl ester;

[3-(4-Methoxy-5-methylcarbamoyl-acridin-9-ylamino)-4-methylphenyl]carbamic acid 4-[bis(2-chloroethyl)-amino] phenyl ester; and {3-[4-(2-Dimethylaminoethylcarbamoyl)-5-methoxyacridin-9-ylamino]-4-methyl-phenyl}carbamic acid 4-[bis(2-chloroethyl)amino]phenyl ester;

3-(Acridinylamino)-m-anisidine (AMA)-Phenol Mustard Conjugates (carbamic acid ester linkage):

[3-(Acridin-9-ylamino)-5-methoxyphenyl]carbamic acid 4-[bis (2-chloroethyl)-amino]phenyl ester;

[3-Methoxy-5-(4-methylacridin-9-ylamino)-phenyl]carbamic acid 4-[bis(2-chloroethyl)amino]phenyl ester;

[3-Methoxy-5-(4-methoxyacridin-9-ylamino)phenyl]carbamic acid 4-[bis-(2-chloroethyl)amino]phenyl ester;

[3-Methoxy-5-(4-methylcarbamoyl-acridin-9-ylamino)phenyl]carbamic acid 4-[bis(2-chloroethyl)-amino]phenyl ester;

{3-[4-(2-Dimethylaminoethylcarbamoyl)acridin-9-ylamino]-5-methoxyphenyl}-carbamic acid 4-[bis(2-chloroethyl)amino]phenyl ester;

[3-Methoxy-5-(4-methyl-5-methylcarbamoyl-acridin-9-ylamino)phenyl]carbamic acid 4-[bis(2-chloroethyl)-amino]-phenyl ester;

{3-[4-(2-Dimethylaminoethylcarbamoyl)-5-methylacridin-9-ylamino]-5-methoxy-phenyl}carbamic acid 4-[bis(2-chloroethyl)amino]phenyl ester;

9-[3-(3-{4-[Bis(2-chloroethyl)amino]phenyl}ureido)-5-methoxyphenylamino]-5-methoxyacridine-4-carboxylic acid methylamide; and {3-[4-(2-Dimethylaminoethylcarbamoyl)-5-methoxyacridin-9-ylamino]-5-methoxy-phenyl}carbamic acid 4-[bis(2-chloroethyl)amino]phenyl ester;

3-(Acridinylamino)-o-anisidine (AOA)-Phenol Mustard Conjugates (carbamic acid ester linkage):

[5-(Acridin-9-ylamino)-2-methoxy-phenyl]arbamic acid 4-[bis(2-chloroethyl)-amino]phenyl ester;

[2-Methoxy-5-(4-methylacridin-9-ylamino)phenyl]carbamic acid 4-[bis(2-chloroethyl)amino]phenyl ester;

[2-Methoxy-5-(4-methoxyacridin-9-ylamino)phenyl]carbamic acid 4-[bis(2-chloroethyl)amino]phenyl ester;

{5-[4-(2-Dimethylaminoethylcarbamoyl)-acridin-9-ylamino]-2-methoxyphenyl}-carbamic acid 4-[bis(2-chloroethyl)amino]phenyl ester;

[2-Methoxy-5-(4-methyl-5-methylcarbamoyl-acridin-9-ylamino)phenyl]-carbamic acid 4-[bis(2-chloroethyl) amino]phenyl ester;

{5-[4-(2-Dimethylaminoethylcarbamoyl)-5-methylacridin-9-ylamino]-2-methoxy-phenyl}carbamic acid 4-[bis(2-chloroethyl)amino]phenyl ester;

[2-Methoxy-5-(4-methoxy-5-methylcarbamoyl-acridin-9-ylamino)phenyl]-carbamic acid 4-[bis(2-chloroethyl) amino]phenyl ester; and {5-[4-(2-Dimethylaminoethylcarbamoyl)-5-methoxy-acridin-9-ylamino]-2-methoxy-phenyl}carbamic acid 4-[bis(2-chloroethyl)amino]phenyl ester;

3-(Acridinylamino)-p-anisidine (APA)-Phenol Mustard (carbamic acid ester linkage):

[3-(Acridin-9-ylamino)-4-methoxyphenyl]carbamic acid 4-[bis(2-chloroethyl-amino)-phenyl ester;

[4-Methyl-3-(4-methyl-acridin-9-ylamino)phenyl]carbamic acid 4-[bis(2-chlorethyl)-amino]phenyl ester;

[3-(4-Methoxyacridin-9-ylamino)-4-methylphenyl]carbamic acid 4-[bis(2-chloroethyl)amino]phenyl ester;

{3-[4-(2-Dimethylaminoethylcarbamoyl)acridin-9-ylamino]-4-methoxy-phenyl}-carbamic acid 4-[bis(2-chloroethyl)amino]phenyl ester;

[4-Methoxy-3-(4-methyl-5-methylcarbamoyl-acridin-9-ylamino)phenyl]-carbamic acid 4-[bis(2-chloroethyl) amino]phenyl ester;

{3-[4-(2-Dimethylaminoethylcarbamoyl)-5-methylacridin-9-ylamino]-4-methoxyphenyl}carbamic acid 4-[bis(2-chloroethyl)amino]phenyl ester;

[4-Methoxy-3-(4-methoxy-5-methylcarbamoyl-acridin-9-ylamino)phenyl]-carbamic acid 4-[bis (2-chloroethyl) amino]phenyl ester; and {3-[4-(2-Dimethylaminoethylcarbamoyl)-5-methoxyacridin-9-ylamino]-4-methoxy-phenyl}carbamic acid 4-[bis(2-chloroethyl)amino]phenyl ester;

The compounds of the present application also include compounds of Formula II:

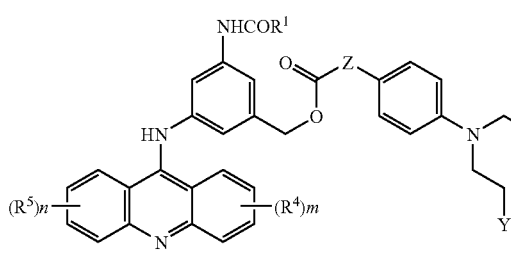

Formula II wherein Z is NH or O;
each X and Y is, independently, Cl, Br, I, or $OSO_2Me$;
$R^1$ is hydrogen or $C_1$-$C_6$ alkyl;
each of $R^4$ and $R^5$ is, independently, hydrogen, $C_1$-$C_6$ alkyl, $OR^a$, nitro, halo, $N(R^b)_2$, $NH(CH_2)_pN(R^b)_2$, $(CH_2)_qOH$, $(CH_2)qX$, $CONHR^b$, $CONH(CH_2)_pN(R^b)_2$, $SO_3R^b$, or $SO_2R^b$; each of m and n is, independently, 0-4, $R^a$ is $C_1$-$C_{10}$ alkyl, $R^b$ is hydrogen or $C_1$-$C_{10}$ alkyl; p is 1-5; and q is 1-3.

As a preferred embodiment, each of $R^4$ and $R^5$ can be independently, hydrogen, $C_1$-$C_6$ alkyl, $OR^a$, $CONHR^b$, or $CONH(CH_2)_pN(R^b)_2$ and each of m and n can be, independently, 1. $R^b$ can be $C_1$-$C_4$ alkyl, and p can be 2. $R^4$ and $R^5$ can occupy the C-4 and C-5 positions of the acridine ring, respectively. For example, $R^4$ can be $CONH(CH_2)_2N(CH_3)_2$ and $R^5$ can be $CH_3$.

The term "halo" refers to any radical of fluorine, chlorine, bromine and iodine.

The following are some representative compounds of Formula II:

N-Acyl-AHMA-Aniline Mustard Conjugates (carbamic acid ester linkage):
{4-[Bis(2-chloroethyl)amino]phenyl}carbamic acid 3-acetylamino-5-(acridin-9-ylamino)-benzyl ester;
{4-[Bis(2-chloroethyl)amino]phenyl}carbamic acid 3-(acridin-9-ylamino)-5-propionylamino-benzyl ester; and
{4-[Bis(2-chloroethyl)amino]phenyl}carbamic acid 3-(acridin-9-ylamino)-5-butyrylamino-benzyl ester.

N-Acyl-AHMA-Phenol Mustard Conjugates (carbonic acid ester linkage):
Carbonic acid 3-acetylamino-5-(acridin-9-ylamino)benzyl ester 4-[bis(2-chloroethyl)-amino]phenyl ester;
Carbonic acid 3-(acridin-9-ylamino)-5-propionylaminobenzyl ester 4-[bis(2-chloroethyl)amino]phenyl ester; and
Carbonic acid 3-(acridin-9-ylamino)-5-propionylaminobenzyl ester 4-[bis(2-chloroethyl)amino]phenyl ester.

The compounds in accordance with the present invention also include compounds of Formula III:

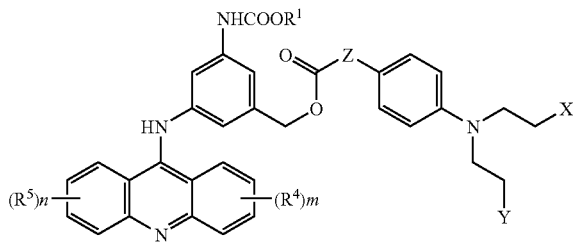

Formula III wherein Z is NH or O;
each X and Y is, independently, Cl, Br, I, or $OSO_2Me$;
$R^1$ is hydrogen or $C_1$-$C_6$ alkyl;
each of $R^4$ and $R^5$ is, independently, hydrogen, $C_1$-$C_6$ alkyl, $OR^a$, nitro, halo, $N(R^b)_2$, $NH(CH_2)_pN(R^b)_2$, $(CH_2)_qOH$, $(CH_2)qX$, $CONHR^b$, $CONH(CH_2)_pN(R^b)_2$, $SO_3R^b$, or $SO_2R^b$ each of m and n is, independently, 0-4, $R^a$ is $C_1$-$C_{10}$ alkyl, $R^b$ is hydrogen or $C_1$-$C_{10}$ alkyl; p is 1-5; and q is 1-3;

As preferred embodiments, each of $R^4$ and $R^5$ can be, independently, hydrogen, $C_1$-$C_6$ alkyl, $OR^a$ or $CONHR^b$, or $CONH(CH_2)_pN(R^b)_2$ and each of m and n can be, independently, 1. $R^b$ can be $C_1$-$C_4$ alkyl, and p can be 2. $R^4$ and $R^5$ can occupy the C-4 and C-5 positions of the acridine ring, respectively. For example, $R^4$ can be $CONH(CH_2)_2N(CH_3)_2$ and $R^5$ can be $CH_3$.

The term "halo" refers to any radical of fluorine, chlorine, bromine and iodine.

The following are some representative compounds of Formula III:

AHMA-alkylcarbamate-Aniline Mustard Conjugates (carbamic acid ester linkage)
(3-(Acridin-9-ylamino)-5-{4-[bis(2-chloroethyl)amino]phenylcarbamoyloxymethyl}-phenyl)carbamic acid methyl ester;
(3-(Acridin-9-ylamino)-5-{4-[bis(2-chloroethyl)amino]phenylcarbamoyloxymethyl}-phenyl)carbamic acid ethyl ester;
(3-(Acridin-9-ylamino)-5-{4-[bis(2-chloroethyl)amino]phenylcarbamoyloxymethyl}-phenyl)carbamic acid propyl ester;
(3-(Acridin-9-ylamino)-5-{4-[bis(2-chloroethyl)amino]phenylcarbamoyloxymethyl}-phenyl)carbamic acid isopropyl ester (3-(Acridin-9-ylamino)-5-{4-[bis(2-chloroethyl)amino]phenylcarbamoyloxymethyl}-phenyl)carbamic acid butyl ester;
(3-(Acridin-9-ylamino)-5-{4-[bis(2-chloroethyl)amino]phenylcarbamoyloxymethyl}-phenyl)carbamic acid isobutyl ester;
(3-(Acridin-9-ylamino)-5-{4-[bis(2-chloroethyl)-amino] phenylcarbamoyloxymethyl}-phenyl)carbamic acid tert-butyl ester;
[3-{4-[Bis(2-chloroethyl)amino]phenylcarbamoyloxymethyl}-5-(4-methyl-acridin-9-ylamino)phenyl]carbamic acid ethyl ester; and
{3-{4-[Bis(2-chloroethyl)amino]phenylcarbamoyloxymethyl}-5-[4-(2-dimethyl-aminoethylcarbamoyl)-5-methyl-acridin-9-ylamino]phenyl}carbamic acid ethyl ester.

AHMA-alkylcarbamate-Phenol Mustard Conjugates (carbonic acid ester linkage)
Carbonic acid 3-(acridin-9-ylamino)-5-methoxycarbonylaminobenzyl ester 4-[bis-(2-chloroethyl)amino]phenyl ester;
Carbonic acid 3-(acridin-9-ylamino)-5-ethoxycarbonylaminobenzyl ester 4-[bis(2-chloroethyl)amino]phenyl ester;
Carbonic acid 3-(acridin-9-ylamino)-5-propoxycarbonylaminobenzyl ester 4-[bis-2-chloro-thyl]amino]phenyl ester;
Carbonic acid 3-(acridin-9-ylamino)-5-isopropoxycarbonylaminobenzyl ester 4-[bis(2-chloroethyl)amino]phenyl ester;
Carbonic acid 3-(acridin-9-ylamino)-5-butoxycarbonylaminobenzyl ester 4-[bis(2-chloroethyl)amino]phenyl ester;
Carbonic acid 3-(acridin-9-ylamino)-5-isobutoxycarbonylaminobenzyl ester 4-[bis(2-chloroethyl)amino]phenyl ester;
Carbonic acid 3-(acridin-9-ylamino)-5-tert-butoxycarbonylaminobenzyl ester 4-[bis(2-chloroethyl)amino]phenyl ester;

Carbonic acid 4-[bis(2-chloro-ethyl)amino]phenyl ester 3-ethoxycarbonylamino-5-(4-methyl-acridin-9-ylamino) benzyl ester;

Carbonic acid 4-[bis(2-chloroethyl)amino]phenyl ester 3-[4-(2-dimethylamino-ethylcarbamoyl)-5-methyl-acridin-9-ylamino]-5-ethoxycarbonylamino-benzyl ester.

The compounds of the present application also include compounds of Formula IV:

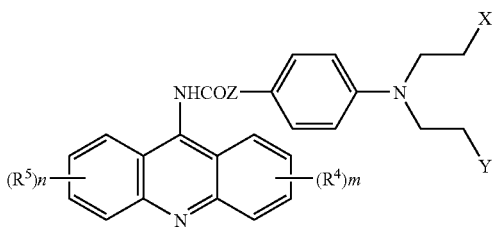

Formula IV wherein Z is NH or O;
each X of Y is, independently, Cl, Br, I, or $OSO_2Me$;
each of $R^4$ and $R^5$ is, independently, hydrogen, $C_1$-$C_6$ alkyl, $OR^a$, nitro, halo, $N(R^b)_2$, $NH(CH_2)_pN(R^b)_2$, $(CH_2)_qOH$, $(CH_2)qX$, $CONHR^b$, $CONH(CH_2)_pN(R^b)_2$, $SO_3R^b$, or $SO_2R^b$ Each m and n, is dependently, 0-4, $R^a$ is $C_1$-$C_{10}$ alkyl, $R^b$ is hydrogen or $C_1$-$C_{10}$ alkyl; p is 1-5; q is 1-3.

As preferred embodiments, each of $R^4$ and $R^5$ can be independently, hydrogen, $C_1$-$C_6$ alkyl, $OR^a$, $CONHR^b$, or $CONH(CH_2)_pN(R^b)_2$ and each of m and n can be, independently, 1. $R^b$ can be $C_1$-$C_4$ alkyl, and p can be 2. $R^4$ and $R^5$ can occupy the C-4 and C-5 positions of the acridine ring, respectively. For example, $R^4$ can be $CONH(CH_2)_2N(CH_3)_2$ and $R^5$ can be $CH_3$.

The representative compounds of Formula IV include:
Acridine-Aniline Mustard Conjugates (urea linkage):
1-Acridin-9-yl-3-{4-[bis(2-chloroethyl)amino]phenyl}urea;
1-{4-[Bis(2-chloroethyl)amino]phenyl}-3-(4-methylacridin-9-yl)urea;
1-{4-[Bis(2-chloroethyl)amino]phenyl}-3-(4-methoxyacridin-9-yl)urea;
9-(3-{4-[Bis(2-chloroethyl)amino]phenyl}ureido)acridine-4-carboxylic acid methylamide;
9-(3-{4-[Bis(2-chloroethyl)amino]phenyl}ureido)acridine-4-carboxylic acid (2-dimethylaminoethyl)amide;
9-(3-{4-[Bis(2-chloroethyl)amino]phenyl}ureido)-5-methylacridine-4-carboxylic acid methylamide;
9-(3-{4[Bis(2-chloroethyl)amino]phenyl}ureido)-5-methylacridine-4-carboxylic acid (2-dimethylaminoethyl) amide;
9-(3-{4-[Bis(2-chloroethyl)amino]phenyl}ureido)-5-methox-cridine-4-carboxylic acid methylamide; and
9-(3-{4-[Bis(2-chloroethyl)amino]phenyl}ureido)-5-methoxyacridine-4-carboxylic acid (2-dimethylaminoethyl) amide;
Acridine-Phenol Mustard Conjugates (carbamic acid ester linkage):
Acridin-9-yl-carbamic acid 4-[bis(2-chloroethyl-amino]phenyl ester;
(4-Methyl-acridin-9-yl)-carbamic acid 4-[bis(2-chloroethyl)amino]phenyl ester;
(4-Methoxyacridin-9-yl)carbamic acid 4-[bis(2-chloroethyl)-amino]phenyl ester;
(4-Methylcarbamoyl-acridin-9-yl)carbamic acid 4-[bis(2-chloroethyl)amino]phenyl ester;
[4-(2-Dimethylaminoethylcarbamoyl)acridin-9-yl]carbamic acid 4-[bis(2-chloro-ethyl)amino-phenyl ester;
(4-Methyl-5-methylcarbamoyl-acridin-9-yl)carbamic acid 4-[bis(2-chloroethyl)-amino]phenyl ester;
[4-(2-Dimethylaminoethylcarbamoyl)-5-methylacridin-9-yl]carbamic acid 4-[bis(2-chloroethyl)amino]phenyl ester;
(4-Methoxy-5-methylcarbamoyl-acridin-9-yl)carbamic acid 4-[bis(2-chloroethyl)-amino]phenyl ester;
[4-(2-Dimethylaminoethylcarbamoyl)-5-methoxyacridin-9-yl]carbamic acid 4-[bis(2-chloroethyl)-amino]phenyl ester.

The compounds of the present application also include compounds of Formula V:

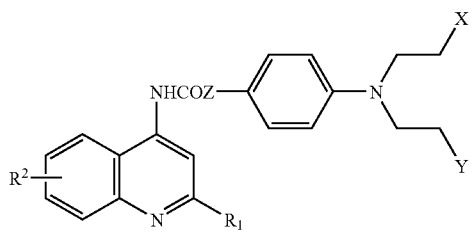

Formula V wherein Z is NH or O;
each of X and Y is, independently, Cl, Br, I, or $OSO_2Me$;
each of $R^1$ and $R^2$ is, independently, hydrogen, $C_1$-$C_6$ alkyl, alkyloxy, or aryl.

The term "aryl" refers both hydrocarbon aryl moieties and hetroaryl moietys. Examples of hydrocarbon aryl moiety include substituted or unsubstituted phenyl, naphthyl, pyrenyl, anthryl, and phenanthryl. Examples of hetroary moieties include furyl, pyrrolyl, thienyl, oxazoyl, imidazoyl, thiazoyl, pyridyl, pyrimidinyl, quinazolinyl and indolyl.

The compound of Formula V can be:
1-{4-[Bis(2-chloroethyl)amino]phenyl}-3-(2-methylquinolin-4-yl)urea;
1-{4-[Bis(2-chloroethyl)amino]phenyl}-3-(6-methoxy-2-methylquinolin-4-yl)urea;
1-{4-[Bis(2-chloroethyl)amino]phenyl}-3-(7-methoxy-2-methylquinolin-4-yl)urea;
1-{4-[Bis(2-chloroethyl)amino]phenyl}-3-(6-fluoro-2-methyl-quinolin-4-yl)urea;
1-{4-[Bis(2-chloro-thyl)amino]phenyl}-3-(7-fluoro-2-methyl-quinolin-4-yl)urea;
1-{4-[Bis(2-chloroethyl)amino]phenyl}-3-(6-chloro-2-methylquinolin-4-yl)-urea 1-{4-[Bis(2-chloroethyl)amino]phenyl}-3-(7-chloro-2-methylquinolin-4-yl)urea;
1-{4-[Bis(2-chloroethyl)amino]phenyl}-3-(2-phenylquinolin-4-yl)urea;
1-{4-[Bis(2-chloroethyl)amino]phenyl}-3-[2-(4-fluorophenyl)quinolin-4-yl]urea;
1-{4-[Bis(2-chloroethyl)amino]phenyl}-3-[2-(3-fluorophenyl)quinolin-4-yl]urea;
1-{4-[Bis(2-chloroethyl)amino]phenyl}-3-[2-(2-fluorophenyl)quinolin-4-yl]urea;
1-{4-[Bis(2-chloroethyl)amino]phenyl}-3-[2-(4-chlorophenyl)quinolin-4-yl]urea;
1-{4-[Bis(2-chloroethyl)-amino]phenyl}-3-[2-(3-chlorophenyl)quinolin-4-yl]urea;
1-{4-[Bis(2-chloroethyl)amino]phenyl}-3-[2-(2-chlorophenyl)quinolin-4-yl]urea;
1-{4-[Bis(2-chloroethyl)amino]phenyl}-3-[2-(4-bromophenyl)quinolin-4-yl]urea;

1-{4-[Bis(2-chloroethyl)amino]phenyl}-3-[2-(3-bromophenyl)quinolin-4-yl]urea;
1-{4-[Bis(2-chloroethyl)amino]phenyl}-3-[2-(2-bromophenyl)quinolin-4-yl]-urea;
1-{4-[Bis(2-chloroethyl)amino]phenyl}-3-(2-p-tolylquinolin-4-yl)urea;
1-{4-[Bis(2-chloroethyl)amino]phenyl}-3-(2-m-tolylquinolin-4-yl)urea;
1-{4-[Bis(2-chloroethyl)amino]phenyl}-3-(2-o-tolylquinolin-4-yl)urea;
1-{4-[Bis(2-chloroethyl)amino]phenyl}-3-[2-(4-methoxyphenyl)quinolin-4-yl]urea;
1-{4-[Bis(2-chloroethyl)amino]phenyl}-3-[2-(3-methoxyphenyl)quinolin-4-yl]urea;
1-{4-[Bis(2-chloroethyl)amino]phenyl}-3-[2-(2-methoxyphenyl)quinolin-4-yl]urea;
1-{4-[Bis(2-chloroethyl)amino]phenyl}-3-[2-(2,4-difluorophenyl)quinolin-4-yl]urea;
1-{4-[Bis(2-chloroethyl)amino]phenyl}-3-[2-(2,5-difluorophenyl)quinolin-4-yl]urea;
1-{4-[Bis(2-chloroethyl)amino]phenyl}-3-[2-(2,6-difluorophenyl)quinolin-4-yl]urea;
1-{4-[Bis(2-chloroethyl)amino]phenyl}-3-[2-(3,4-difluorophenyl)quinolin-4-yl]urea;
1-{4-[Bis(2-chloroethyl)amino]phenyl}-3-[2-(3,5-difluorophenyl)quinolin-4-yl]urea;
1-{4-[Bis(2-chloroethyl)amino]phenyl}-3-[2-(2,4-dichlorophenyl)quinolin-4-yl]urea;
1-{4-[Bis(2-chloroethyl)amino]phenyl}-3-[2-(2,5-dichlorophenyl)quinolin-4-yl]urea;
1-{4-[Bis(2-chloroethyl)amino]phenyl}-3-[2-(2,6-dichlorophenyl)quinolin-4-yl]urea;
1-{4-[Bis(2-chloroethyl)amino]phenyl}-3-[2-(3,4-dichlorophenyl)quinolin-4-yl]urea;
1-{4-[Bis(2-chloroethyl)amino]phenyl}-3-[2-(3,5-dichlorophenyl)quinolin-4-yl]urea;
1-{4-[Bis(2-chloroethyl)amino]phenyl}-3-[2-(2,4-dimethoxy-phenyl)quinolin-4-yl]-urea;
1-{4-[Bis(2-chloroethyl)amino]phenyl}-3-[2-(2,5-dimethoxy-phenyl)quinolin-4-yl]-urea;
1-{4-[Bis(2-chloroethyl)amino]phenyl}-3-[2-(3,4-dimethoxy-phenyl)quinolin-4-yl]-urea;
1-{4-[Bis(2-chloroethyl)amino]phenyl}-3-[2-(3,5-dimethoxy-phenyl)quinolin-4-yl]-urea;
1-{4-[Bis(2-chloroethyl)amino]phenyl}-3-[2-(4-hydroxy-3-methoxyphenyl)quinolin-4-yl]urea;
1-{4-[Bis(2-chloroethyl)amino]phenyl}-3-[6-methoxy-2-(4-methoxyphenyl)quinolin-4-yl]urea;
1-{4-[Bis(2-chloroethyl)amino]phenyl}-3-[6-methoxy-2-(3-methoxyphenyl)quinolin-4-yl]urea;
1-{4-[Bis(2-chloroethyl)amino]phenyl}-3-[6-methoxy-2-(2-methoxyphenyl)quinolin-4-yl]urea;
1-{4-[Bis(2-chloroethyl)amino]phenyl}-3-[7-methoxy-2-(4-methoxyphenyl)quinolin-4-yl]urea;
1-{4-[Bis(2-chloroethyl)amino]phenyl}-3-[2-(4-fluorophenyl)-6-methoxy-quinolin-4-yl]urea;
1-{4-[Bis(2-chloroethyl)amino]phenyl}-3-[2-(3-fluorophenyl)-6-methoxyquinolin-4-yl]urea;
1-{4-[Bis(2-chloroethyl)amino]phenyl}-3-[6-fluoro-2-(4-methoxyphenyl)quinolin-4-yl]urea;
1-{4-[Bis(2-chloroethyl)amino]phenyl}-3-[6-fluoro-2-(3-methoxyphenyl)quinolin-4-yl]urea;
1-{4-[Bis(2-chloroethyl)amino]phenyl}-3-[2-(4-hydroxy-3-methoxyphenyl)-6-methoxyquinolin-4-yl]urea;
1-{4-[Bis(2-chloroethyl)amino]phenyl}-3-[2-(3,4,5-trimethoxyphenyl)-quinolin-4-yl]-urea; and
1-{4-[Bis(2-chloroethyl)amino]phenyl}-3-[6-methoxy-2-(3,4,5-trimethoxy-phenyl)-quinolin-4-yl]urea.

The compounds of the present invention include compounds of Formula VI:

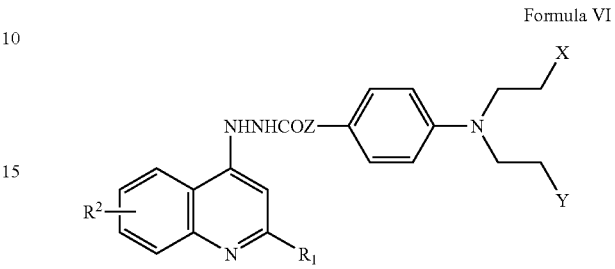

Formula VI wherein Z is NH or O;
each of X and Y can be, independently, Cl, Br, I, or $OSO_2Me$;
each of $R^1$ and $R^2$ is, independently, hydrogen, $C_1$-$C_6$ alkyl, alkyloxy, or aryl.

The term "aryl" refers both hydrocarbon aryl moieties and hetroaryl moietys. Examples of hydrocarbon aryl moiety include substituted or unsubstituted phenyl, naphthyl, pyrenyl, anthryl, and phenanthryl. Examples of hetroary moieties include furyl, pyrrolyl, thienyl, oxazoyl, imidazoyl, thiazoyl, pyridyl, pyrimidinyl, quinazolinyl and indolyl.

The representative compounds of Formula VI include:
N-{4-[Bis(2-chloroethyl)amino]phenyl}-2-(2-methylquinolin-4-yl)hydrazinecarboxamide;
N-{4-[Bis(2-chloroethyl)amino]phenyl}-2-(6-methoxy-2-methylquinolin-4-yl)hydrazinecarboxamide;
N-{4-[Bis(2-chloroethyl)amino]phenyl}-3-(7-methoxy-2-methylquinolin-4-yl)-hydrazinecarboxamide;
N-{4-[Bis(2-chloroethyl)amino]phenyl}-3-(6-fluoro-2-methyl-quinolin-4-yl)-hydrazinecarboxamide;
N-{4-[Bis(2-chloro-thyl)amino]phenyl}-3-(7-fluoro-2-methyl-quinolin-4-yl)-hydrazinecarboxamide;
N-{4-[Bis(2-chloroethyl)amino]phenyl}-3-(6-chloro-2-methylquinolin-4-yl)-hydrazinecarboxamide;
N-{4-[Bis(2-chloroethyl)amino]phenyl}-3-(7-chloro-2-methylquinolin-4-yl)-hydrazinecarboxamide;
N-{4-[Bis(2-chloroethyl)amino]phenyl}-3-(2-phenylquinolin-4-yl)-hydrazinecarboxamide;
N-{4-[Bis(2-chloroethyl)amino]phenyl}-3-[2-(4-fluorophenyl)quinolin-4-yl]-hydrazinecarboxamide;
N-{4-[Bis(2-chloroethyl)amino]phenyl}-3-[2-(3-fluorophenyl)quinolin-4-yl]-hydrazinecarboxamide;
N-{4-[Bis(2-chloroethyl)amino]phenyl}-3-[2-(2-fluorophenyl)quinolin-4-yl]-hydrazinecarboxamide;
N-{4-[Bis(2-chloroethyl)amino]phenyl}-3-[2-(4-chlorophenyl)quinolin-4-yl]-hydrazinecarboxamide;
N-{4-[Bis(2-chloroethyl)-amino]phenyl}-3-[2-(3-chlorophenyl)quinolin-4-yl]-hydrazinecarboxamide;
N-{4-[Bis(2-chloroethyl)amino]phenyl}-3-[2-(2-chlorophenyl)quinolin-4-yl]-hydrazinecarboxamide;
N-{4-[Bis(2-chloroethyl)amino]phenyl}-3-[2-(4-bromophenyl)quinolin-4-yl]-hydrazinecarboxamide;
N-{4-[Bis(2-chloroethyl)amino]phenyl}-3-[2-(3-bromophenyl)quinolin-4-yl]-hydrazinecarboxamide;
N-{4-[Bis(2-chloroethyl)amino]phenyl}-3-[2-(2-bromophenyl)quinolin-4-yl]-urea;
N-{4-[Bis(2-chloroethyl)amino]phenyl}-3-(2-p-tolylquinolin-4-yl)-hydrazinecarboxamide;

N-{4-[Bis(2-chloroethyl)amino]phenyl}-3-(2-m-tolylquinolin-4-yl)-hydrazinecarboxamide;
N-{4-[Bis(2-chloroethyl)amino]phenyl}-3-(2-o-tolylquinolin-4-yl)-hydrazinecarboxamide;
N-{4-[Bis(2-chloroethyl)amino]phenyl}-3-[2-(4-methoxyphenyl)quinolin-4-yl]-hydrazinecarboxamide;
N-{4-[Bis(2-chloroethyl)amino]phenyl}-3-[2-(3-methoxyphenyl)quinolin-4-yl]-hydrazinecarboxamide;
N-{4-[Bis(2-chloroethyl)amino]phenyl}-3-[2-(2-methoxyphenyl)quinolin-4-yl]-hydrazinecarboxamide;
N-{4-[Bis(2-chloroethyl)amino]phenyl}-3-[2-(2,4-difluorophenyl)quinolin-4-yl]-hydrazinecarboxamide;
N-{4-[Bis(2-chloroethyl)amino]phenyl}-3-[2-(2,5-difluorophenyl)quinolin-4-yl]-hydrazinecarboxamide;
N-{4-[Bis(2-chloroethyl)amino]phenyl}-3-[2-(2,6-difluorophenyl)quinolin-4-yl]-hydrazinecarboxamide;
N-{4-[Bis(2-chloroethyl)amino]phenyl}-3-[2-(3,4-difluorophenyl)quinolin-4-yl]-hydrazinecarboxamide;
N-{4-[Bis(2-chloroethyl)amino]phenyl}-3-[2-(3,5-difluorophenyl)quinolin-4-yl]-hydrazinecarboxamide;
N-{4-[Bis(2-chloroethyl)amino]phenyl}-3-[2-(2,4-dichlorophenyl)quinolin-4-yl]-hydrazinecarboxamide;
N-{4-[Bis(2-chloroethyl)amino]phenyl}-3-[2-(2,5-dichlorophenyl)quinolin-4-yl]-hydrazinecarboxamide;
N-{4-[Bis(2-chloroethyl)amino]phenyl}-3-[2-(2,6-dichlorophenyl)quinolin-4-yl]-hydrazinecarboxamide;
N-{4-[Bis(2-chloroethyl)amino]phenyl}-3-[2-(3,4-dichlorophenyl)quinolin-4-yl]-hydrazinecarboxamide;
N-{4-[Bis(2-chloroethyl)amino]phenyl}-3-[2-(3,5-dichlorophenyl)quinolin-4-yl]-hydrazinecarboxamide;
N-{4-[Bis(2-chloroethyl)amino]phenyl}-3-[2-(2,4-dimethoxy-phenyl)quinolin-4-yl]-hydrazinecarboxamide;
N-{4-[Bis(2-chloroethyl)amino]phenyl}-3-[2-(2,5-dimethoxy-phenyl)quinolin-4-yl]-hydrazinecarboxamide;
N-{4-[Bis(2-chloroethyl)amino]phenyl}-3-[2-(3,4-dimethoxy-phenyl)quinolin-4-yl]-hydrazinecarboxamide;
N-{-[Bis(2-chloroethyl)amino]phenyl}-3-[2-(3,5-dimethoxy-phenyl)quinolin-4-yl]-hydrazinecarboxamide;
N-{4-[Bis(2-chloroethyl)amino]phenyl}-3-[2-(4-hydroxy-3-methoxyphenyl)quinolin-N-yl]hydrazinecarboxamide;
N-{4-[Bis(2-chloroethyl)amino]phenyl}-3-[6-methoxy-2-(4-methoxyphenyl)quinolin-4-yl]hydrazinecarboxamide;
N-{4-[Bis(2-chloroethyl)amino]phenyl}-3-[6-methoxy-2-(3-methoxyphenyl)quinolin-4-yl]hydrazinecarboxamide;
N-{4-[Bis(2-chloroethyl)amino]phenyl}-3-[6-methoxy-2-(2-methoxyphenyl)quinolin-4-yl]hydrazinecarboxamide;
N-{4-[Bis(2-chloroethyl)amino]phenyl}-3-[7-methoxy-2-(4-methoxyphenyl)quinolin-4-yl]hydrazinecarboxamide;
N-{4-[Bis(2-chloroethyl)amino]phenyl}-3-[2-(4-fluorophenyl)-6-methoxy-quinolin-4-yl]hydrazinecarboxamide;
N-{4-[Bis(2-chloroethyl)amino]phenyl}-3-[2-(3-fluorophenyl)-6-methoxyquinolin-4-yl]hydrazinecarboxamide;
N-{4-[Bis(2-chloroethyl)amino]phenyl}-3-[6-fluoro-2-(4-methoxyphenyl)quinolin-4-yl]hydrazinecarboxamide;
N-{4-[Bis(2-chloroethyl)amino]phenyl}-3-[6-fluoro-2-(3-methoxyphenyl)quinolin-4-yl]hydrazinecarboxamide;
N-{4-[Bis(2-chloroethyl)amino]phenyl}-3-[2-(4-hydroxy-3-methoxyphenyl)-6-methoxyquinolin-4-yl]hydrazinecarboxamide;
N-{4-[Bis(2-chloroethyl)amino]phenyl}-3-[2-(3,4,5-trimethoxyphenyl)-quinolin-4-yl]-hydrazinecarboxamide;
N-{4-[Bis(2-chloroethyl)amino]phenyl}-3-[6-methoxy-2-(3,4,5-trimethoxy-phenyl)-quinolin-4-yl]hydrazinecarboxamide;
4-[Bis(2-chloroethyl)amino]phenyl-2-(2-methylquinolin-4-yl)hydrazinecarboxylate;
4-[Bis(2-chloroethyl)amino]phenyl-2-(6-methoxy-2-methylquinolin-4-yl)hydrazinecarboxylate
4-[Bis(2-chloroethyl)amino]phenyl-3-(7-methoxy-2-methylquinolin-4-yl)-hydrazinecarboxylate;
4-[Bis(2-chloroethyl)amino]phenyl-3-(6-fluoro-2-methylquinolin-4-yl)-hydrazinecarboxylate;
4-[Bis(2-chloro-thyl)amino]phenyl-3-(7-fluoro-2-methylquinolin-4-yl)-hydrazinecarboxylate;
4-[Bis(2-chloroethyl)amino]phenyl-3-(6-chloro-2-methylquinolin-4-yl)-hydrazinecarboxylate;
4-[Bis(2-chloroethyl)amino]phenyl-3-(7-chloro-2-methylquinolin-4-yl)-hydrazinecarboxylate; and
4-[Bis(2-chloroethyl)amino]phenyl-3-(2-phenylquinolin-4-yl)hydrazinecarboxylate.

The compounds of the invention also include compounds of Formula VII:

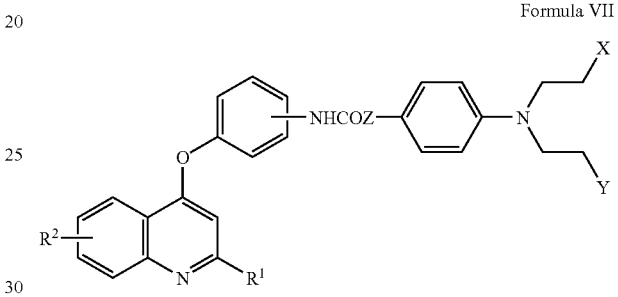

Formula VII

In the above formula, Z is NH or O;
each X and Y is, independently, Cl, Br, I, or $OSO_2Me$;
each of $R^1$ and $R^2$ is, independently, hydrogen, $C_1$-$C_6$ alkyl, alkyloxy, or aryl.

The term "aryl" refers both hydrocarbon aryl moieties and hetroaryl moietys. Examples of hydrocarbon aryl moiety include substituted or unsubstituted phenyl, naphthyl, pyrenyl, anthryl, and phenanthryl. Examples of hetroary moieties include furyl, pyrrolyl, thienyl, oxazoyl, imidazoyl, thiazoyl, pyridyl, pyrimidinyl, quinazolinyl and indolyl.

The representative compounds of Formula VII include:
N-{4-[bis(2-chloroethyl)amino]phenyl}-N'-(4-{[6-methoxy-2-methylquinolin-4-yl]oxy}phenyl)urea;
N-{4-[Bis(2-chloroethyl)amino]phenyl}-N'-(4-{[2-methylquinolin-4-yl)]oxy}-phenyl)urea;
N-{4-[Bis(2-chloroethyl)amino]phenyl}-N'-(4-{[6-methoxy-2-methylquinolin-4-yl)]oxy}phenyl)urea;
N-{4-[Bis(2-chloroethyl)amino]phenyl}-N'-(4-{[6-fluoro-2-methylquinolin-4-yl)]oxy}phenyl)urea;
N-{4-[bis(2-chloroethyl)amino]phenyl}-N'-{4-[(6-methyl[1,3]dioxolo[4,5-g]quinolin-8-yl)oxy]phenyl}urea
N-{4-[Bis(2-chloroethyl)amino]phenyl}-N'-(4-{[2-phenylquinolin-4-yl)]oxy}phenyl)urea;
N-{4-[Bis(2-chloroethyl)amino]phenyl}-N'-(4-{[2-(4-methoxyphenyl)quinoline-4-yl)]-oxy}phenyl)urea;
N-{4-[Bis(2-chloroethyl)amino]phenyl}-N'-(4-{[2-(3,5-dichlorophenyl)quinoline-4-yl)]oxy}phenyl)urea;
N-{4-[Bis(2-chloroethyl)amino]phenyl}-N'-(4-{[2-(6-methoxy-2-(4-methoxyphenyl)-quinolin-4-yl)]oxy}phenyl)urea;
4-[Bis(2-chloroethyl)amino]phenyl-4-{[2-methylquinolin-4-yl]oxy}phenyl)phenylcarbamate;
4-[Bis(2-chloroethyl)amino]phenyl-4-{[2-methylquinolin-4-yl]oxy}phenyl)phenylcarbamate;
4-[Bis(2-chloroethyl)amino]phenyl-4-{[6-methoxy-2-methylquinolin-4-yl]oxy}-phenyl)phenylcarbamate;

4-[Bis(2-chloroethyl)amino]phenyl-4-{[6-fluoro-2-methylquinolin-4-yl]oxy}phenyl)phenylcarbamate;

4-[Bis(2-chloroethyl)amino]phenyl-4-{[2-phenylquinolin-4-yl]oxy}phenyl)phenylcarbamate;

4-[Bis(2-chloroethyl)amino]phenyl-4-{[2-(4-methoxyphenyl)quinoline-4-yl]oxy}-phenyl)phenylcarbamate and 4-[Bis(2-chloroethyl)amino]phenyl-4-{[2-(3,5-dichlorophenyl)quinoline-4-yl]oxy}-phenyl)phenylcarbamate.

The compounds of the present invention also include compounds of Formula VIII:

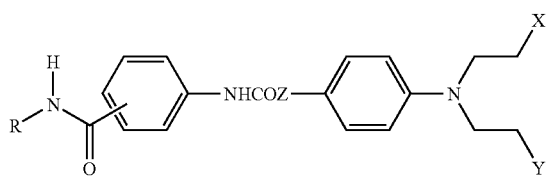

Formula VIII wherein Z is NH or O;
each X and Y is, independently, Cl, Br, I, or OSO$_2$Me;
R is (CH$_2$)nNR$^1$R$^2$, (CH$_2$)nCH(OH)CH$_2$OH, (CH$_2$)n-N-morpholine, piperidine, 4-piperidinopiperidine, morpholine, residue, etc.; and
R$^1$, R$^2$ is, independently, C$_1$-C$_6$ alkyl, n is 1-5.

The (CH$_2$)nNR$^1$R$^2$ can be formed acid salts with inorganic acids such as HCl. HBr, HI, H$_2$SO$_4$, etc., or organic acid such as HCOOH, CH$_3$COOH, citric acid, oxalic acid, tartaric acid, etc.

The compounds of the present application also include:

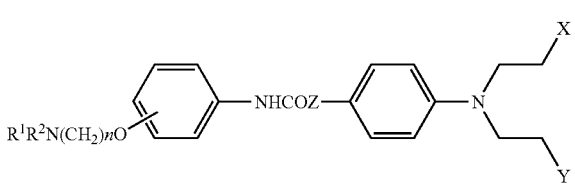

Formula IX wherein Z is NH or O;
each X and Y is independently or are the same, and can be Cl, Br, I, or OSO$_2$Me; and
wherein R$^1$, R$^2$ is, independently, C$_1$-C$_6$ alkyl, n is 1-5.

The (CH$_2$)nNR$^1$R$^2$ can be formed acid salts with inorganic acids such as HCl. HBr, HI, H$_2$SO$_4$, etc., or organic acid such as HCOOH, CH$_3$COOH, citric acid, oxalic acid, tartaric acid, etc.

The following are some of the representative compounds of Formula VII:

1-{4-[Bis(2-chloroethyl)amino]phenyl}-3-[3-(2-dimethylaminoethoxy)-phenyl]urea

1-{4-[Bis(2-chloroethyl)amino]phenyl}-3-[3-(3-dimethylaminopropoxy)phenyl]urea

1-{4-[Bis(2-chloroethyl)amino]-phenyl}-3-[3-(2,3-dihydroxypropoxy)phenyl]urea 3-(3-{4-[Bis(2-chloroethyl)amino]phenyl}ureido)-N,N-bis(2-hydroxyethyl)benzamide 3-[(3-{4-[Bis(2-chloroethyl)amino]phenoxycarbonylamino}benzoyl)carboxyamino]-propionic acid The compounds included in this new invention can be synthesized using conventional techniques. Advantageously, these compounds are conveniently synthesized from readily available starting materials and standard organic chemistry synthesis methods, including those methods illustrated in the schemes and the examples herein.

GENERAL PROCEDURE

1. Preparation of 4-[N,N-bis(2-chloroethyl)amino]phenylcarbamoyl chloride (38) and 4-[N,N-bis(2-chloroethyl)amino]phenylisocyanate (39)

The known N,N-bis(2-chloroethyl)benzene-1,4-diamine dihydrochloride (37) is prepared by following the literature procedure[35] with modification (Scheme 7). The commercially available 4-fluoronitrobenzene (34) is reacted with diethanolamine under refluxing to give 4-[N,N-bis(2-hydroxyethyl)amino]nitrobenzene (35), which is then converted to 4-[N,N-bis(2-chloroethyl)amino]nitrobenzene (36) by treating with thionyl chloride. Catalytic hydrogenation (10% Pd/C, H$_2$) of compound 36 in ethyl acetate affords N,N-bis(2-chloroethyl)benzene-1,4-diamine (37), which is immediately treated with HCl in ethyl acetate to yield hydrochloride salt of 37. The hydrochloride salt 37 and a catalytic amount of active charcoal are suspended in anhydrous dioxane (or CHCl$_3$ and THF) and cooled to −5 to −10° C. To this, diphosgene (1.1-1.3 equivalent) in dried dioxane (or CHCl$_3$ and THF) is added dropwise during 10 min. The reaction mixture, which appears the precipitates of mustard carbamoyl hydrochloride (38), is then heated at 90-95° C. until the elaboration of HCl is ceased (about 5-6 h). The reaction mixture is then filtered through a pad of Celite, washed with a small amount of the solvent used. The filtrate and the washings are combined and concentrated to 5-10 mL to yield the crude mustard isocyanate 39,[36] which is used directly for the next reaction without further purification. Compound 37, 38, and 39 can be used for the synthesis of the newly invented compounds.

Scheme 3

$$O_2N-\underset{34}{\phenyl}-F \xrightarrow{NH(CH_2CH_2OH)_2} O_2N-\underset{35}{\phenyl}-N(CH_2CH_2CH)_2 \xrightarrow{SOCl_2} O_2N-\underset{36}{\phenyl}-N(CH_2CH_2Cl)_2$$

$$\Bigg\downarrow 10\% \text{ Pd/C, H}_2 \atop \text{HCl}$$

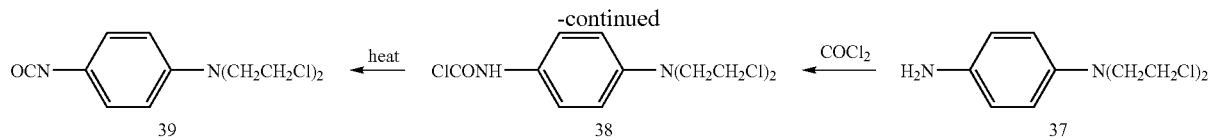

2. Synthesis of Phenol Mustard

Phenol N-mustard is synthesized by to known procedures with modification. Scheme 8 shows the synthetic route for phenol mustard. Treatment of 4-nitrophenol (40) with benzyl chloride or 4-fluoro-1-nitrobenzene (42) with benzyl alcohol in the presence of base (such as NaOH, KOH, $Na_2CO_3$, $K_2CO_3$ or organic base) gives compound 41, which is converted into 4-benzyloxyaniline (43) by reduction (Fe/$CH_3COOH$ or Pd/C, $H_2$). Treatment of 43 with ethylene oxide affords 4-N,N-bis(2-hydroxyethyl)aminophenyl benzyl ether 40.[37] Alternatively, the intermediate 44 can be prepared by reacting 4-hydroxyaniline (45) with 2-chloroethanol in the presence of $Na_2CO_3$ followed with benzyl bromide.[38]

Treatment of 44 with thionyl chloride (or $POCl_3$, methanesulfonyl chloride/pyridine, and other halogenating reagents) yields 4-N,N-bis(2-chloroethyl)aminophenyl benzyl ether 47. The O-benzyl protecting function of 47 is removed by catalytic hydrogenation or by treating with $HCl/CH_3COOH$ to give the desired phenol mustard 48, which is then treated with phosgene affords 4-[bis(2-chloroethyl)amino]phenyl-chloridocarbamate (49). One can also convert 48 to 4-[N,N-bis(2-chloroethyl)aminophenyl-4-nitrophenyl carbonate (50) by reacting with p-nitrochiroformate/$Et_3N$ to yield 4-[N,N-bis(2-chloroethyl)aminophenyl-4-nitro-phenyl carbonate (50).[39-41] Both 49 and 50 can be used for the synthesis of the target compounds having a carbamic acid ester linkage.

Scheme 4

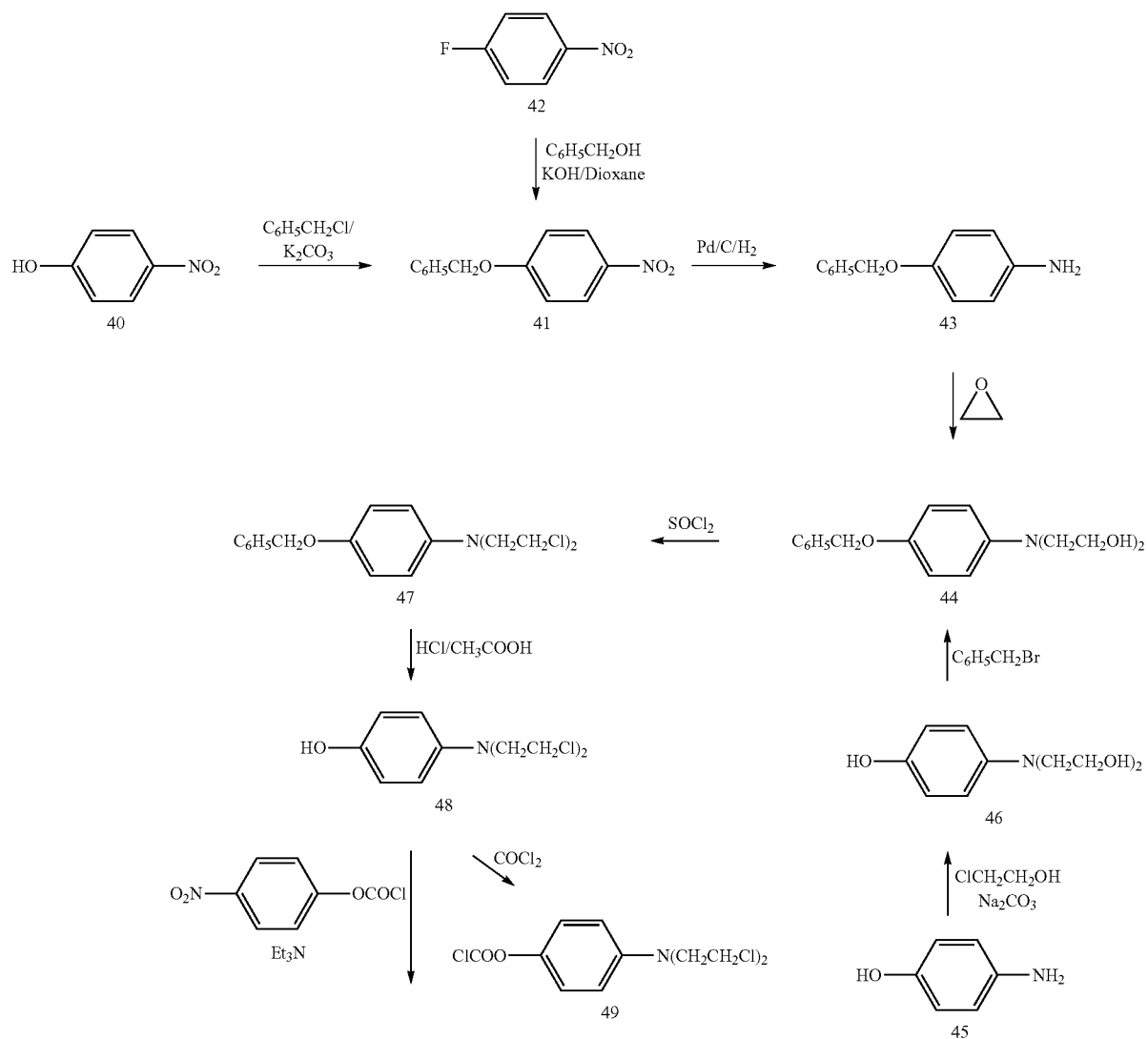

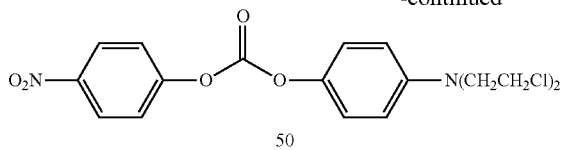
50

2. Synthesis of 4-aminoquinoline Derivatives

4-Aminoquinolines used for the synthesis of Formula V compounds can be synthesized starting from quinolin-4-ones, which can be prepared by methods described in literatures[42,43,44] (Scheme 5). Treatment of quinolin-4-ones (51) with phosphorus oxyxhloride (or thionyl chloride) gives 4-chloroquinolines (52), which is further reacted with a mixture of phenol and ammonia at 180° C. to afford 4-aminoquinolines (53).

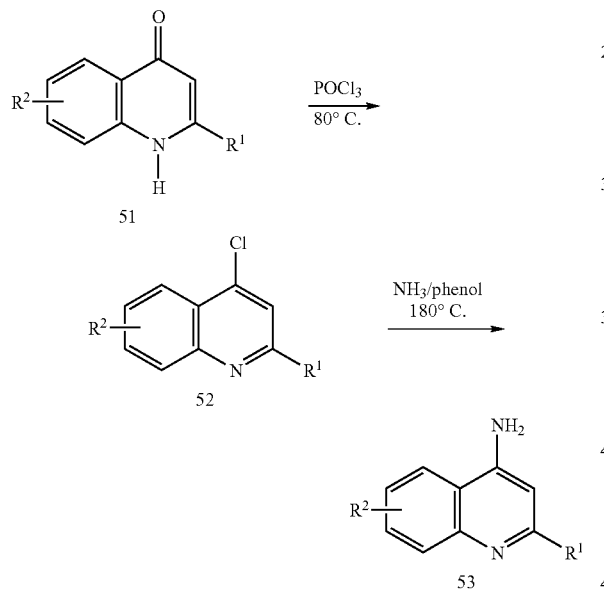

Scheme 5

4. Synthesis of 4-quinolylhydrazone Derivatives (54)

4-Quinolylhydrazones used for the synthesis of compound of Class VI will be synthesized starting from 4-chloroquinolines (52) according to the literature procedures.[44-48] A mixture of 4-chloroqinolines (52) and 80% hydrazine hydrate aqueous solution will be refluxed in ethanol to afford 4-quinolylhydrazones (54) (Scheme 6).

Scheme 6

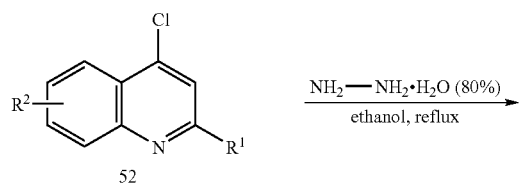

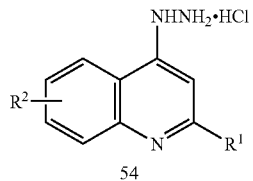
54

$R^1$ = Me or substituted benzenes (i.e., 3'-MeOC$_6$H$_4$, 2'-FC$_6$H$_4$, 3'-ClC$_6$H$_4$, etc.
$R^2$ = H, F, Cl, Me, OMe, NMe$_2$ or cyclic amine

5. Synthesis of 4-quinolyloxyaniline Derivatives (56)

4-Quinolyloxy anilines (56) used for preparing compounds of Class VII will be prepared by the reaction of 4-chloroquinolines (52) with 3- or 4-nitrophenol at 140-150° C. to give 4-(4-nitrophenoxy)quinolines derivatives (55) by following procedure described previously.[49-51] The nitro group in 55 will be reduced (Pd/C/H$_2$ or Zn/MeOH/reflux) to yield the corresponding aniline derivatives 56 (Scheme 7).

Scheme 7

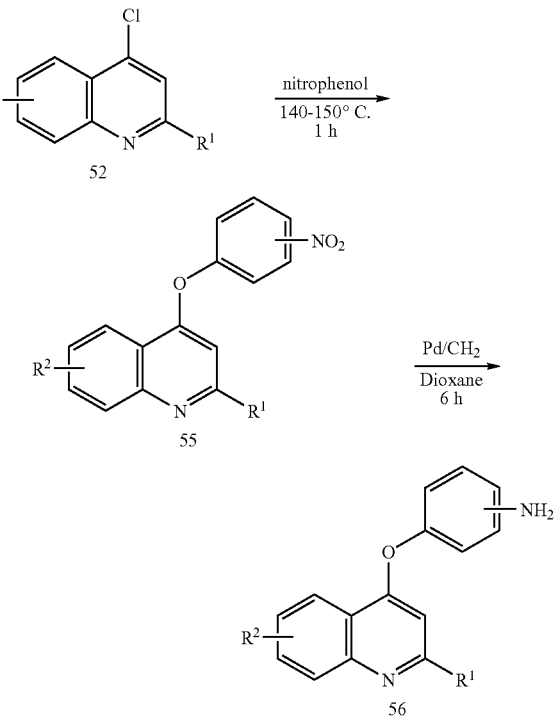

Where $R^1$ = Me or substituted benzenes (i.e., 3'-MeOC$_6$H$_4$, 2'-FC$_6$H$_4$, 3'-ClC$_6$H$_4$, etc.
$R^2$ = H, OMe, NMe$_2$, O—CH$_2$—O, F, Cl, Br or cyclic amine

6. Synthesis of Compounds of Formula I-Formula VII Containing a Urea or Carbamic Acid Ester Linkage Compounds of Formula I-VII can be prepared by reacting 9-anilinoacridines (57, 58, and 59), 9-aminoacridines (60), or 4-aminoquinolines (53, 54, 56) with N-mustards i.e., 38, 39, 49 or 50) in a proper solvent (such as $CHCl_3$, THF, dioxane or DMF) in the presence of base (such as pyridine, triethylamine, DMAP, etc.) at room temperature to 60° C. as shown in Scheme 10.

Similarly, compounds of Formula VIII can be synthesized starting from nitro-substituted benzoic acids (61) (Scheme 9).

Preferentially, 3-nitrobenzoic acid is the starting material. Treatment of compound 61 with thionyl chloride (or $PCl_5$, $POCl_3$) gives benzoic acid chloride 62, which is reacted with N,N-dialkylaminalkylamines [such as N,N-dimethylethylamine, N,N-dimethylpropyl-amine], cyclic amines (such as piperidinopiperidine), or alkyl amino acid esters, etc.) to give benzoycarboxamides 63. The nitro function of 63 is reduced to corresponding aniline derivatives 64, which is then reacted with N-mustard (i.e., 38, 39, 49, or 50) to give the desired compounds of Formula VIII. The water-soluble derivatives can be formed by treating with inorganic acid (such as hydrochloric acid, sulfuric acid, etc.) or organic acid ((such as acetic acid, citric acid, etc).

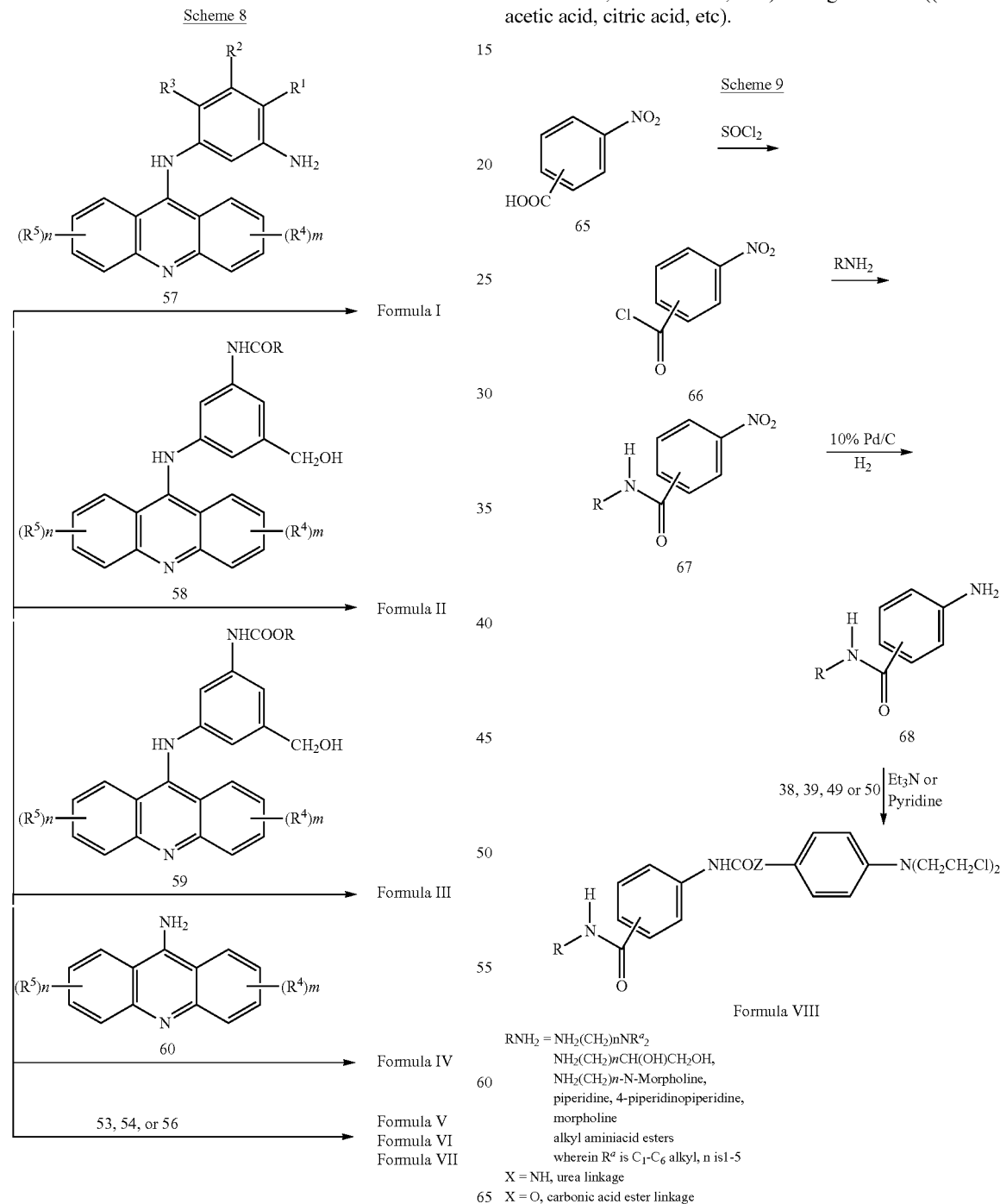

Compounds of Formula IX can be prepared from nitrophenols, preferring, from 3-nitrophenol (Scheme 10). Reaction of nitrophenols (65) with N,N-dialkylaminoalkyl halides (such as N,N-methylaminoethyl chloride, N,N-methylaminopropyl chloride, etc.) or glycosylation of 65 will give 66, which is then reduced to aniline derivatives 67. Condensation of 67 with N-mustards (i. e., 38, 39, 49 or 50) will afford the desired compound of Formula IX.

Scheme 10

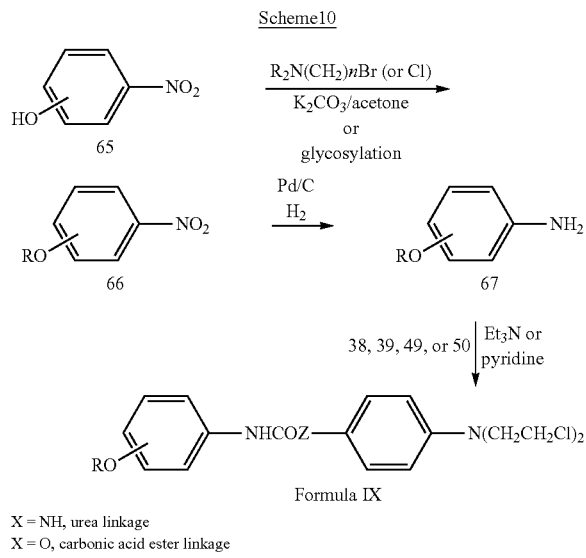

X = NH, urea linkage
X = O, carbonic acid ester linkage
R = (CH$_2$)$_n$NMe$_2$ or sugars

EXAMPLES

The specific examples below are to be constructed as merely illustrative, and not limitative of the remainder of the disclosure in any way whatsoever.

Example 1

1-[3-(Acridin-9-ylamino)-5-hydroxymethylphenyl]-3-{4-[bis(2-chloroethyl)amino]phenyl}-urea (15, BO-1037)

To a suspension of N,N-bis(2-chloroethyl)benzene-1,4-diamine hydrochloride (37) (0.306 g, 1.0 mmol) in dry THF (25 mL) was added dropwise a solution of diphosgene (197 mg, 1.2 mmol) in an ice bath with vigorous stirring. After being stirred for 30 min, it formed the known crude p-[(N,N-bis(2-chloroethyl)amino)]phenylcarbamoyl chloride hydrochloride (38). The reaction mixture was then neutralized by adding Et$_3$N (0.5 mL), continuously stirred for 10 min, filtered through a pad of Celite and washed with THF (5 mL). The filtrate and washings were combined and was added dropwise into a solution of 3-(acridin-9-yl)amino-5-hydroxymethylaniline (6, AHMA)[18] (0.351 g, 1.0 mmol) in dry DMF (10 mL) containing Et$_3$N (0.5 mL) at 0° C. After being stirred for 18 h, the reaction mixture was evaporated in vacuo to dryness and the residue was dissolved in a mixture of CHCl$_3$/MeOH, mixed with silica gel (5 gm) and evaporated in vacuo to dryness. The residue was put on the top of a silica gel column (2×20 cm) and chromatographed using CHCl$_3$/MeOH (100:5 v/v) as eluent. The fractions containing the main product were combined and evaporated in vacuo to dryness and residue was recrystalized from CHCl$_3$/MeOH to give 1-[3-(acridin-9-ylamino)-5-hydroxymethylphenyl]-3-{4-[bis(2-chloroethyl)amino]phenyl}urea (15, BO-1037), 205 mg (35%); mp 173-175° C.; $^1$H NMR (DMSO-d$_6$) δ 3.67 (8H, m, 4×CH$_2$), 4.41 (2H, d, J=6.0 Hz, CH$_2$), 5.14 (1H, t, J=6.0 Hz, exchangeable, OH), 6.37 (1H, s, ArH), 6.68 (2H, d, J=9.1 Hz, 2×ArH,), 6.81 (1H, s, ArH), 7.01 (1H, s, ArH), 7.05-7.19 (1H, m, ArH), 7.24 (2H, d, J=9.1 Hz, 2×ArH), 7.55 (4H, m, 4×ArH) 8.05 (2H, m, 2×ArH), 8.25 (1H, m, ArH) 8.46 (1H, m, ArH), 10.48 (1H, brs, exchangeable, NH). Anal. Calcd. for (C$_{31}$H$_{29}$Cl$_2$N$_5$O$_2$): C, 63.81; H, 5.18; N, 12.00. Found: C, 64.07; H, 5.26; N, 11.87.

Example 2

1-{4-[bis(2-chloroethyl)amino]phenyl}-3-[3-hydroxymethyl-5-(4-methylacridin-9-ylamino)phenyl] urea (16, BO-1050)

A solution of diphosgene (197 mg, 1.2 mmol.) in dry CH$_3$Cl was added dropwise to a suspension of N,N-bis(2-chloroethyl)benzene-1,4-diamine hydrochloride (37) (0.306 g, 1.0 mmol) in dry THF (25 mL) containing Et$_3$N (0.5 mL) in an ice bath with vigorous stirring for 30 min. It formed crude p-[(N,N-bis(2-chloroethyl)amino)]phenylcarbamoyl chloride hydrochloride (38). The reaction mixture was filtered through a pad of Celite and washed with THF (5 mL). The filtrate and washings were combined and was then added dropwise into a solution of 3-amino-5-(4-methylacridin-9-ylamino)phenyl]-methanol[18] (0.329 mg, 1.0 mmol) in dry DMF (20 mL) containing Et$_3$N (0.5 mL) at 0° C. and stirred at room temperature for 16 h. The solvent was removed by distillation under reduced pressure to dryness and the residue was dissolved in CHCl$_3$/MeOH and mixed with silica gel (5 g) and then evaporated in vacuo to dryness. The residue was put on the top of a silica gel column (2×20 cm) and chromatographed using CHCl$_3$/MeOH (100:2 v/v) as eluent. The fractions containing the main product were combined and concentrated in vacuo and the residue was recrystallized from CHCl$_3$/MeOH to give 1-{4-[bis(2-chloroethyl)amino]phenyl}-3-[3-hydroxymethyl-5-(4-methylacridin-9-ylamino) phenyl]urea (16, BO-1050), 179 mg (30%); mp 251-252° C.; $^1$H NMR (DMSO-d$_6$) δ 3.64-3.71 (8H, m, 4×CH$_2$), 4.00 (3H, s, Me), 4.47 (2H, d, J=5.1 Hz, CH$_2$) 5.11 (1H, t, J=5.1 Hz, exchangeable, OH), 6.35 (1H, s, ArH), 6.68 (2H, d, J=8.8 Hz, 2×ArH) 6.75 (1H, s, ArH), 6.88-7.18 (4H, m, 4×Ar H), 7.24 (2H, d, J=8.8 Hz, 2×ArH) 7.52 (2H, s, 2×ArH), 7.83 (2H, s, 2×Ar H), 8.25 (1H, s, ArH) 8.40 (1H, s, ArH), 10.24 (1H, s, exchangeable, NH). Anal. Calcld. for (C$_{32}$H$_{31}$Cl$_2$N$_5$O$_2$.3H$_2$O): C, 59.81; H, 5.80; N, 10.89. Found: C, 59.74; H, 5.79; N, 9.67.

Example 3

1-{4-[Bis(2-chloroethyl)amino]phenyl}-3-[3-hydroxymethyl-5-(4-methylacridin-9-ylamino)phenyl] urea (17, BO-1051)

To a suspension of N,N-bis(2-chloroethyl)benzene-1,4-diamine hydrochloride (37) (1.836 g, 6 mmol) and charcoal (20 mg) in dry dioxane (40 mL) was added diphosgene (0.989 g, 5 mmol). The mixture was heated at 90-95° C. for 5 h. After cooling, the reaction mixture was filtered through a pad of Celite and the filtrate containing crude mustard isocyanate 39 was added dropwise into the solution of 4-methyl-N'-1'-(4-methylacridin-9-yl)benzene-1,3-diamine[33] (1.065 g, 3.4 mmol) in dry DMF (50 mL) containing pyridine (2 mL) at −10° C. The reaction mix was allowed to stir at room temperature for 19 h. The solvent removed under reduce pressure and the solid residue was recrystalized from CHCl$_3$:MeOH (1:10) to give 1-{4-[bis(2-chloroethyl)-amino]phenyl}-3-[3-hydroxymethyl-5-(4-methylacridin-9-yl-amino)phenyl]urea (17, BO-1051), 1.63 g (83.8%); mp 267-270° C.; $^1$H NMR (DMSO-d$_6$) δ 2.34 (3H, s, Me), 2.78 (3H, s, Me), 3.65-3.70 (8H, m, 4×CH$_2$), 6.68 (2H, d, J=9.4 Hz, 2×ArH), 6.87 (1H, m, ArH), 7.22-7.35 (3H, m, ArH), 7.35-7.43 (1H, m, ArH), 7.43-7.49 (1H, m, ArH), 7.86 (1H, d, m, ArH), 7.94-8.03 (1H, m, ArH), 8.13-8.26 (3H, m, 3×ArH), 8.28 (1H, brs, exchangeable, NH), 8.34 (1H, m, ArH), 9.35 (1H, brs, exchangeable, NH), 11.51 (1H, brs, exchangeable, NH). Anal. Calcld. for (C$_{32}$H$_{31}$Cl$_2$N$_5$O.2H$_2$O): C, 63.15; H, 3.13; N, 11.50. Found: C, 63.38; H, 3.52; N, 10.97.

Example 4

1-[3-(Acridin-9-yl-mino)-5-methylphenyl]-3-{4-[bis(2-chloroethyl)amino]phenyl}urea (18, BO-1079)

To a suspension of N,N-bis(2-chloroethyl)benzene-1,4-diamine hydrochloride (37) (0.918 g, 3.0 mmol) and charcoal (20 mg) in dry dioxane (30 mL) was added diphosgene (0.494 g, 2.5 mmol) and then heated at 90-95° C. for 5 h. The mixture was filtered through a pad of Celite and the filtrate containing crude N-mustard isocyanate 39 was added dropwise into the solution of N-acridin-9-yl-5-methylbenzene-1,3-diamine 33 (0.517 g, 1.7 mmol) in dry DMF (25 mL) containing pyridine (2 mL) at −10° C. The reaction mixture was allowed to cool down to room temperature and continuously stirred for 24 h and then evaporated in vacuo to dryness. The residue was dissolved in a mixture of CHCl$_3$/MeOH containing silica gel (10 g) and evaporated under reduced pressure to dryness. The residue was put on the top of a silica gel column (4×30 cm) and chromatographed by using CHCl$_3$/MeOH (100:3 v/v) as eluent. The fractions containing the main product were combined and evaporated in vacuo to dryness to give 1-[3-(acridin-9-ylamino)-5-methylphenyl]-3-{4-[bis(2-chloroethyl)amino]phenyl}urea (18, BO-1079), 0.375 g (39%); mp 280-285° C.; 1H NMR (DMSO-d6) δ 2.26 (3H, s, Me), 3.68 (8H, s, 4×CH2), 6.68 (2H, d, J=9.0 Hz, ArH) 6.75-6.89 (1H, m, ArH), 7.19-7.32 (3H, m, ArH), 7.40-7.62 (3H, m, ArH), 7.93-8.14 (4H, m, ArH), 8.29 (2H, d, J=9.0 Hz, ArH), 8.94 (1H, brs, exchangeable, NH), 9.37 (1H, brs, exchangeable, NH), 11.51 (1H, brs, exchangeable, NH). Anal. Calcld. for (C$_{31}$H$_{29}$C$_{12}$N$_5$.0.3 H$_2$O): C, 60.88; H, 6.11; N, 11.45. Found: C, 61.08; H, 6.18; N, 11.32.

Example 5

9-[5-(3-{4-[Bis(2-chloroethyl)amino]phenyl}ureido)-2-methylphenylamino]-5-methylacridine-4-carboxylic acid (2-dimethylaminoethyl)amide (19, BO-1053)

To a suspension of N,N-bis(2-chloroethyl)benzene-1,4-diamine hydrochloride (37) (0.918 g, 3 mmol) and charcoal (20 mg) in dry dioxane (30 mL) was added diphosgene (0.494 g, 2.5 mmol). The reaction mixture was heated at 90-95° C. for 5 h. After cooling, the reaction mixture was filtered through a pad of Celite and the filtrate containing crude mustard isocyanate 39 was added dropwise into the solution of 9-(5-amino-2-methyl-phenylamino)-5-methylacridine-4-carboxylic acid (2-dimethylaminoethyl)amide (0.732 g, 1.7 mmol)$^{33}$ in dry DMF (25 mL) containing pyridine (2 mL) at −10° C. and then stirred at room temperature for 24 h. The solvent removed under reduced pressure to dryness and the residue was dissolved in a mixture of CHCl$_3$/MeOH containing silica gel (10 gm) and evaporated in vacuo to dryness. The residue was put on the top of a silica gel column (4×30 cm) and chromatographed using CHCl$_3$/MeOH (100:5 v/v) as eluent. The fractions containing the main product were combined and evaporated in vacuo to dryness. The residue was recrystallized from EtOH/hexane to give 9-[5-(3-{4-[bis(2-chloroethyl)amino]phenyl}ureido)-2-methyl-phenylamino]-5-methyl-acridine-4-carboxylic acid (2-dimethylaminoethyl)amide (19, BO-1053); 0.385 g (32%); mp 286-289° C.; $^1$H NMR (DMSO-d$_6$) δ 2.19 (3H, s, Me), 2.67 (6H, m, NMe$_2$), 2.85 (3H, s, Me), 3.14 (2H, brs, CH$_2$), 3.63-3.69 (8H, m, 4×CH$_2$), 3.85 (2H, brs, CH$_2$), 6.41 (1H, m, ArH,), 6.65 (2H, d, J=9.0 Hz, ArH), 6.97 (1H, m, ArH), 7.24 (2H, d, J=9.0 Hz, ArH), 7.36-7.44 (1H, m, ArH), 7.51 (1H, m, ArH), 7.74 (2H, m, ArH), 7.93 (1H, m, ArH), 8.09 (1H, m, ArH), 8.41 (1H, m, ArH), 8.67 (1H, m, ArH), 9.04 (1H, brs, exchangeable, NH), 9.45 (1H, brs, exchangeable, NH), 12.18 (1H, brs, exchangeable, NH). Anal. Calcld. for (C$_{37}$H$_{41}$Cl$_2$N$_7$O$_2$.6H$_2$O): C, 54.91; H, 5.20; N, 12.34. Found: C, 55.08; H, 5.32; N, 12.44.

Example 6

1-Acridin-9-yl-3{4-[bis(2-chloroethyl)amino]phenyl}urea (20, BO-1034)

To a suspension of N,N-bis(2-chloroethyl)benzene-1,4-diamine hydrochloride (37, 0.306 g, 1 mmol) in dry THF (25 mL) was added dropwise a solution of diphosgene (197 mg, 1.2 mmol.) in an ice bath with vigorous stirring. After being stirred for 30 min, Et$_3$N (0.5 mL) wad added and continuously stirred for additional 10 min. The reaction mixture was filtered through a pad of Celite, washed with THF. The combined filtrate and washings (containing carbamoyl chloride 38) were then added dropwise into a solution of commercially available 9-aminoacridine hydrochloride (248 mg, 1.0 mmol) in dry DMF (10 mL) containing Et$_3$N (0.5 mL) at room temperature. After being stirred for 16 h, the solvent was evaporated under reduced pressure and the residue was dissolved in a mixture of CHCl$_3$/MeOH containing silica gel (5 g) and evaporated in vacuo to dryness. The residue was put on the top of a silica gel column (2×20 cm) using CHCl$_3$/MeOH (50/1 v/v) as eluent. The fractions containing the main product were combined and evaporated in vacuo to dryness and residue was recrystalized from acetone to give 1-acridin-9-yl-3-{4-[bis(2-chlorothyl)amino]phenyl}urea (20, BO-1034); 273 mg (60%); mp 184-186° C.; $^1$HNMR (DMSO-d$_6$) δ 3.71 (8H, s, 4×CH$_2$), 6.73 (2H, d, J=9.1 Hz, 2×ArH), 7.10-7.13 (2H, m, 2×ArH), 7.28-7.53 (3H, m, 3×ArH), 7.58-7.60 (2H, m, 2×ArH), 7.84 (1H, brs, exchangeable, NH), 8.15 (2H, d, J=9.1 Hz, 2×ArH), 8.22 (1H, m, ArH), 9.37 (1H, brs, exchangeable, NH). Anal. Calcld. for (C$_{24}$H$_{22}$Cl$_2$N$_4$O); C, 63.58; H, 4.89; N, 12.36. Found: C, 63.35; H, 5.05; N, 12.09.

Example 7

1-{4-[Bis(2-chloroethyl)amino]phenyl}-3-(2-methylquinolin-4-yl)urea (21, BO-1038)

To a suspension of N,N-bis(2-chloroethyl)benzene-1,4-diamine hydrochloride (37, 0.612 g, 2.0 mmol) in dry THF (35 mL) was added dropwise a solution of diphosgene (394 mg, 2.4 mmol.) in an ice bath with vigorous stirring. The known crude p-[(N,N-bis(2-chloroethyl)amino)]phenylcarbamoyl chloride hydrochloride (38) was formed after being stirred for 30 min. It was neutralized by adding Et$_3$N (1 mL) to give the free carbamoyl chloride, filtered through a pad of Celite, washed with THF (5 mL). The filtrate and washings were combined and then added dropwise into a solution of commercially available 4-amino-2-methylquinoline (0.177 g, 2.0 mmol) in dry DMF (15 mL) containing Et$_3$N (0.5 mL) at 0° C. After being stirred at room temperature for 3 h, the reaction mixture was heated at 40-45° C. for 16 h and then evaporated in vacuo to dryness. The residue was dissolved in a mixture of CHCl$_3$/MeOH, mixed silica gel (10 g) and then evaporated in vacuo to dryness. The residue was put on the top of a silica gel column (2×30 cm) and chromatographed using CHCl$_3$/MeOH (100:2 v/v) as eluent. The fractions containing the main product were combined and evaporated in vacuo to dryness and the residue was recrystallized from acetone to give 1-{4-[bis(2-chloroethyl)amino]phenyl}-3-(2-methylquinolin-4-yl)urea (21, BO-1038); 187 mg (40.1%); mp 128-129° C.; $^1$H NMR (CHCl$_3$-d$_6$) δ 2.63 (3H, s, Me), 3.57 (4H, t, J=6.6 Hz, 2×CH$_2$), 3.66 (4H t, J=6.6 Hz, 2×CH$_2$), 6.56 (2H, d, J=7.9 Hz, 2×ArH), 7.12-7.14 (1H, m, ArH), 7.21 (2H, d, J=8.8 Hz, 2×ArH), 7.26 (1H, s, ArH), 7.44-7.56 (2H, m, 2×ArH), 7.92 (2H, d, J=8.5 Hz, 2×ArH), 8.14 (1H, s, Ar H), 8.40 (1H, brs, exchangeable, NH). Anal. Calcd. for (C$_{21}$H$_{22}$Cl$_2$N$_4$O.H$_2$O): C, 57.94, H, 5.56, N, 12.87. Found: C, 58.27, H, 5.56, N, 12.6.

Example 8

1-{4-[Bis-(2-chloroethyl)amino]phenyl-3-[6-methoxy-2-(4-methoxyphenyl)quinolin-4-yl]urea (22, BO-1049)

1) Synthesis of 4-chloro-6-methoxy-2-(3-methoxyphenyl)quinoline

6-Methoxy-2-(3-methoxyphenyl)-1H-quinoline-4-one$^{44}$ (5.63 g, 20 mmol) was added to POCl$_3$ (11.6 g, 7 mL, 75 mmol) in a round flask at 0° C. with stirring. The homogenous suspension in the flask was then immersed into pre-heated at 80° C. oil bath and continuously heated until it solidified (about 15 min). The reaction mixture was cooled to room temperature and added to the mixture of ice (150 g), saturated NaHCO$_3$ aqueous solution (100 mL) and CH$_2$Cl$_2$ (100 mL). The organic layer was separated and the water layer was extracted with CH$_2$Cl$_2$ (2×10 mL). The combined extracts were dried over Na$_2$SO$_4$, filtered and concentrated in vacuo to dryness. The residue was crystallized from CHCl$_3$/hexane to give 6-methoxy-2-(3-methoxyphenyl)-4-chloro-quinoline, 5.94 g (99.0%), which was pure enough for using in next step. The analytic sample was prepared by recrystallization (CHCl$_3$/hexane); mp 106-107° C.; $^1$H NMR (CDCl$_3$) δ 3.93 and 3.99 (each: 3H, s, OCH$_3$), 7.00 (1H, dd, J=2.9, 8.1 Hz, ArH), 7.40-7.45 (3H, m, ArH), 7.64 (1H, d, J=8.1 Hz, ArH), 7.71 (1H, t, J=1.5 Hz, ArH), 7.92 (1H, s, ArH), 8.07 (1H, d, J=8.8 Hz, ArH). Anal. Calcd. for (C$_{17}$H$_{14}$Cl$_2$NO$_2$): C, 68.12; H, 4.71; N, 4.67. Found: C, 68.22; H, 4.34; N, 4.44.

2) Synthesis of 4-amino-6-methoxy-2-(3-methoxyphenyl)quinoline

A mixture of 6-methoxy-2-(3-methoxyphenyl)-4-chloroquinoline (5.90 g, 19.68 mmol) and phenol (20 g) was heated with stirring at 180° C. and ammonia was passed through the reaction mixture during 11 h. Phenol was then removed by steam distillation. The mixture was filtered and the filtrate was basified to pH 8 by adding 8% Na$_2$CO$_3$ aqueous solution. The solid formed was collected by filtration and dried to give the desired 4-amino-6-methoxy-2-(3-methoxyphenyl)quinoline, 5.313 g (96.3%); mp 148-149° C.; $^1$H NMR (DMSO-d$_6$) δ 3.85, 3.90 (each: 3H, s, OCH$_3$), 6.67 (2H, s, exchangeable, NH$_2$), 7.00 (1H, dd, J=2.9 and 8.1 Hz, ArH), 7.10 (1H, s, ArH), 7.28 (1H, dd, J=2.9 and 8.8 Hz, ArH), 7.40 (1H, t, J=8.1 Hz, ArH), 7.53 (1H, d, J=2.9 Hz, ArH), 7.61 (1H, 1H, d, J=8.1 Hz, ArH), 7.64 (1H, t, J=2.2 Hz, ArH), 7.77 (1H, d, J=8.8 Hz, ArH). Anal. Calcd. for (C$_{17}$H$_{16}$N$_2$O$_2$): C, 72.84; H, 5.75; N, 9.99. Found: C, 72.82; H, 5.51; N, 10.12.

3) Synthesis of 1-{4-[bis(2-chloroethyl)amino]phenyl-3-[6-methoxy-2-(4-methoxyphenyl)-quinolin-4-yl]urea (22, BO-1049)

A saturated aqueous NaHCO$_3$ solution was added slowly to a suspension of N,N-bis(2-chloroethyl)benzene-1,4-diamine dihydrochloride (37) (918 mg, 3.0 mmol) in dry toluene (30 mL) with stirring to neutralize to pH ~7. The organic and water layer were separated and the water layer was extracted with toluene (3×10 mL). The organic layer and extracts were combined, dried over Na$_2$SO$_4$, and then added dropwise to a stirred solution of trichlorimethylchloroformate (593 mg, 365 µL, 3.0 mmol) in dry toluene (10 mL) containing active carbon (20 mg) at 0° C. The reaction mixture was stirred at room temperature for 1 h and then refluxed for 30 min to form a clear solution, which was cooled, filtered through a pad of Celite. The filtrate was evaporated in vacuo to dryness to give crude bis(2-chloroethyl)-4-isocyanatophenylamine, 430 mg (39) (1.66 mmol). This intermediate was dissolved in anhydrous DMF (1 mL) and then added dropwise to a solution of 4-amino-6-methoxy-2-(3-methoxyphenyl) quinoline (280 mg, 1.0 mmol) in dry DMF (1 mL). The reaction mixture was stirred at 50° C. for 9 h and the solvent was removed by vacuum distillation. The residue was chromatographed on a silica gel column (2×24 cm) using CHCl$_3$/MeOH/(100:1 v/v) as eluent. The fractions containing the desired product were combined, evaporated and the solid residue was recrystallized from EtOH to give 1-{4-[bis(2-chloroethyl)amino]phenyl-3-[6-methoxy-2-(4-methoxyphenyl)quinolin-4-yl]urea (22, BO-1049); 400 mg (74.2%); mp 112-113° C.; $^1$H NMR (DMSO-d$_6$) δ3.72 (8H, m, 4×CH$_2$), 3.87 (3H, s, OMe), 4.01 (3H, s, OMe), 6.72 (2H, d, J=8.8 Hz, ArH), 7.07 (1H, dd, J=2.2 and 8.1 Hz, ArH), 7.41 (2H, d, J=8.8 Hz, 2×ArH), 7.47 (2H, m, 2×ArH), 7.65 (3H, m, ArH), 7.99 (2H, d, J=10.3 Hz, 2×ArH), 8.80 (1H, d, J=8.8 Hz, ArH), 9.25 (2H, brs, exchangeable, 2×NH). Anal. Calcd. for (C$_{28}$H$_{28}$Cl$_2$N$_4$O$_3$): C, 62.61; H, 5.23; N, 10.39. Found: C, 62.34; H, 4.99; N, 10.59.

Example 9

3-(3-{4-[Bis(2-chloroethyl)amino]phenyl}ureido)-N-(2-dimethylaminoethyl)benzamide hydrochloride (23, BO-1055)

1) Synthesis of N-(2-Dimethylaminoethyl)-3-nitrobenzamide

N,N-Dimethylethylendiamine (14.25 g, 61.0 mmol) was added dropwise into a solution of commercially available 3-nitrobenzoyl chloride (25.0 g, 134 mmol) in dry THF (150 mL) at 0° C. and stirred for 45 min. The reaction mixture was evaporated to under reduce pressure to dryness and residue was recrystallized from EtOH to give N-(2-dimethylaminoethyl)-3-nitrobenzamide; 31.0 g (97%); mp 89-90° C.; $^1$H NMR (CDCl$_3$) δ 2.29 (6H, s, 2×Me), 2.57 (2H, t, J=5.8 Hz, CH$_2$), 3.57 (2H, q, J=5.6 and 5.8 Hz, CH$_2$), 7.37 (1H, brs, exchangeable, NH), 7.63 (H, d, J=7.9 Hz, ArH) 8.19 (1H, m, ArH), 8.33 (1H, m, ArH), 8.66 (1H, s, ArH). Anal. Calcd. for ($C_{13}H_{21}N_3O_3$): C, 58.41, H, 7.92, N, 15.72. Found: C, 58.23, H, 7.69, N, 15.90.

2) Synthesis of 3-Amino-N-(2-dimethylaminoethyl)benzamide

To a solution of N-(2-dimethylaminoethyl)-3-nitrobenzamide (21.0 g, 88.0 mmol) in EtOH (50 mL) was added 10% Pd/C (2.52 g) and the hydrogenated with hydrogen at 35 psi for 3 h. The reaction mixture was filtered through a pad of Celite, the filtrate was evaporated to dryness and the solid obtained was recrystallize from EtOH to give 3-amino-N-(2-dimethylaminoethyl)benzamide; 17.19 g (93%); mp 97-100° C.; $^1$H NMR (CDCl$_3$) δ 2.20 (6H, s, 2×Me), 2.52 (2H, J=5.8 Hz, CH$_2$), 3.51 (2H, q, J=5.4 and 5.8 Hz, CH$_2$), 3.80 (2H, brs, exchangeable, NH$_2$), 6.75-6.80 (1H, m, ArH), 6.82 (1H, brs, exchangeable, NH), 7.10 (H, d, J=7.6 Hz, ArH) 7.12-7.30 (2H, m, ArH) 8.33 (1H, m, ArH), 8.66 (1H, s, ArH). Anal Calcd. for ($C_{11}H_{17}N_3O$): C, 63.74; H, 8.27; N 20.27. Found: C, 63.51, H, 8.45; N 20.12.

3) Synthesis of 3-(3-{4-[Bis(2-chloroethyl)amino]phenyl}ureido)-N-(2-dimethylaminoethyl)benzamide hydrochloride (23, BO-1055)

To a suspension of N,N-bis(2-chloroethyl)benzene-1,4-diamine hydrochloride (37, 0.918 g, 3 mmol) in dry toluene (35 mL) was added a saturated solution of NaHCO$_3$ to adjust pH 7-7.5. The organic layer was separated and the water layer was extracted with toluene (2×10 ml). The combined extracts were dried over anhydrous Na$_2$SO$_4$. To this solution was successively added charcoal (15 mg) and diphosgene (0.494 g, 2.5 mmol) in an ice-bath. The reaction mixture was stirred at room temperature for 30 min and then heated to reflux for 1 h to give a clear solution. After cooling, the mixture was filtered through a pad of Celite and the filtrate was evaporated in vacuo to dryness to give crude isocyante (39) as liquid. This was added dropwise into a solution of 3-amino-N-(2-dimethylaminoethyl)benzamide (0.400 g, 1.93 mmol) in dry DMF (25 mL) containing pyridine (2 mL) at −10° C. and then stirred at room temperature for 30 h. The solvent was removed under reduced pressure to dryness and the residue was dissolved in a mixture of CHCl$_3$/MeOH and silica gel (10 gm) and then evaporated in vacuo to dryness. The residue was put on the top of a silica gel column (30×4 cm) and chromotographed using CHCl$_3$/MeOH (100:1 v/v) as eluent. The fractions containing the main product were combined and evaporated in vacuo to dryness and the residue was dissolved in MeOH (15 mL) and then treated with 1.75 M HCl in MeOH (3 mL). The mixture was coevaporated several times with EtOH in vacuo to dryness and the residue was recrystallized from EtOH to give 3-(3-{4-[bis(2-chloroethyl)amino]phenyl}ureido)-N-(2-dimethylaminoethyl)benzamide hydrochloride (23, BO-1055), 0.90 g (81%); mp 139-141° C.; $^1$H NMR (DMSO-d$_6$) δ 1.19 (6H, s, NMe$_2$), 2.47 (2H, t, J=5.6 Hz, CH$_2$), 3.36 (2H, m, CH$_2$), 3.67-3.72 (8H, m, 4×CH$_2$), 6.71 (2H, d, J=9.0 Hz, 2×ArH), 7.28-7.39 (4H, m, ArH), 7.60 (1H, d, J=9.0 Hz, ArH), 7.85 (1H, s, Ar H), 8.33 (1H, s, exchangeable, NH), 8.62 (1H, s, exchangeable, NH), 8.93 (1H, s, exchangeable, NH), Anal. Calcld. for ($C_{22}H_{31}Cl_4N_5O_2.H_2O$): C, 47.40; H, 5.97; N, 12.57. Found: C, 47.77; H, 6.31; N, 11.30.

Example 10

[3-(Acridin-9-ylamino)-5-hydroxymethylphenyl]carbamic acid 4-[bis(2-chloro-ethyl)amino]phenyl ester ((24, BO-1062)

The known 4-[N,N-bis(2-chloroethyl)aminophenyl-4-nitrophenyl carbonate[39-41] (50, 1.12 g, 2.7 mmol) was added into a solution of 3-(acridin-9-ylamino)-5-hydroxy-methylaniline (AHMA)[18] (1.130 g, 2.73 mmol) in dry DMF (20 mL) containing pyridine (5 mL) at 0° C. After being stirred at room temperature for 21 h, the reaction mixture was evaporated under reduced pressure to dryness. The solid residue was triturated with acetone (15 mL) and filtered. The filtered cake was washed with acetone (10 mL) and then recrystallized from CHCl$_3$/MeOH (1:10) to give the desired [3-(acridin-9-ylamino)-5-hydroxymethylphenyl]carbamic acid 4-[bis(2-chloroethyl)amino]phenyl ester (24, BO-1062), 1.169 g (79%); mp 241-242° C.; $^1$H NMR (DMSO-d$_6$) δ3.72 (8H, s, 4×CH$_2$), 4.46 (2H, s, CH$_2$), 5.36 (1H, brs, exchangeable, OH), 6.74 (2H, d, J=9.0 Hz, 2×Ar H), 6.93-723 (3H, m, 3×Ar H), 7.40-7.73 (4H, m, 4×ArH), 7.93-8.05 (2H, m, ArH), 8.06-8.22 (2H, m, ArH), 8.23-8.46 (2H, m, ArH), 10.38 (1H, s, exchangeable, NH), 11.53 (1H, brs. exchangeable, NH). Anal. Calcld. for ($C_{31}H_{28}Cl_2N_4O_3.3H_2O$): C, 59.24; H, 5.42; N, 8.91. Found: C, 58.96; H, 5.08; N, 8.89.

Example 11

[3-Hydroxymethyl-5-(4-methylacridin-9-ylamino)phenyl]carbamic acid 4-[bis(2-chloroethyl)amino]phenyl ester (25, BO-1063)

4-[N,N-bis(2-chloroethyl)aminophenyl-4-nitrophenyl carbonate (50)[39-41] (1.1967 g, 3.0 mmol) was added into a solution of 3-amino-5-(4-methylacridin-9-ylamino)phenyl]methanol[33] (0.987, 3.0 mmol) in dry DMF (20 mL) containing pyridine (5 mL) at 0° C. for 1 h and then stirred at room temperature for 21 h. The reaction mixture was evaporated in vacuo to dryness and the solid was triturated with acetone (15 mL) and then filtered. The filtered cake was washed with acetone (5 mL) and the recrystallized from CHCl$_3$/MeOH (1:10) to give the resired [3-hydroxymethyl-5-(4-methylacridin-9-ylamino)phenyl]carbamic acid 4-[bis(2-chloroethyl)amino]phenyl ester (25, BO-1063), 1.053 g (61%); mp 229-231° C.; $^1$H NMR (DMSO-d$_6$) δ 2.81 (3H, s, Me), 3.72 (8H, s, 4×CH$_2$), 4.57 (2H, s, CH$_2$), 5.35 (1H, brs, exchangeable, OH), 6.74 (2H, d, J=9.0 Hz, 2×ArH), 6.98 (1H, s, ArH), 7.03 (2H, d, J=9.0 Hz, 2×ArH), 7.32-7.69 (4H, m, 4×ArH), 7.80-7.93 (1H, m, ArH), 7.96-8.11 (1H, m, ArH), 8.17-8.44 (2H, m, 2×ArH), 8.48-8.72 (1H, m, ArH), 10.37 (1H, brs, exchangeable, NH), 11.77 (1H, brs, exchangeable, NH). Anal. Calcld. for ($C_{32}H_{30}Cl_2N_4O_3.3H_2O$): C, 59.72; H, 5.64; N, 8.71. Found: C, 59.57; H, 5.34; N, 8.61.

Example 12

[2-Methyl-5-(4-methylacridin-9-ylamino)phenyl]carbamic acid 4-[bis(2-chloro-ethyl)amino]phenyl ester (26, BO-1064)

4-[N,N-bis(2-chloroethyl)aminophenyl4-nitrophenyl carbonate (50) (1.198 g, 3.0 mmol) was added portionwise into a solution of 4-methyl-N'1'-(4-methylacridin-9-yl)benzene-1,3-diamine[33] (0.940 g, 2.73 mmol) in dry DMF (20 mL) containing pyridine (5 ml) at room temperature. After being stirred for 36 h, the solvent was evaporated under reduced pressure and the residue was dissolved in a mixture of CHCl$_3$/MeOH containing silica gel (5 gm) and evaporated in vacuo to dryness. The residue was put on the top of a silica gel column (4×20 cm) and chromatographed by using CHCl$_3$/MeOH (100/1 v/v) as eluent. The fractions containing the main product were combined and evaporated in vacuo to dryness and the residue was recrystalized from CHCl$_3$/MeOH to give [2-methyl-5-(4-methylacridin-9-ylamino)phenyl]carbamic acid 4-[bis(2-chloroethyl)amino]phenyl ester (26, BO-1064);

0.905 g (52.5%); mp 154-156° C.; $^1$H NMR (DMSO-d$_6$) δ 2.36 (1H, s, Me), 2.81 (1H, s, Me), 3.71 (8H, s, 4×CH$_2$), 6.72 (2H, d, J=9.0 Hz, ArH), 6.94-7.07 (2H, m, ArH), 7.09-7.18 (1H, m, ArH), 7.28-7.52 (3H, m, ArH), 7.56-7.70 (1H, m, ArH), 7.79-7.90 (1H, m, ArH), 7.92-8.04 (1H, m, ArH), 8.18-8.34 (2H, m, ArH), 8.52-8.65 (1H, m, ArH), 9.52 (1H, s, exchangeable, NH), 11.65 (1H, brs, exchangeable, NH). Anal. Calcld. for (C$_{32}$H$_{30}$Cl$_2$N$_4$O$_2$.4.5H$_2$O): C, 58.73; H, 6.00; N, 8.56. Found: C, 58.57; H, 5.84; N, 8.62.

Example 13

[3-(Acridin-9-ylamino)-5-methoxyphenyl]carbamic acid 4-[bis(2-chloroethyl)-amino]phenyl ester (27, BO-1066)

4-[N,N-bis(2-chloroethyl)aminophenyl-4-nitrophenyl carbonate (50) (1.198 g, 3.0 mmol) was added protionwisw into a solution of N-acridin-9-yl-5-methoxybenzene-1,3-diamine[34] (0.945 g, 3.0 mmol) in dry DMF (20 mL) containing pyridine (5 mL) at room temperature. After being stirred for 56 h, the solvent was evaporated under reduced pressure and the residue was dissolved in a mixture of CHCl$_3$/MeOH containing silica gel (5 g) and evaporated in vacuo to dryness. The residue was put on the top of a silica gel column (4×20 cm) and chromatographed by using CHCl$_3$/MeOH (100/1 v/v) as eluent. The fractions containing the main product were combined and evaporated in vacuo to dryness and the residue recrystalize from CHCl$_3$/MeOH to give [3-(acridin-9-ylamino)-5-methoxyphenyl]carbamic acid 4-[bis(2-chloroethyl)amino]phenyl ester (27, BO-1066); 0.317 g (21%); mp 179-180° C.; $^1$H NMR (DMSO-d$_6$) δ 3.34 (3H, s, Me), 3.71 (8H, s, 4×CH$_2$), 6.08-6.16 (1H, m, ArH), 6.51-6.61 (1H, m, ArH), 6.74 (2H, d, J=9.0 Hz, ArH) 6.85-6.93 (1H, m, ArH), 7.02 (2H, d, J=9.0 Hz, ArH), 7.04-7.17 (H, m, ArH), 7.36-7.66 (4H, m, ArH), 7.77-8.14 (2H, m, ArH), 10.05 (1H, s, exchangeable, NH), 11.23 (1H, brs, exchangeable, NH). Anal. Calcld. for (C$_{31}$H$_{28}$Cl$_2$N$_4$O$_3$.0.5H$_2$O): C, 63.70; H, 5.00; N, 9.59. Found: C, 63.62; H, 5.03; N, 9.51.

Example 14

(3-(Acridin-9-ylamino)-5-{4-[bis(2-chloroethyl) amino]phenylcarbamoyloxymethyl}-phenyl)carbamic acid ethyl ester (28, BO-1054)

To a suspension of N,N-bis(2-chloroethyl)benzene-1,4-diamine hydrochloride (37) (0.918 g, 3.0 mmol) and charcoal (20 mg) in dry dioxane (30 mL) was added diphosgene (0.494 g, 2.5 mmol) and heated at 90-95° C. for 5 h. The reaction mixture was filtered through a pad of Celite and the filtrate containing crude 39 was added dropwise into a solution of [3-(acridin-9-ylamino)-5-hydroxymethyl-phenyl]carbamic acid ethyl ester[52] (0.988 g, 2.5 mmol) in dry DMF (25 mL) containing pyridine (2 mL) at −10° C. The reaction mixture was allowed to stir at room temperature for 24 h. The mixture was then evaporated in vacuo to dryness and the residue was dissolved in a mixture of CHCl$_3$/MeOH containing silica gel (10 g) and then evaporated in vacuo to dryness. The residue was put on the top of a silica gel column (4×30 cm) and chromatographed using CHCl$_3$/MeOH (100:3 v/v) as eluent. The fractions containing the main product were combined and evaporated in vacuo to dryness and the residue was recrystallized from CHCl$_3$/MeOH to give (3-(acridin-9-ylamino)-5-{4-[bis(2-chloroethyl)amino] phenylcarbamoyloxymethyl}phenyl)carbamic acid ethyl ester (28, BO-1054), 0.185 g (10.0%); mp 178-182° C.; $^1$H NMR (DMSO-d$_6$) δ 1.21 (3H, t, J=7.0 Hz, Me), 3.68 (8H, m, 4×CH$_2$), 4.08 (2H, q, J=7.0 Hz, CH$_2$), 5.02 (2H, s, CH$_2$), 6.65 (2H, d, J=9.0 Hz, ArH) 6.81-7.35 (6H, m, ArH), 7.39-7.95 (4H, m, ArH), 7.98-8.83 (3H, m, ArH), 9.36 (1H, brs, exchangeable, NH), 9.69 (2H, brs, exchangeable, NH). Anal. Calcld. for (C$_{34}$H$_{33}$Cl$_2$N$_5$O$_4$): C, 63.16; H, 5.14; N, 10.83. Found: C, 62.93; H, 5.04; N, 10.58.

Example 15

Carbonic acid 3-(acridin-9-ylamino)-5-ethoxycarbonylaminobenzyl ester 4-[bis(2-chloroethyl)amino] phenyl ester (29, BO-1065)

4-[N,N-bis(2-chloroethyl)aminophenyl-4-nitrophenyl carbonate[39-41] (50) (0.800 g, 2.0 mmol) was added portionwise into a solution of [3-(acridin-9-ylamino)-5-hydroxymethylphenyl]carbamic acid ethyl ester[52] (0.774 g, 2.0 mmol) in dry DMF (10 mL) containing pyridine (4 mL) at room temperature. After being stirred for 40 h, the solvent was evaporated under reduced pressure and the residue was dissolved in a mixture of CHCl$_3$/MeOH containing silica gel (5 g) and then evaporated in vacuo to dryness. The residue was put on the top of a silica gel column (4×20 cm) and chromatographed by using CHCl$_3$/MeOH (100/1 v/v) as eluent. The fractions containing the main product were combined and evaporated in vacuo to dryness and the residue recrystalized from CHCl$_3$/MeOH to give carbonic acid 3-(acridin-9-ylamino)-5-ethoxycarbonylaminobenzyl ester 4-[bis(2-chloroethyl)amino]phenyl ester (29, BO-1065); 0.719 g (55.7%); mp 131-133° C.; $^1$H NMR (DMSO-d$_6$) δ 1.22 (3H, t, J=9.0 Hz, Me), 3.71 (8H, s, 4×CH$_2$), 4.09 (2H, q, J=9.0 Hz, CH$_2$,), 5.13 (1H, s, CH$_2$), 6.43-6.62 (1H, m, ArH) 6.73 (2H, d, J=9.0 Hz, ArH), 6.68-7.19 (5H, m, ArH), 7.21-7.19 (1H, m, ArH), 7.38-7.72 (4H, m, ArH), 7.75-8.39 (2H, m, ArH), 9.66 (1H, s, exchangeable, NH), 11.17 (1H, brs, exchangeable, NH). Anal. Calcld. for (C$_{34}$H$_{32}$Cl$_2$N$_4$O$_5$.0.5H$_2$O): C, 62.20; H, 5.07; N, 8.53. Found: C, 62.29; H, 5.07; N, 8.52.

Example 16

N-{4-[Bis(2-chloroethyl)amino]phenyl}-2-(2-methyl-4-quinolinyl)hydrazinecarboxamide (30, BO-1233)

1) Synthesis of 4-chloro-2-methylquinoline

The commercially available 4-hydroxy-2-methylquinoline (6.522 g, 41 mmol) was added portionwise to POCl$_3$ (35 mL) in a round flask at 0° C. with stirring. The homogenous suspension was then immersed into a pre-heated at 80° C. oil bath and continuously refluxed for 4 h. The reaction mixture was cooled to room temperature and the excess POCl$_3$ was distilled out under reduces pressure. The residue was treated carefully with ice (150 g) and then with saturated NaHCO$_3$ aqueous solution (200 mL). The mixture was extracted with CH$_2$Cl$_2$ (100×3 mL), dried over Na$_2$SO$_4$, and evaporated in vacuo to dryness to give known 4-chloro-2-methylquinoline,[53] 6.10 g (84.14%) as oil, which was pure enough for using in next step. $^1$H NMR (DMSO) δ 2.61 (3H, s, Me), 7.66 (1H, s, ArH), 7.67-7.71 (1H, m, ArH), 7.82-7.85 (1H, s, ArH), 8.01 (1H, d, J=6.7 Hz, ArH), 8.12-8.14 (1H, s, ArH). Anal. Calcd. for (C$_{10}$H$_8$ClN): C, 67.62; H, 4.54; N, 7.89. Found: C, 67.62; H, 4.54; N, 7.89.

2) Synthesis of 4-hydrazino-2-methylquinoline

A solution of 4-chloro-2-methylquinoline (5.01 g, 28.2 mmol) and 80% hydrazine hydrate (8 ml) solution was refluxed in ethanol (30 mL) for 8 h. The resulting solution was cooled to room temperature and the solid formed was collected by filtration, washed with ethanol, and dried to yield known 4-hydrazino-2-methylquinoline,[54,55] 4.712 g (79.70%); mp 195-197° C.; $^1$H NMR (DMSO-$d_6$) δ 2.64 (3H, s, Me), 5.15 (2H, brs, exchangeable, $NH_2$), 6.99 (1H, s, ArH), 7.58 (1H, t, J=7.6 Hz, ArH), 7.86 (1H, t, J=7.6 Hz, ArH), 7.85 (1H, d, J=8.4 Hz, ArH), 8.42 (1H, d, J=8.2 Hz, ArH), 10.64 (1H, s, exchangeable, NH), Anal. Calcd. for ($C_{10}H_{12}N_3$.HCl): C, 57.28; H, 5.77; N, 20.04. Found: C, 57.28; H, 5.77; N, 20.04.

3) Synthesis of N-{4-[bis(2-chloroethyl)amino]phenyl}-2-(2-methyl-4-quinolinyl)-hydrazinecarboxamide (30, BO-1233)

To a suspension of N,N-bis(2-chloroethyl)benzene-1,4-diamine hydrochloride (37, 2.524 g, 8.25 mmol) in dry $CHCl_3$ (20 mL), $Et_3N$ (2.5 mL) was added dropwise at −5-0° C. The resulting solution was added dropwise to a solution of triphosgene (0.673 g, 3.21 mmol) in dry $CHCl_3$ (15 mL) at −5-0° C. The reaction mixture was stirred at room temperature for 30 min. The resulting solution was evaporated under reduced pressure to dryness to give crude isocynate (39) as liquide. This solution was added dropwise into a suspension of 4-hydrazino-2-methylquinoline (1.053 g, 5 mmol) in dry DMF (40 mL) containing $Et_3N$ (4 mL) at 0° C. The reacting mixture was stirred at room temperature for 1.5 h. The resulting solution was evaporated under reduced pressure to dryness. The solid residue was triturated with a mixture of THF/ether (2:1 v/v) and the solid was collected by filtration, washed with little amount of cold chloroform and methanol, and dried to give N-{4-[bis(2-chloroethyl)amino]phenyl}-2-(2-methyl-4-quinolinyl)hydrazinecarboxamide (30, BO-1233), 2.05 g (94.47%); mp 235-236° C.; $^1$H NMR (DMSO-$d_6$) δ 2.71 (3H, s, Me), 3.68-3.71 (8H, m, 4×$CH_2$), 6.70 (2H, d, J=9.0 Hz, ArH), 6.89 (1H, s, ArH), 7.31 (2H, d, J=9.0 Hz, ArH), 7.72 (1H, t, J=7.7 Hz, ArH), 7.97 (1H, t, J=7.1 Hz, ArH), 8.03 (1H, d, J=8.5 Hz, ArH), 8.49 (1H, d, J=8.5 Hz, ArH), 9.04 and 9.12 (each 1H, s, exchangeable, 2×NH), 10.84 (1H, brs, exchangeable, NH). Anal. Calcd. for ($C_{21}H_{23}Cl_2N_5O$): C, 58.34; H, 5.36; N, 16.20. Found: C, 58.50; H, 5.37; N, 16.40.

Example 17

N-{4-[Bis(2-chloroethyl)amino]phenyl}-2-(6-methoxy-2-methyl-4-quinolinyl)hydrazinecarboxamide (31, BO-1228)

To a suspension of N,N-bis(2-chloroethyl)benzene-1,4-diamine hydrochloride (37, 0.826 g, 2.7 mmol) in dry $CHCl_3$ (10 mL), $Et_3N$ (1.5 mL) was added dropwise at −5-0° C. The resulting solution was added dropwise to a solution of triphosgene (0.296 g, 1 mmol) in dry $CHCl_3$ (10 mL) at −5-0° C. The reaction mixture was stirred at room temperature for 30 min. The resulting solution was evaporated under reduced pressure to dryness to give crude isocynate (39) as liquide. This solution was added dropwise into a suspension of known 4-hydrazino-6-methoxy-2-methylquinoline (0.36 g, 1.5 mmol)[56,57] and $Et_3N$ (2 mL) in dry DMF (15 mL at 0° C. The reacting mixture was stirred at room temperature for 1.5 h. The resulting solution was evaporated under reduced pressure to dryness. The solid residue was triturated with a mixture of THF/ether (2:1 v/v) and the solid was collected by filtration, washed with little amount of cold chloroform and methanol, and dried to give N-{4-[bis(2-chloroethyl)amino]phenyl}-2-(6-methoxy-2-methyl-4-quinolinyl)hydrazinecarboxamide (31, BO-1228), 0.413 g (60%): mp 224-225° C.; $^1$H NMR (DMSO-$d_6$) δ 2.68 (3H, s, Me), 3.68-3.70 (8H, m, 4×$CH_2$), 3.94 (3H, s, OMe), 6.70 (2H, d, J=9.0 Hz, ArH), 6.84 (1H, s, ArH), 7.31 (2H, d, J=9.0 Hz, ArH), 7.61 (1H, dd, J=2.2 and 9.2 Hz, ArH), 7.91 (1H, d, J=2.2 Hz, ArH), 7.96 (1H, d, J=9.2 Hz, ArH), 9.01 and 9.11 (each 1H, s, exchangeable, 2×NH), 10.65 (1H, brs, exchangeable, NH). Anal. Calcld. for ($C_{22}H_{25}Cl_2N_5O_2$): C, 57.14; H, 5.45; N, 15.15. Found: C, 57.40; H, 5.18; N, 15.52.

Example 18

N-{4-[Bis(2-chloroethyl)amino]phenyl}-N'-{4-[(6-methyl[1,3]dioxolo[4,5-g]quinolin-8-yl)oxy]phenyl}urea (32, BO-1262)

1) Synthesis of 6-methyl-8-(4-nitrophenoxy)[1,3]dioxolo[4,5-g]quinoline

A mixture of known 8-chloro-6-methyl[1,3]dioxolo[4,5-g]quinoline (2.216 g, 10 mmol)[56] and 4-nitrophenol (2.08 g, 15 mmole) was heated at 140-150° C. for 2 h. The resulting solution was dissolved in chloroform and washed with 10% aq. solution of NaOH and brine. The organic layer was dried over anhydrous $Na_2SO_4$ and concentrated under reduce pressure. The resulting solid was collected by filtration, washed with ether and dried to 6-methyl-8-(4-nitrophenoxy)[1,3]dioxolo[4,5-g]quinoline, 2.94 g of (90.60%); mp 210-212° C.; $^1$H NMR (DMSO-$d_6$) δ 2.52 (3H, s, Me), 6.21 (2H, s, $CH_2$), 6.86 (1H, s, ArH), 7.30 (1H, s, ArH), 7.34-7.38 (3H, m, ArH), 8.29-8.33 (2H, m, ArH). Anal. Calcld. for ($C_{17}H_{12}N_2O_5$): C, 62.96; H, 3.73; N, 8.64. Found: C, 62.27; H, 3.84; N, 8.58.

2) Synthesis of 4-[(6-methyl[1,3]dioxolo[4,5-g]quinolin-8-yl)oxy]phenylamine A mixture of 6-methyl-8-(4-nitrophenoxy)[1,3]dioxolo[4,5-g]quinoline (2.0 g, 6.18 mmol) in dioxane (100 mL) and 10% Pd/C (500 mg) was hydrogenated for 7 h at 35 psi. The reaction mixture was filtered through a pad of Celite and the filter cake was washed with dioxan. The combined filtrate and washings was evaporated in vacuo to dryness. The solid residue recrystallized from $CHCl_3$ to yield 4-[(6-methyl[1,3]dioxolo-[4,5-g]quinolin-8-yl)oxy]phenylamine, 1.680 g (92.43%); mp 251-253° C.; $^1$H NMR (DMSO-$d_6$) δ 2.43 (3H, s, Me), 5.56 (2H, brs, exchangeable, $NH_2$), 6.21 (2H, s, $CH_2$), 6.32 (1H, s, ArH), 6.66 (2H, d, J=8.6 Hz, ArH), 6.90 (2H, d, J=8.6 Hz, ArH), 7.28 (1H, s, ArH), 7.49 (1H, s, ArH). Anal. Calcld. for ($C_{17}H_{14}N_2O_3$): C, 69.38; H, 4.79; N, 9.25. Found: C, 69.57; H, 4.88; N, 9.32.

3) Synthesis of N-{4-[bis(2-chloroethyl)amino]phenyl}-N'-{4-[(6-methyl[1,3]dioxolo[4,5-g]-quinolin-8-yl)oxy]phenyl}urea (32, BO-1262)

To a suspension of N,N-bis(2-chloroethyl)benzene-1,4-diamine hydrochloride (37, 1.101 g, 3.6 mmol) in dry $CHCl_3$ (10 mL), $Et_3N$ (1.5 mL) was added dropwise at −5-0° C. The resulting solution was added dropwise to a solution of triphosgene (0.415 g, 1.4 mmol) in dry $CHCl_3$ (10 mL) at −5-0° C. The reaction mixture was stirred at room temperature for 30 min. The resulting solution was evaporated under reduced pressure to dryness to give crude isocynate (39), which was dissolved in dry DMF (2 mL). To this solution was added dropwise a solution of 4-[(6-methyl[1,3]-dioxolo[4,5-g]quinolin-8-yl)oxy]phenylamine (0.589 g, 2 mmol) in dry DMF (10 mL) containing $Et_3N$ (1.5 mL) at room temperature and then stirred for 5 h. The resulting solution was evaporated under reduced pressure to dryness and the solid residue was chromatographed on a silica gel column (3×35 cm) using CHCl$_3$ as the eluent. The main fractions containing the desired product were combined and concentrated under reduced pressure. The resulting solid was collected by filtration, and recrystallized from CHCl$_3$ to yield N-{4-[bis(2-chloroethyl)amino]phenyl}-N'-{4-[(6-methyl[1,3]dioxolo[4,5-g]-quinolin-8-yl)oxy]phenyl}urea (32, BO-1262); 0.556 g (50.2%): mp 217-218° C.; $^1$H NMR (DMSO-d$_6$) δ 2.43 (3H, s, Me), 3.70 (8H, s, 4×CH$_2$), 6.20 (2H, s, CH$_2$,), 6.36 (1H, s, ArH), 6.72 (2H, d, J=8.52 Hz, ArH), 7.14 (2H, d, J=8.76 Hz, ArH), 7.27-7.30 (3H, m, ArH), 7.48 (1H, s, ArH), 7.55 (2H, d, J=8.60 Hz, ArH), 8.39 (1H, s, exchangeable, NH), 8.69 (1H, s, exchangeable, NH). Anal. Calcld. for (C$_{28}$H$_{26}$Cl$_2$N$_4$O$_4$): C, 60.77; H, 4.74; N, 10.12. Found: C, 60.55; H, 4.76; N, 10.32.

Example 19

4-[Bis(2-chloroethyl)amino]phenyl 4-[(6-methyl[1,3]dioxolo[4,5-g]quinolin-8-yl)-oxy]phenylcarbamate (33, BO-1263)

A mixture of 4-[N,N-bis(2-chloroethyl)aminophenyl-4-nitrophenyl carbonate (50)$^{39-41}$ (0.590 g, 1.5 mmol) and 4-[(6-methyl[1,3]dioxolo[4,5-g]quinolin-8-yl)oxy]-phenylamine (0.294 g, 1 mmol) in pyridine was stirred overnight at room temperature and then evaporated in vacuo to dryness. The solid product was purified by column chromatography on a silica gel column (3×35 cm) using CHCl$_3$ as the eluent. The main fractions containing the desired product was combined and concentrated under reduced pressure to dryness and the solid residue was recrystallized from CHCl$_3$ to afford 4-[bis(2-chloroethyl)amino]phenyl-4-[(6-methyl[1,3]dioxolo[4,5-g]quinolin-8-yl)oxy]phenylcarbamate (33, BO-1263); 0.372 g (67.23%): mp 183-184° C.; $^1$H NMR (DMSO-d$_6$) δ 2.43 (3H, s, Me), 3.74 (8H, s, 4×CH$_2$), 6.20 (2H, s, CH$_2$,), 6.77 (2H, d, J=9.12 Hz, ArH) 6.77 (2H, d, J=9.08 Hz, ArH), 7.20 (1H, d, J=8.92 Hz, ArH), 7.28 (1H, s, ArH), 7.47 (1H, s, ArH), 7.61 (2H, d, J=8.92 Hz, ArH), 10.20 (1H, s, exchangeable, NH). Anal. Calcld. for (C$_{28}$H$_{25}$Cl$_2$N$_3$O$_5$): C, 60.66; H, 4.55; N, 7.58. Found: C, 60.39; H, 4.67; N, 7.52.

Example 20

Biological Results

Our molecular design and organic synthesis in conjunction with the pharmacological findings have led to a series of new compounds that are found to possess potent antitumor activities in vitro and cancer therapeutic effect in vivo. These compounds, a series of aniline (or phenol) N-mustards linked to DNA-affinity carriers either by a urea or carbamic acid linkage, are found to efficaciously against various types of tumors including leukemic and solid tumors, as well as brain tumors, parent and drug-resistant tumors and/or tumor cells. The newly synthesized compounds have been investigated in tissue culture systems as well as in the immunodeficient nude mice bearing human tumors for the therapeutic efficacy and their associated toxicity if occurred. The in vivo therapeutic methods include specific doses, schedules, routes and intervals of drug administration and also include the evaluation of therapeutic efficacy and toxicity at tolerable dose ranges or optimal therapeutic conditions.

The following specific compounds in accordance with the present invention were synthesized for antitumor evaluation:

9-Anilinoacridine-N-mustard conjugates bearing a urea spacer

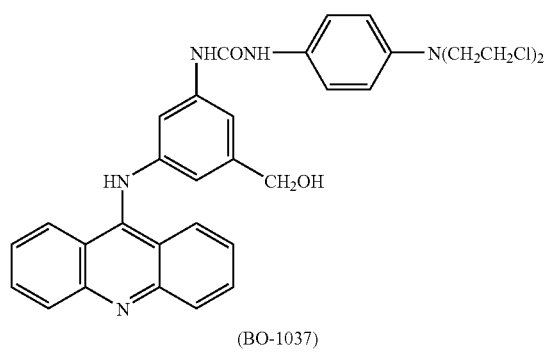
(BO-1037)

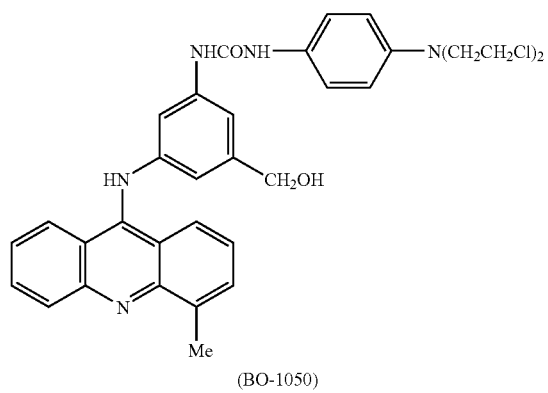
(BO-1050)

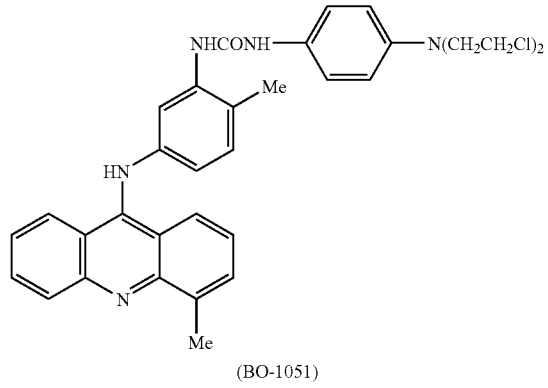
(BO-1051)

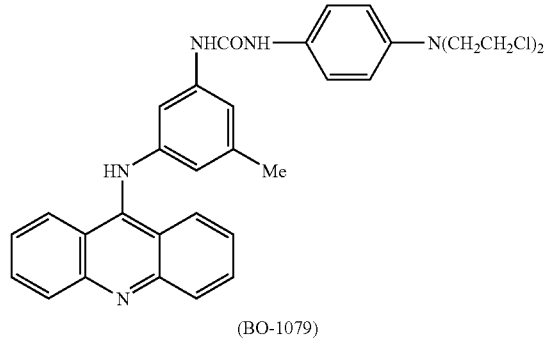
(BO-1079)

-continued
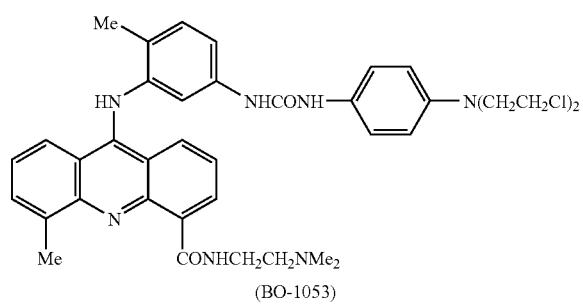
(BO-1053)
Acridine-N-mustard conjugates bearing a urea spacer
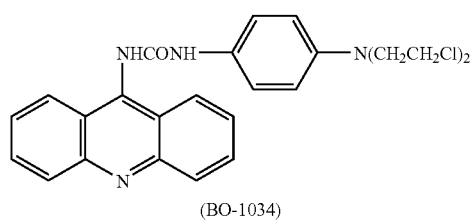
(BO-1034)
Quinoline-N-mustard conjugates bearing a urea spacer
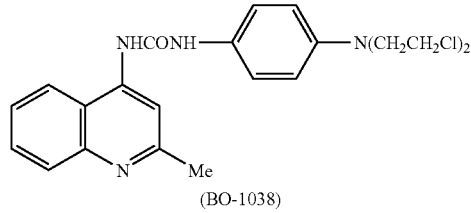
(BO-1038)
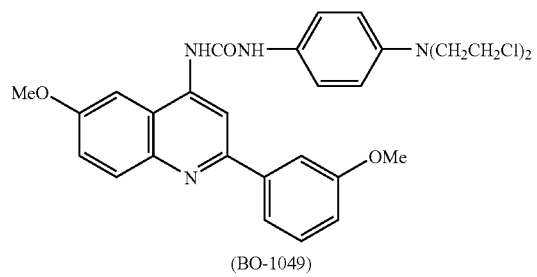
(BO-1049)
Water-soluble N-mustard derivatives bearing a urea spacer
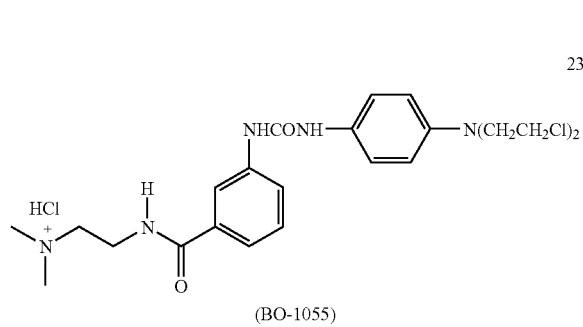
(BO-1055)
9-Anilinoacridine-N-mustard conjugates bearing a carbamic acid ester spacer
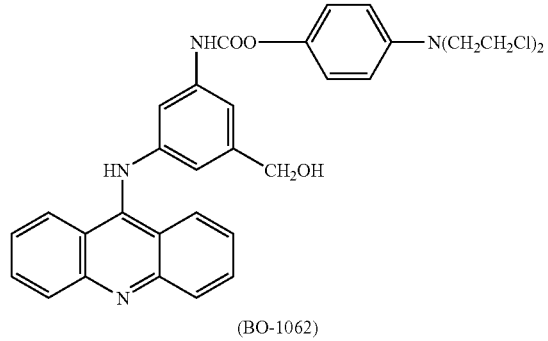
(BO-1062)
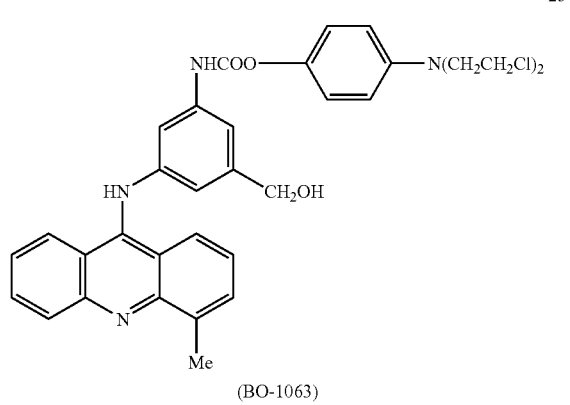
(BO-1063)
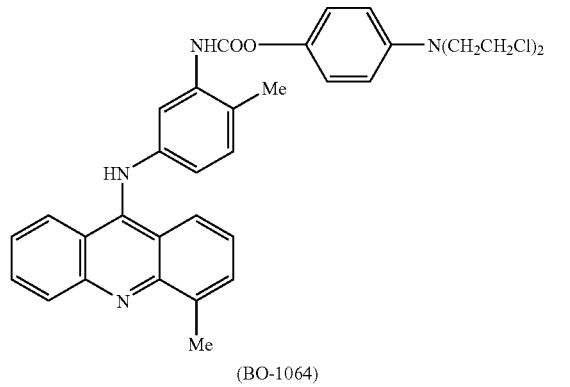
(BO-1064)
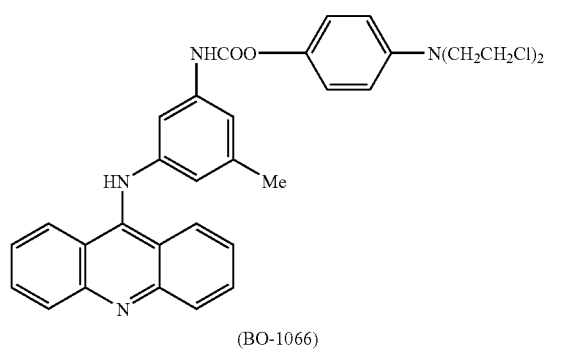
(BO-1066)

43
-continued

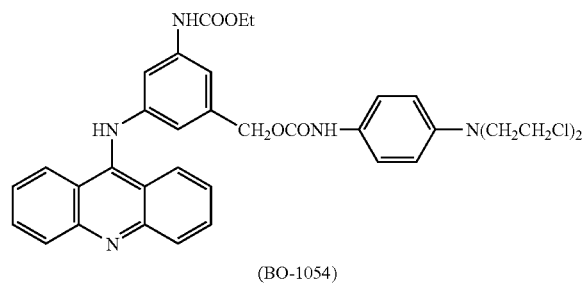

(BO-1054)

9-Anilinoacridine-N-mustard conjugates bearing a carbonic acid ester spacer

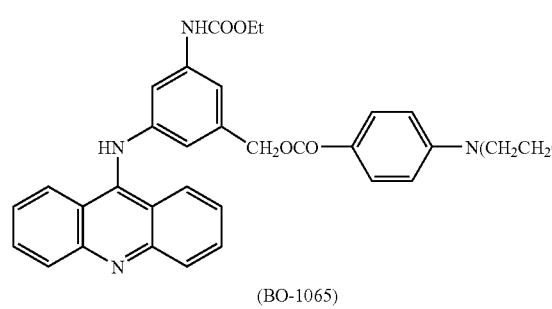

(BO-1065)

Quinoline-N-mustard conjugates bearing a hydrazineurea spacer

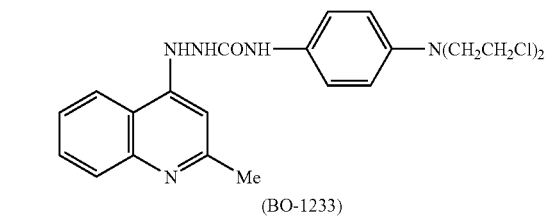

(BO-1233)

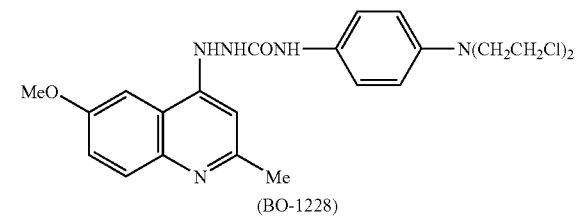

(BO-1228)

44

Quinoline-N-mustard conjugates bearing a phenoxyurea and phenoxycarbamic acid ester spacer (BO-1263)

(BO-1262)

As shown below, the preliminary results showed that these compounds exhibited significant cytotoxicity in inhibiting various human tumor cell growth in vitro and possessed potent therapeutic efficacy in animal bearing human tumor xenografts (such as human breast carcinoma MX-1 and neuroblastoma U87). The results demonstrated the newly invented compounds possess potent antitumor therapeutic efficacy and have potential for clinical application.

Figure 2:
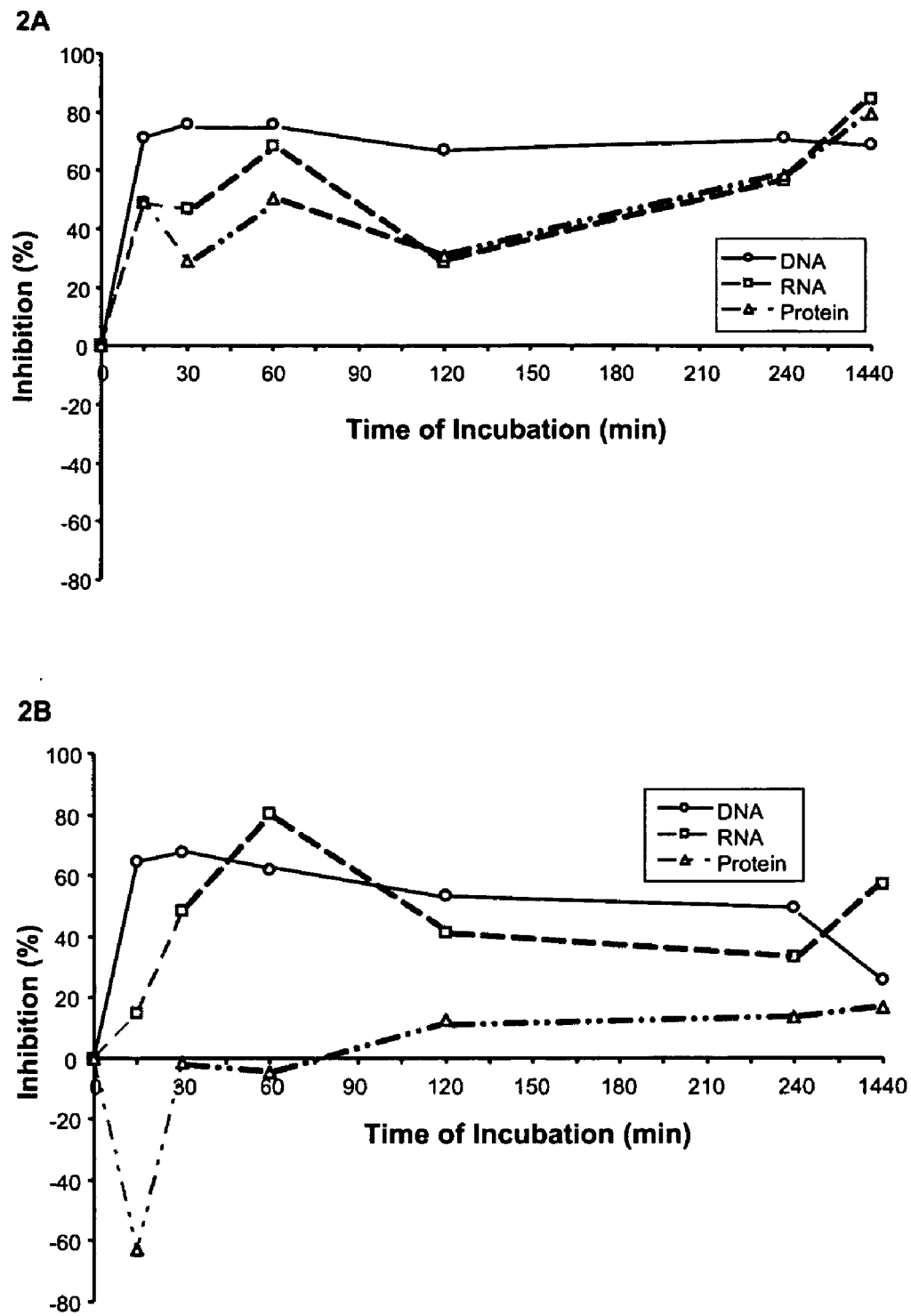
FIG. 2 illustrates inhibition of biosynthesis of DNA, RNA and protein by representative new compounds, BO-1038 (FIG. 2A) and BO-1051 (FIG. 2B) at the concentration of 10 µM.

The representative biological results are given in Table 1 and FIG. 2 for the in vitro findings and the in vivo results are in FIGS. 3A, 3B, 4A, 4B, 5A and 5B. The specific materials and methods used are also given.

In Vitro Cytotoxicity.

Table 1 shows the potency of inhibiting tumor cell growth by the newly synthesized derivatives in vitro. The $IC_{50}$ is defined by the concentration required to inhibit tumor cell growth by 50%. It demonstrated that these agents exhibited potent cytotoxicity against human lymphoblastic leukemis (CCRF/CEM) as well as the solid tumors (mammary MX-1 and colon HCT-116) cell growth in vitro with submicromolar $IC_{50}$ values. The growth inhibition against human lymphoblastic leukemic cells (CCRF-CEM) and its drug-resistant sublines (resistant to vinblastine and taxol, CCRF-CEM/VBL and CCRF-CEM/taxol, respectively) by the newly synthesized was also indicated in Table 1. The results revealed that these compounds have little or no cross-resistance to either taxol or vinblastine. With one exception, BO-1037 was cross-resistant to these two antitumor agents. It suggested that most N-mustard derivatives were neither a good substrate of membrane of p-glycoprotein nor mutated tubulin.

TABLE 1

Potency of presentive N-mustards against CCRF-CEM leukemic sublines, MX-1 and HCT-116 solid tumor cell growth in vitro.

| | | $IC_{50}$ (μM)[a] | | | |
|---|---|---|---|---|---|
| Compound | CCRF-CEM | CCRF-CEM/Taxol[b] | CCRF-CEM/VBL[b] | MX-1 | HCT-116 |
| 15 BO-1037 | 0.0545 | 16.91[308x][c] | 61.35[1115x] | 0.388 | 0.215 |
| 16 BO-1050 | 0.030 | 0.384[12.8x] | 1.320[4.4x] | 0.128 | 0.269 |

TABLE 1-continued

Potency of presentive N-mustards against CCRF-CEM leukemic sublines, MX-1 and HCT-116 solid tumor cell growth in vitro.

| | $IC_{50}$ (μM)[a] | | | | |
|---|---|---|---|---|---|
| Compound | CCRF-CEM | CCRF-CEM/Taxol[b] | CCRF-CEM/VBL[b] | MX-1 | HCT-116 |
| 17 BO-1051 | 0.074 | $0.092_{[1.2x]}$ | $0.131_{[1.8x]}$ | 0.174 | 0.439 |
| 18 BO-1079 | 0.136 | $0.380_{[2.8x]}$ | $0.598_{[4.4x]}$ | 0.498 | 0.799 |
| 19 BO-1053 | 0.012 | $0.184_{[15.3x]}$ | $0.304_{[25.3x]}$ | 0.059 | 0.057 |
| 20 BO-1034 | 0.198 | $0.418_{[2.1x]}$ | $0.392_{[2.0x]}$ | 0.845 | 0.888 |
| 21 BO-1038 | 0.189 | $0.420_{[2.2x]}$ | $0.650_{[3.4x]}$ | 0.351 | 1.245 |
| 22 BO-1049 | 0.366 | $0.587_{[1.6x]}$ | $0.551_{[1.5x]}$ | 1.841 | 3.745 |
| 23 BO-1055 | 0.127 | $1.195_{[15.4x]}$ | $0.791_{[6.2x]}$ | 0.551 | 0.661 |
| 24 BO-1062 | 0.057 | $0.112_{[2.0x]}$ | $0.194_{[3.4x]}$ | 0.096 | 0.563 |
| 25 BO-1063 | 0.075 | $0.081_{[1.1x]}$ | $0.134_{[1.8x]}$ | 0.081 | 0.450 |
| 26 BO-1064 | 0.116 | $0.158_{[1.4x]}$ | $0.146_{[1.3x]}$ | 0.280 | 0.589 |
| 27 BO-1066 | 0.206 | $0.306_{[1.5x]}$ | $0.107_{[0.52x]}$ | 0.342 | 1.705 |
| 28 BO-1054 | 0.084 | $0.242_{[2.9x]}$ | $0.324_{[3.9x]}$ | 0.605 | 0.757 |
| 29 BO-1065 | 0.313 | $0.505_{[1.6x]}$ | $0.478_{[1.5x]}$ | 0.089 | 0.636 |
| Taxol | 0.0013 ± 0.0001 | $0.429 ± 0.042_{[330x]}$ | $1.274 ± 0.052_{[980x]}$ | 0.035 ± 0.014 | 0.0013 ± 0.0002 |
| Vinblastine | 0.00073 ± 0.00009 | $0.078 ± 0.011_{[106.2x]}$ | $0.496 ± 0.121_{[679.5x]}$ | 0.0029 ± 0.0005 | 0.0018 ± 0.0004 |

[a] Cell growth inhibition was measured by the XTT assay[57] for leukemic cells and the SRB assay[58] for solid tumor cells after 72-hr incubation using a microplate spectrophotometer as described previously.[59] $IC_{50}$ values were determined from dose-effect relationship at six or seven concentrations of each drug by using the CompuSyn software by Chou and Martin[60] based on the median-effect principle and plot.[61,62] Ranges given for Taxol and Vinblastine were mean ± SE (n = 4).
[b] CCRF-CEM/Taxol and CCRF-CEM/VBL are subcell lines of CCRF-CEM cells that are 330-fold resistant to Taxol, and 680-fold resistant to Vinblastine, respectively, when comparing with the $IC_{50}$ of the parent cell line.
[c] Numbers in the brackets are fold of cross-resistant determined by comparison with the corresponding $IC_{50}$ of the parent cell line.

FIG. 2 shows the time course of inhibition of biosynthesis of DNA, RNA and protein by representative new compounds, BO-1038 and BO-1501. [³H]Thymidine (1 uCi), [³H]adenosine (1 μCi) and [³H]leucine (2 μCi) were used as the tracers for incorporation into DNA, RNA and protein, respectively. Each 1 mL incubation mixture contained 5.2×105 MX-1 cells, and 10 μM or 10 μM of BO-1038 or BO-1051, respectively. Incubation was terminated at each time points as indicated. For details of the method see Chou et al. Cancer Research 43: 3074-3079, 1983. As shown in FIG. 2, the degrees of inhibiting biosynthesis of DNA and RNA for both compounds were maximized at 50-80%. The half-maximal inhibition was reached within 15-30 min and persisted for over 6-24 hrs. The protein synthesis inhibition by BO-1038 was at similar degree as RNA synthesis inhibition which ranged 40-80% inhibition. However, the protein synthesis inhibition by BO-1051 was less than 20%, and there was an initial activation within the first 30 min followed by the moderate inhibition of about 20%. The degrees of inhibiting DNA and RNA biosynthesis by BO-1051 were similar except there was a delay in reaching maximal effect for about 1 hr.

Figure 5:
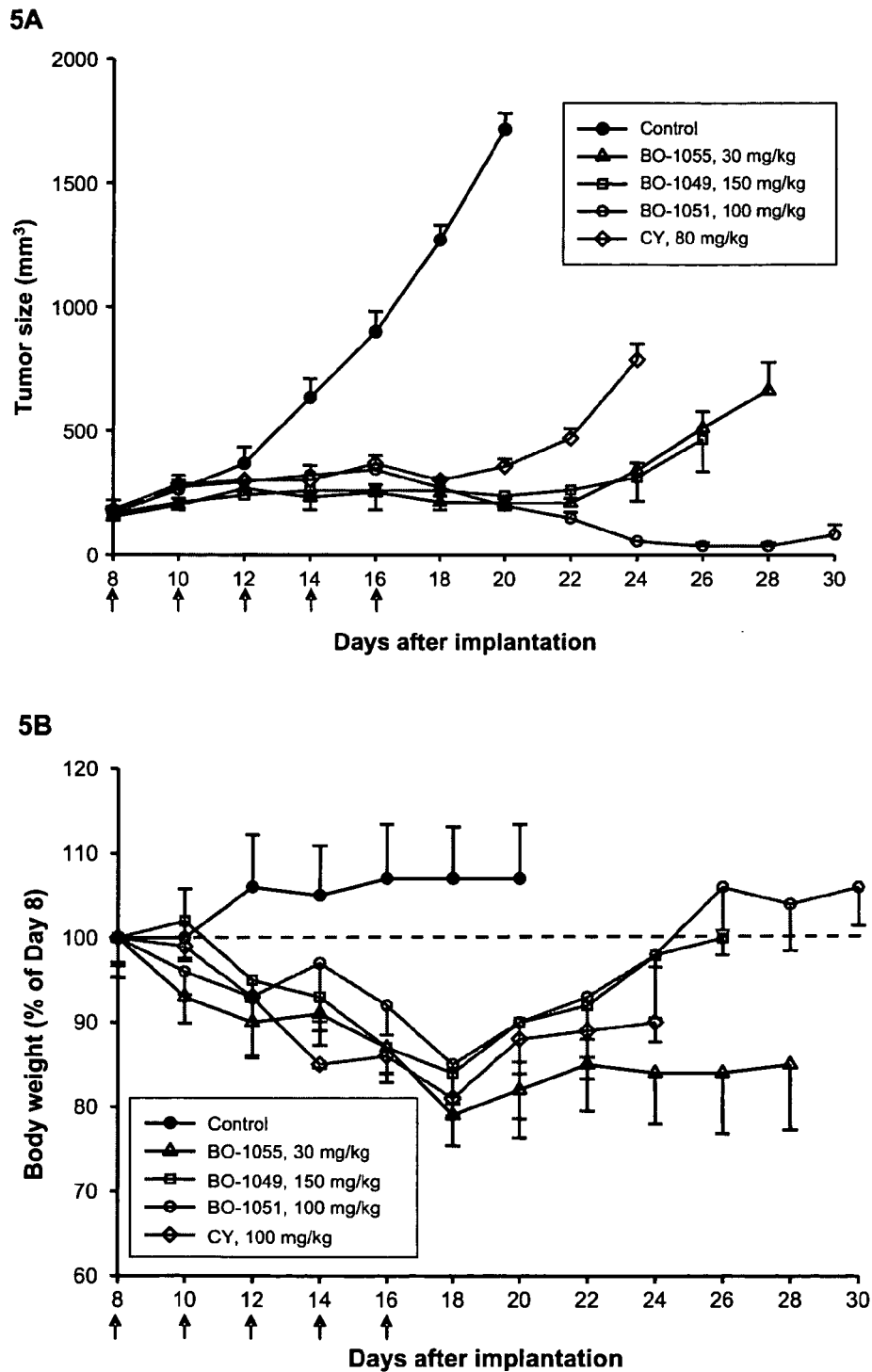
FIG. 5 illustrates therapeutic effects of BO-1049, 1051, 1055 and Cyclophosphamide in nude mice bearing human glioma U87 MG xenograft (iv. inj., Q2D×5, n=3), tumor size changes (FIG. 5A) and body weight changes (FIG. 5B).

Athymic nude mice bearing the nu/nu gene were used for human breast tumor MX-1 xenograft (FIGS. 3 and 4) and human brain glioma U87 GM xenograft (FIG. 5). Nude mice were obtained from National Cancer Institute, Frederick, Md. Male mice 6 weeks old or older weighing 22 g or more were used for experiments with subcutaneous tumor inoculation as described previously.[62] Drug was administered via the tail vein by iv injection. Tumor volumes were assessed by measuring length×width×height (or width) by using caliper. Vehicle used was 20 μL DMSO in 180 μL saline. All animal studies were conducted in accordance with the guidelines of the U.S. National Institutes of Health Guide for the Care and Use of Animals and the protocol approved by the Institutional Animal Care and Use Committee.

Table 2 shows the in vivo antitumor therapeutic effect of representative compounds. Nude mice bearing human tumor were treated with these agents at the dose of 30-150 mg/kg, every other two days (Q2D), five times (for BO-1038-BO1055) or daily (QD) 3 to 5 times (for BO-1062-BO-1079) via intravenous injection, resulted in tumor total disappearance (or complete remission, CR) with low toxicity. These results demonstrated the newly invented compounds possess potent antitumor therapeutic efficacy and have potential for clinical applications.

Figure 3:
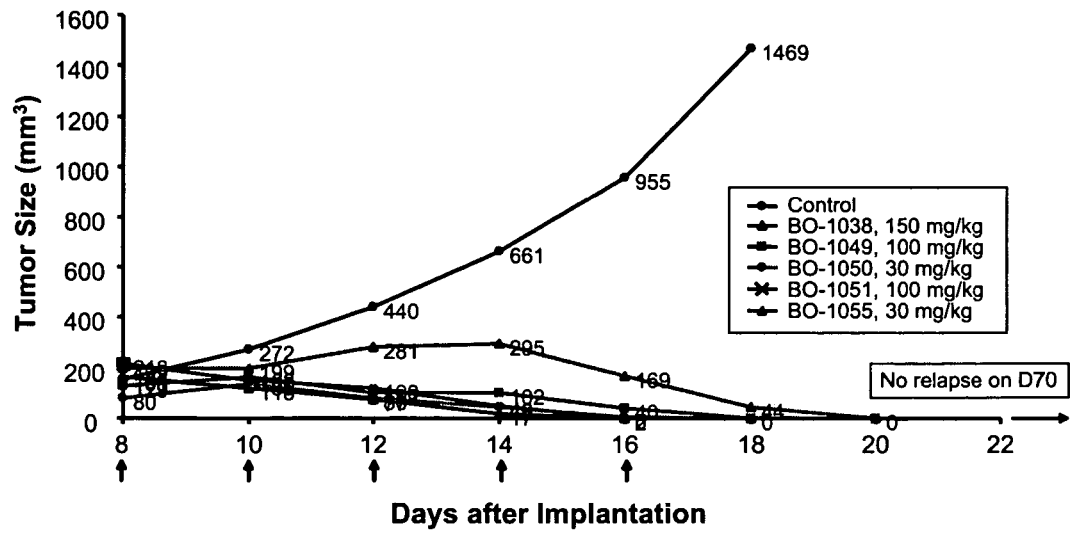
FIG. 3 illustrates therapeutic effect of BO-1038, 1049, 1050, 1051 and 1055 in nude mice bearing MX-1 xenograft, (i.v. inj, Q2D×5, n=3), average tumor size changes (FIG. 3A) and average body weight changes (FIG. 3B).
Figure 3:
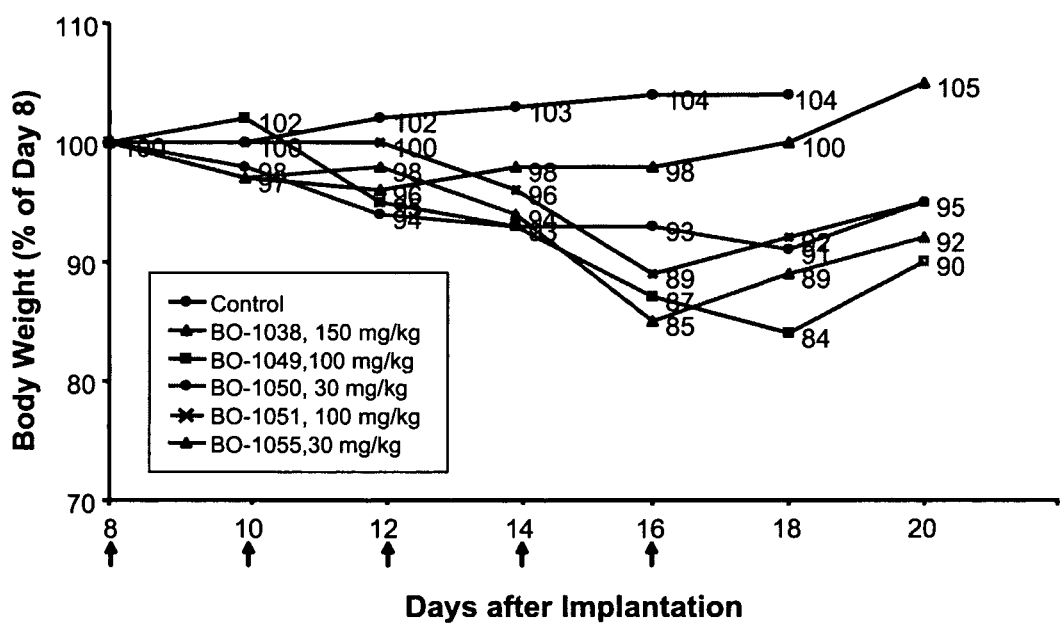
Figure 4:
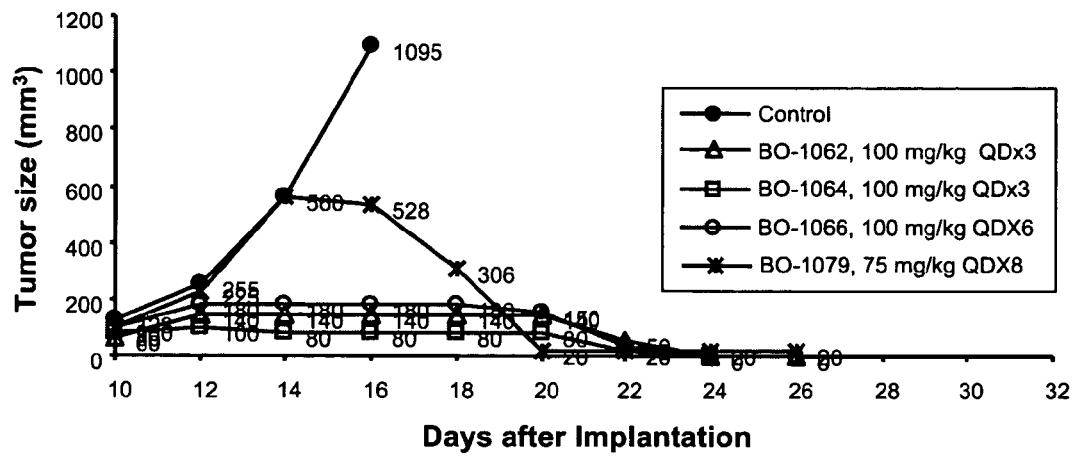
FIG. 4 illustrates therapeutic effect of BO-1062, 1064, 1066 and 1079 in nude mice bearing MX-1 (i.v. inj, n=1), tumor size changes (FIG. 4A) and body weight changes (FIG. 4B).
Figure 4:
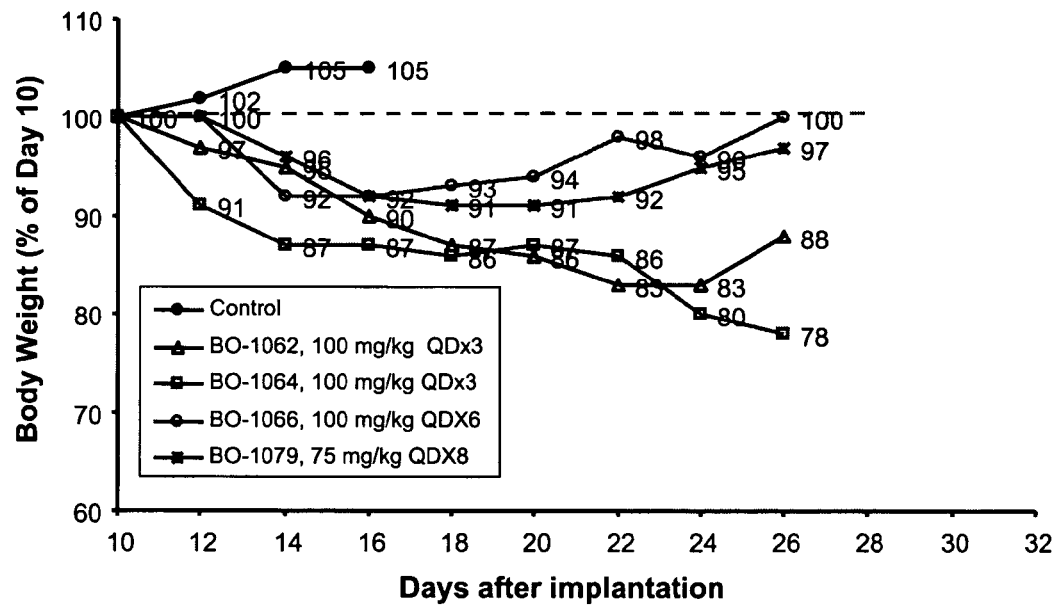

Examples of therapeutic effects for the representative N-mustard compounds against human breast carcinoma MX-1 xenograft in nude mice are summarized in Table 2. Under the experimental conditions as indicated, BO-1051, 1053, 1038, 1049, 1055 (FIGS. 3, A and B) and 1062, 1064 and 1066 (FIGS. 4, A and B) achieved complete tumor remission, whereas BO-1037 and 1050 (FIGS. 3, A and B) achieved CR in parts of the mice. Remarkably, BO-1038, 1049, 1050, 1051 and 1055, with only one cycle 5-dose-treatments, complete remission was achieved and maintained for over 70 days without any replase in 3 out of 3 mice (FIG. 3A). Based on Eq.4, the log cell kill (LSK) is estimated to be >4.1.

TABLE 2

Antitumor therapeutic effects of newly synthesized N-mustard compound against human mammary carcinoma MX-1 xenograft in nude mice[1]

| Compound | Dose (mg/kg) | Schedule | Therapeutic effect | Maximal body-weight loss (%) | Remark |
|---|---|---|---|---|---|
| 15 BO-1037 | 50-90 | Q2D × 8 Q2D × 2 | 2/3 CR on D23, 25 2/3 relapsed on D40, 40 | 12 | |
| 16 BO-1050 | 30 | Q2D × 5 | 2/2 CR on D16, 18 No relapse on D26 | 9 | See FIG. 3A, B |

TABLE 2-continued

Antitumor therapeutic effects of newly synthesized N-mustard compound against human mammary carcinoma MX-1 xenograft in nude mice[1]

| Compound | Dose (mg/kg) | Schedule | Therapeutic effect | Maximal body-weight loss (%) | Remark |
|---|---|---|---|---|---|
| 17 BO-1051[2] | 100 | Q2D × 5 | 3/3 CR on D16, 16, 18 No relapse on D70 | 11 | See FIG. 3A, B |
| 18 BO-1079 | 75 | QD × 8 | 1/1, >99% tumor growth suppression | 9 | See FIG. 4A, B |
| 19 BO-1053 | 70 | Q2D × 5 | NA | NA | Too high dose |
| 21 BO-1038 | 150 | Q2D × 5 | 3/3 CR on D16, 16, 16 No relapse on D70 | 4 | See FIG. 3A, B |
| 22 BO-1049[2] | 100 | Q2D × 5 | 3/3 CR on D18, 18, 18 No relapse on D70 | 16 | See FIG. 3A, B |
| 23 BO-1055[2] | 30 | Q2D × 5 | 3/3 CR on D20, 20, 20 No relapse on D70 | 15 | See FIG. 3A, B |
| 24 BO-1062 | 100 | Q2D × 5 | 1/1 CR on D22 | 17 | See FIG. 4A, B |
| 25 BO-1063 | 100 | QD × 3 | NA | NA | Too high dose |
| 26 BO-1064 | 100 | QD × 3 | 1/1 CR on D22 | Died of Toxicity D28 | See FIG. 4A, B |
| 27 BO-1066 | 100 | QD × 3 | 1/1 CR on D22 | 13 | See FIG. 4A, B |
| 29 BO-1065 | 100 | QD × 3 | NA | NA | Too high dose |

[1]Treatment started on Day 8 after tumor implantation. All treatments were carried out via i.v. injection. CR is referred as complete tumor remission.
[2]For therapeutic effect against human U87 GM glioma s.c. xenograft in nude mice, see FIG. 5A and 5B.

The therapeutic effects of N-mustard compounds, BO-1049, 1051 and 1055, against human glioma U87 GM s.c. xenograft in nude mice were given in FIG. 5, A and B. U87 glioma is known to be refractory tumor that can not be effectively treated with cell-cycle specific anti-tumor drugs such as taxol, epothilones, or arabinosylcytosine. However, cell-cycle non-specific drugs such as alkylating agent, cyclophosphamide or BCNU, yields better therapeutic results. As shown in FIG. 5, BO-1049 (150 mg/kg), BO-1051 (100 mg/kg), and BO-1055 (30 mg/kg), Q2D×5, i.v.-injection, resulted in complete tumor-growth suppression. However, upon 6 days of recession of treatment with BO-1049 or BO-1055, the tumor began to regrow. Remarkably, those mice with BO-1051 (100 mg/kg, Q2D×5, n=3), it not only completely suppressed tumor growth but also continued to shrink tumor to only 18% of original tumor size (i.e., nearly complete remission) with only one cycle of treatment. Furthermore, this tumor shrinkage effect was observed on 10 and 12 days after the last dose of BO-1051 on Day 16 (The treatment started on Day 8). Interestingly, all three compounds (BO-1049, 1051 and 1055) yielded superior therapeutic effects than cyclophosphamide (80 mg/kg, Q2D×5) in a parallel study.

Biological Methods

Tumor and Cell Lines. Human colon carcinoma HCT-116 cells and human glioma U87GM cells were obtained from American Type Culture Collection (ATCC, Rockville, Md.). Human mammary carcinoma (MX-1) tumor cells were obtained from MSKCC cell bank. The CCRF-CEM human lymphoblastic leukemia cells and their vinblastine resistant subline (CCRF-CEM/VBL, 680-fold resistance in vitro) were obtained from Dr. William Beck of the University of Illinois, Chicago, and CCRF-CEM/Taxol (330-fold resistance in vitro). Resistant cells CCRF-CEM/taxol were produced by exposing the parent cells to increasing sublethal concentration ($IC_{50}$-$IC_{90}$) of paclitaxel for six months.

Cytotoxicity Assays. In preparation for in vitro cytotoxicity assays, cells were cultured at an initial density 2-5×10$^4$ cells per milliliter. They were maintained in a 5% $CO_2$-humidified atmosphere at 37° C. in RPMI medium 1640 (GIBCO/BRL) containing penicillin (100 units/mL), streptomycin (100 μg/mL, GIBCO/BRL), and 5% heat-inactivated FBS. For cells grown in suspension (such as CCRF-CEM and its sublines), cytotoxicity was measured, by using XTT microculture method[57] in 96-well microtiter plates. For solid tumor cells growing in a monolayer (such as MX-1 and HCT-116), cytotoxicity of the drug was determined, in duplicate, in 96-well microtiter plates by using the sulforhodamine B method.[58] For both methods, the absorbance of each well was measured with a microplate reader (Power Wave XS, Bio-Tek, Winooski, Vt.) after 72-hr incubation as described previously.[59] Dose-effect relationship data from 6 to 7 concentrations of each drug, in duplicate, were analyzed by using a computer program[60] based on the median-effect principle and plot.[61,62]

Animals. Athymic nude mice bearing the nu/nu gene were obtained from NCI, Frederick, Md. and used for all human tumor xenografts. Male nude mice 6 weeks or older weighing 20-24 g or more were used. Compounds were administered via the tail vein for i.v. injection or infusion as described previously.[59] A typical formulation for chemotherapeutic studies for each drug was dissolved in DSMO to make a 25 mg/ml fresh solution, 0.4 ml of this solution was mixed with 0.3 ml of Tween 80, plus 1.3 ml to make 2 ml of 5 mg/ml solution. Bolus injection volume was 0.1-0.2 ml per mouse. Tumor volume was assessed by measuring length×width×height (or width) by using a caliper. For tumor-bearing nude mice during the course of the experiment, the body weight refers to total weight minus the weight of the tumor. All animal studies were conducted in accordance with the guidelines for the National Institute of Health Guide for the Care and Use of Animals and the protocol approved by the Institutional Animal Care and Use Committee.

Definition and Quantitative Determination of Therapeutic Effects in Nude Mice.

The therapeutic effects of a drug against human tumor xenografts in nude mice, under the optimal therapeutic conditions but without any lethality due to drug toxicity, the following degrees of therapeutic effects are defined and calculated by the following formula:

$$\text{Tumor suppression (\%)} = \left\{1 - \left[\frac{(T_c - T_0) - \left[\frac{(T_x - T_0)}{(T_c - T_0)}\right]}{}\right]\right\} \times 100, \quad \text{(Eq. 1)}$$

where $T_0$ is the initial tumor size (in mm³) at beginning of drug treatment;

$T_c$ is tumor size of untreated control group on a given date; and $T_x$ is tumor size of the drug treated group on a given date.

$$\text{Tumor shrinkage (\%)}: \left\{1 - \left[\frac{(T_0 - T_x)}{(T_0)}\right]\right\} \times 100, \quad \text{(Eq. 2)}$$

Where $T_0$ and $T_x$ are as specified as above.

Tumor disappearance (complete remission or CR) is defined by the effect where $[T_x=0]$ for a period of time (in days) for a proportion of animals ($N_{CR}/N$), where N is the total number of animals in the group, and $N_{CR}$ is the number of mice in the group that achieved CR.

Tumor relapse is quantitatively calculated by

[The Day tumor relapsed($D_{relp}$)–The Day CR achieved($D_{CR}$)] (Eq. 3)

for a proportion of animals ($N_{relp}/N$) where N is the total number of animals in the group, and $N_{relp}$ is the number of the mice in the group that relapsed.

The log cell kill (LCK) of the tumor tissue after a given chemotherapy that reached CR is estimated by:

$LCK = \log[2^{(\text{Tumor remission in days}/\text{Tumor doubling time in days})}]$ (Eq. 4)

We have designed and synthesized a series of aniline and phenol N-mustard linked to DNA-affinic carriers (such as 9-anilinoacridines, acridines and quinolines), aminobenzamides or aminophenol ethers with a urea or carbamic acid ester linkage. The linkers located at the para-position of the N-mustard residue are able deactivate the reactivity of the DNA cross-linking pharmacophore. These agents are more stable than alkyl N-mustard derivatives. For example, the half-life ($t_{1/2}$) for BO-1051 was about 45 days in intravenous injection vehicle (DMSO/Tween 80/Saline) and has long half-life in rat plasma with $t_{1/2}$=54 h. The antitumor studies of the newly invented N-mustards demonstrated that these agents possess potent antitumor therapeutic efficacy and have potential for clinical applications.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The content of each of the references disclosed in the present application is entirely incorporated herein by reference.

REFERENCES

1. Hansson, J.; Lewensohn, R.; Ringborg, U.; Nilsson, B. Formation and removal of DNA cross-links induced by melphalan and nitrogen mustard in relation to drug-induced cytotoxicity in human melanoma cells. *Cancer Res.* 1987, 47, 2631-2637.
2. Suzukake, K.; Vistica, B. P.; Vistica, D. T. Dechlorination of L-phenylalanine mustard by sensitive and resistant tumor cells and its relationship to intracellular glutathione content. *Biochem. Pharmacol.* 1983, 32,165-167.
3. Kaldor, J. M.; Day, N. E.; Hemminki, K. Quantifying the carcinogenicity of antineoplastic drugs. *Eur. J. Cancer Clin. Oncol.* 1988, 24, 703-711.
4. Creech, H. J.; Preston, R. K.; Peck, R. M.; O'Connell, A. P. Antitumor and mutagenic properties of a variety of heterocyclic nitrogen and sulfur mustards. *J. Med. Chem.* 1972, 15, 739-746.
5. Kohn, K. W.; Orr, A.; O'Connor, P. M. Synthesis and DNA-sequence selectivity of a series of mono- and difunctional 9-aminoacridine nitrogen mustards. *J. Med. Chem.* 1994, 37, 67-72.
6. Gourdie, T. A.; Valu, K. K.; Gravatt, G. L.; Boritzki, T. J.; Baguley, B. C.; Wakelin, L. P. G.; Wilson, W. R.; Woodgate P. D.; Denny, W. A. DNA-directed alkylating agents. 1. Structure-activity relationships for acridine-linked aniline mustards: consequences of varying the reactivity of the mustard. *J. Med. Chem.* 1990, 33, 1177-1186.
7. Valu, K. K.; Gourdie, T. A.; Gravatt, G. L.; Boritzki, T. J.; Woodgate, P. D.; Baguley, B. C.; Denny, W. A. DNA-Directed Alkylating Agents. 3. Structure-activity relationships for acridine-linked aniline mustards: consequences of varying the length of the linker chain. *J. Med. Chem.* 1990, 33, 3014-3019.
8. Gravatt, G. L.; Baguley, B. C.; Wilson, W. R.; Denny, W. A. DNA-directed alkylating agents. 4. 4-Anilinoquinoline-based minor groove directed aniline mustards. *J. Med. Chem.* 1991, 34, 1552-1560.
9. McClean, S.; Costelloe, C.; Denny, W. A.; Searcey, M.; Wakelin, L. P. G. Sequence selectivity, cross-linking efficacy and cytotoxicity of DNA-targeted 4-anilinoquinoline aniline mustards. *Anti-Cancer Drug Design,* 1999, 14, 187-204.
10. Fan, J.-Y.; Valu, K. K.; Woodgate, P. D.; Baguley, B. C.; Denny, W. A. Aniline mustard analogues of the DNA-intercalating agent amsacrine: DNA intercalation and biological activity. *Anti-Cancer Drug Design,* 1997, 12, 181-203.
11. Koyama, M.; Takahashi, K.; Chou, T.-C.; Darzynkiewicz, Z.; Kapuscinnski, J.; Kelly, T. R.; Watanabe, K. Y. Intercalating agents with covalent bond forming capability. A novel type of potential anticancer agents. 2. Derivatives of chrysophanol and emodin. *J. Med. Chem.* 1989, 32, 1594-1599.
12. Köhler, B.; Su, T.-L.; Chou, T.-C.; Jiang, X.-J.; Watanabe, K. A. Synthesis of cyclopentanthraquinones: analogues of mitomycin C. *J. Org. Chem.* 1993, 58, 1680-1686.
13. Wyatt, M. D.; Garbiras, B. J.; Haskell, M. K.; Lee, M.; Souhami, R. L.; Hartley, J. A. Structure-activity relationship of a series of nitrogen mustard- and pyrrole-containing minor groove binding agents related to distamycin. *Anti-Cancer Drug Designs,* 1994, 9, 511-525.
14. Wyatt, M. D.; Lee, M.; Hartley, J. A. Alkylation specificity for a series of distamycin analogues that tether chloambucil. *Anti-Cancer Drug Design,* 1997, 12, 49-60.
15. Bacherikov, V. A.; Chou, T.-C.; Dong, H.-J.; Chen, C.-H.; Lin, Y.-W.; Tsai, T.-J.; Su, T.-L. Potent antitumor N-mustard derivatives of 9-anilinoacridine, synthesis and antitumor evaluation. *Bioorg. Med. Chem. Lett.* 2004, 14, 4719-4722.

16. Bacherikov, V. A.; Chou, T.-C.; Dong, H.-J.; Zhang, X.; Chen, C.-H.; Lin, Y.-W.; Tsai, T.-J.; Lee, R.-Z.; Liu, L. F.; Su, T.-L. Potent antitumor 9-anilinoacridines bearing an alkylating N-mustard residue on the anilino ring: synthesis and biological activity. *Bioorg. Med. Chem.* 2005, 13, 3993-4006.
17. Su, T.-L.; Lin, Y.-W.; Chou, T.-C.; Zhang, X.; Bacherikov, V. A.; Chen, C.-H.; Liu, L. F.; Tsai, T.-J. Potent antitumor 9-anilinoacridines and acridines bearing an alkylating N-mustard residue on the acridine chromophore: Synthesis and biological activity. *J. Med. Chem.* 2006, 49, 3710-3718.
18. Su, T.-L.; Chou, T.-C.; Kim, J. Y.; Huang, J.-T.; Ciszewska, G.; Ren, W.-Y.; Otter, G. M.; Sirotnak, F. M.; Watanabe, K. A. 9-Substituted acridine derivatives with long half-life and potent antitumor activity: synthesis and structure-activity relationships. *J. Med. Chem.* 1995, 38, 3226-3235.
19. Su, T.-L. Development of DNA topoisomerase II-mediated anticancer agents, 3-(9-acridinylamino)-5-hydroxymethylaniline (AHMAs) and related compounds. *Current Med. Chem.* 2002, 9, 1677-1688.
20. Friedlos, F.; Denny, W. A.; Palmer, B. D.; Springer, C. J. Mustard Prodrugs for Activation by *Escherichia coli* Nitroreductase in Gene-Directed Enzyme Prodrug Therapy. *J. Med. Chem* 1997, 40, 1270-1275.
21. Helsby, N. A.; Atwell, G. J.; Yang, S.; Palmer, B. D.; Anderson, R. F.; Pullen, S. M.; Ferry, D. M.; Hogg, A.; Wilson, W. R.; Denny, W. A. Aziridinyldinitro-benzamides: Synthesis and Structure-Activity Relationships for Activation by *E. coli* Nitroreductase. *J. Med. Chem.* 2004, 47, 3295-307.
22. Caroline J. Springer, Robert Dowell, Philip J. Burke, Elma Hadley, D. Huw Davies, David C. Blakey, Roger G. Melton, and Ion Niculescu-Duvaz Optimization of Alkylating Agent Prodrugs Derived from Phenol and Aniline Mustards: A New Clinical Candidate Prodrug (ZD2767) for Antibody-Directed Enzyme Prodrug Therapy. *J Med Chem.* 1995, 38, 5051-5065.
23. Niculescu-Duvaz, I.; Cooper, R. G.; Stribbling, S. M.; Heyes, J. A.; Metcalfe, J. A.; Springer, C. J. Recent developments in gene-directed enzyme prodrug therapy (GDEPT) for cancer. *Curr Opin Mol Ther.* 1999, 1, 480-486.
24. Masterson, L. A.; Spanswick, V. J.; Hartley, J. A.; Begent, R. H.; Howard, P. W.; Thurston, D. E. Synthesis and biological evaluation of novel pyrrolo[2,1-c][1,4]-benzodiazepine prodrugs for use in antibody-directed enzyme prodrug therapy. *Bioorg. Med. Chem. Lett.* 2006, 16, 252-256.
25. Davies L. C.; Friedlos, F.; Hedley, D.; Martin, J,; Ogilvie, L. M.; Scanlon, I J.; Springer, C. J. Novel fluorinated prodrugs for activation by carboxypeptidase G2 showing good in vivo antitumor activity in gene-directed enzyme prodrug therapy. *J. Med. Chem.* 2005, 48, 5321-5328.
26. Schepelmann, S.; Hallenbeck, P.; Ogilvie, L. M.; Hedley, D.; Friedlos, F.; Martin, J.; Scanlon, I.; Hay, C.; Hawkins, L. K.; Marais, R.; Springer, C. J. Systemic gene-directed enzyme prodrug therapy of hepatocellular carcinoma using a targeted adenovirus armed with carboxypeptidase G2. *Cancer Res.* 2005, 65, 5003-5008.
27. Niculescu-Duvaz, I.; Scanlon, I.; Niculescu-Duvaz, D.; Friedlos, F.; Martin, J.; Marais, R.; Springer, C. J. Significant differences in biological parameters between prodrugs cleavable by carboxypeptidase G2 that generate 3,5-difluoro-phenol and -aniline nitrogen mustards in gene-directed enzyme prodrug therapy systems. *J Med Chem.* 2004, 47, 2651-2658.
28. Mayer, A.; Sharma, S. K.; Tolner, B.; Minton, N. P.; Purdy, D.; Amlot, P.; Tharakan, G.; Begent, R. H.; Chester, K. A. Modifying an immunogenic epitope on a therapeutic protein: a step towards an improved system for antibody-directed enzyme prodrug therapy (ADEPT). *Br J Cancer.* 2004, 90, 2402-2410.
29. Niculescu-Duvaz, D.; Niculescu-Duvaz, I.; Friedlos, F.; Martin, J.; Lehouritis, P.; Marais, R.; Springer, C. J. Self-immolative nitrogen mustards prodrugs cleavable by carboxypeptidase G2 (CPG2) showing large cytotoxicity differentials in GDEPT. *J Med Chem.* 2003, 46, 1690-1705.
30. Cowen, R. L.; Williams, J. C.; Emery, S.; Blakey, D.; Darling, J. L.; Lowenstein, P. R.; Castro, M. G. Adenovirus vector-mediated delivery of the prodrug-converting enzyme carboxypeptidase G2 in a secreted or GPI-anchored form: High-level expression of this active conditional cytotoxic enzyme at the plasma membrane. *Cancer Gene Ther.* 2002, 9, 897-907.
31. Friedlos, F.; Davies, L.; Scanlon, I.; Ogilvie, L. M.; Martin, J.; Stribblin, S. M.; Spooner, R. A.; Niculescu-Duvaz, I.; Marais, R.; Springer C. J. Three new prodrugs for suicide gene therapy using carboxypeptidase G2 elicit bystander efficacy in two xenograft models. *Cancer Res.* 2002, 62, 61724-1729.
32. Francis, R. J.; Sharma, S. K.; Springer, C.; Green, A. J.; Hope-Stone, L. D.; Sena, L.; Martin, J.; Adamson, K. L.; Robbins, A.; Gumbrell, L.; O'Malley, D.; Tsiompanou, E.; Shahbakhti, H.; Webley, S.; Hochhauser, D.; Hilson, A. J.; Blakey, D.; Begent, R. H. A phase I trial of antibody directed enzyme prodrug therapy (ADEPT) in patients with advanced colorectal carcinoma or other CEA producing tumours. *Br J Cancer,* 2002, 87, 600-607.
33. Chang, J.-Y,; Lin, C.-F.; Pan, W.-Y.; Bacherikov, V.; Chou, T.-C.; Chen, C.-H.; Dong, H.; Cheng, S.-Y.; Tsai, T.-J.; Lin, Y.-W.; Chen, K.-T.; Chen, L.-T. Su, T.-L. New analogues of AHMA as potential antitumor agents: Synthesis and biological activity. *Bioorg. Med. Chem.* 2003, 11, 4959-4969.
34. Bacherikov, V. A.; Lin, Y. W.; Chang, J.-Y, Chen; Pan, W.-Y.; Dong, H.; Lee, R.-Z.; Chou, T.-C.; Su, T.-L. Synthesis and Antitumor Activity of 5-(9-Acrydinylamino) anisidine Derivatives. *Bioorg. Med. Chem.* 2005, 13, 6513-6520.
35. Benn, M. H.; Creighton, A. M.; Owen, L. N.; White, G. R. Cytotoxic compounds. Part II. Some amides of the "Nitrogen mustard" type. J. Chem. Soc. 1961, 2365-2375.
36. Baraldi, P. G.; Cacciari, B.; Moro, S.; Romagnoli, R.; Ji, X.-D.; Jacobson, K. A.; Gessi, | S.; Borea, P. A.; Spalluto, G. Fluorosulfonyl- and bis(2-chloroethyl)-aminophenylamino functionalized pyrazolo[4,3-e]1,2,4-triazolo[1,5-c]pyrimidine derivatives: Irreversible antagonists at the human $A_3$ adenosine receptor and molecular modeling studies. *J. Med. Chem.* 2001, 44, 2735-2742.
37. Jordan, A. M.; Khan, T. H.; Osborn, H. M. I.; Photiou, A.; Riley, P. A. Melanocyte-directed enzyme prodrug therapy (MDEPT): development of a targeted treatment for malignant melanoma. *Bioorg. Med. Chem.* 1999, 7, 1775-1780.
38. Palmer, B. D.; Wilson, W. R.; Pullen, S. M.; Denny, W. A. Hypoxia-selective antitumor agents. 3. Relationships between structure and cytotoxicity against cultured tumor cells for substituted N,N-bis(2-chloroethyl)anilines. J. Med. Chem. 1990, 33, 112-121.
39. Jordan, A. M.; Khan, T. H.; Osborn, M. I. Melanocyte-directed enzyme prodrug therapy (MDEPT): development of a targeted treatment for malignant melanoma *Bioorg. Med. Chem.* 1999, 7, 1775-1780.
40. Caroline, J. S.; Robert, D.; Philip, J. B.; Elma, H.; Davies, D. H; David, C. B.; Roger, G. M.; Ion, N. Optimization of Alkylating Agent Prodrugs Derived from Phenol and Aniline Mustards: A New Clinical Candidate Prodrug (ZD2767) for Antibody-Directed Enzyme Prodrug Therapy. *J. Med. Chem.* 1995, 38, 5051-5065.
41. Robert, I. D.; Caroline, J. S.; David, H. D.; Elizabeth, M. H.; Philip, J. B.; Thomas, B. F.; Roger, G. M.; Thomas, A. C.; David, C. B.; Anthony, B. M. New Mustard Prodrugs for Antibody-Directed Enzyme Prodrug Therapy: Alternatives to the Amide Link. *J. Med. Chem.* 1996, 39, 1100-1105.
42. Paull, K. D.; Lin, C.-M.; Hamel, E.; Lee, K.-H. Synthesis and cytotoxicity of 1,6,7,8-substituted 2-(4'-substituted phenyl)-4-quinolones and related compounds: identification as antimitotic agents interacting with tubulin. *J. Med. Chem.* 1993, 36, 1146-1156.
43. Kuo, S.-C.; Lee, H.-Z.; Juang, J.-P.; Lin, Y.-T.' Wu, T.-S.; Chang, J.-J.; Lednicer, D.; Paull, K. D.; Lin, C. M.; Hamel, E.; Lee, K.-H. Synthesis and cytotoxicity of 1,6,7,8-substituted 2-(4-substituted phenyl)-4-quinolones and related compounds: Identification as antimitotic agents interacting with tubulin. *J. Med. Chem.* 1993, 36, 1146-1156.
44. Li, P.; Wang, H.-K.; Kuo, S.-C.; Wu, T.-S.; Mauger, A.; Lin, C. M.; Hamel, E.; Lee, K.-H. Antitumor agents. 155. Synthesis and biological evaluation of 3',6,7-substituted 2-phenyl-4-quinolones as antimicrotubulin agents. *J. Med. Chem.* 1994, 37, 3400-3407.
45. Pellerano, C.; Brizzi, V.; Savini, L. *Atti Accad. Fisiocrit. Siena,* 1971, 3, 253.
46. Thomas, J.; Berkoff, C. E.; Flagg, W. B.; Gallo, J. J.; Haff, R. F., Pinto, C. A., Pellerano, C.; Savini, L. Antiviral quinolinehydrazones. Modified Free-Wilson analysis. *J. Med. Chem.* 1975, 18, 245-250.
47. Gemma, S.; Kukreja, G.; Fattorusso, C.; Persico, M.; Romano, M. P.; Altarelli, M.; Savini, L.; Campiani, G.; Fattorusso, E.; Basilico, N.; Taramelli, D.; Yardleye, V.; and Butinia, S. Synthesis of N1-arylidene-N2-quinolyl- and N2-acrydinylhydrazones as potent antimalarial agents active against CQ-resistant *P. falciparum* strains. *Bioorganic & Medicinal Chemistry Letters,* 16 (2006) 5384-5388.
48. Savini, L.; Chiasserini, L.; Gaeta, A.; and Pellerano, C., Synthesis and anti-tubercular evaluation of 4-quinolylhydrazones, *Bioorganic & Medicinal Chemistry,* 2002, 10, 2193-2198.
49. Kubo, K.; Shimizu, T.; Ohyama, S.; Murooka, H.; Nishitoba, T.; Kato, S.; Kobayashi, Y.; Yagi, M.; Isoe, T.; Nakamura, K.; Osawa, T.; Izawa, T. A Novel Series of 4-Phenoxyquinolines: Potent and Highly Selective Inhibitors of PDGF Receptor Autophosphorylation. *Bioorg. Med. Chem. Lett.* 1997, 23, 2935-2940.
50. Kubo, K.; Ohyama, S.; Shimizu, T.; Takami, A.; Murooka, H.; Nishitoba, T.; Kato, S.; Yagi, M.; Kobayashi, Y.; Iinuma, N.; Isoe, T.; Nakamura, K.; Iijima, H.; Osawa, T.; Izawa, T. Synthesis and Structure-Activity Relationship for New Series of 4-Phenoxyquinoline Derivatives as Specific Inhibitors of Platelet-Derived Growth Factor Receptor Tyrosine Kinase. *Bioorg. Med. Chem.* 2003, 11, 5117-5133.
51. Kubo, K.; Shimizu, T.; Ohyama, S.; Murooka, H.; Iwai, A.; Nakamura, K.; Hasegawa, K.; Kobayashi, Y; Takahashi, N.; Takahashi, K.; Kato, S.; Izawa, T.; Isoe, T. Novel Potent Orally Active Selective VEGFR-2 Tyrosine Kinase Inhibitors: Synthesis, Structure-Activity Relationships, and Antitumor Activities of N-Phenyl-N[1]-{4-(4-quinolyloxy)phenyl}ureas. *J. Med. Chem.* 2005, 48, 1359-1366
52. Su, T.-L.; Chen, C.-H.; Huang, L.-F.; Basu, M. K., Chou, T.-C. Synthesis and structure-activity relationship of potential anticancer agents: Alkylcarbamates of 3-(9-acridinylamino)-5-hydroxymethylaniline. *J. Med. Chem.* 1999, 42, 4741-4748.
53. Acheson, R. M.; Nisbet, D. F. Addition reactions of heterocyclic compounds. Part XLW[1] new azepines from substituted 2-methylquinolines and dialkyl acetylene-dicarboxylates. *J. Chem. Soc. C,* 1971, 3291-3296.
54. Parrick, J.; and Wilcox, R. Convenient routes to pyrrolo [3,2-b]-, pyrrolo[3,2-c]-, and pyrrolo[2,3-c]-quinolines, and a study of the pyrolysis of 2-quinolylhydrazones. *J. Chem. Soc., Perkin Trans.* 1, 1976, 2121-2125.
55. Singh, S. P.; Tarar, L. S.; Vaid, R. K.; Elguero, J.; Martinez, A. Reaction of 4-hydrazinoquinolines with b-diketones. synthesis and spectroscopy ($^{1}H$, $^{13}C$ NMR, MS) of some pyrazolylquinolines. *J. Heterocycl. Chem.* 1989, 26, 733-738.
56. Savini, L.; Massarelli, P.; Pellerano, C.; *Farmaco,* 1993, 48, 515-528.
57. Scudiero, D. A.; Shoemaker, R. H.; Paull, K. D.; Monks, A.; Tierney, S.; Nofziger, T. H.; Currens, M. J.; Seniff, D.; Boyd, M. R. Evaluation of Soluble Tetrazolium/Formazan Assay for Cell Growth and Drug Sensitivity in Culture Using Human and Other Tumor Cell Lines. *Cancer Res.* 1988, 48, 4827-4833.
58. Skehan, P.; Storeng, R. H.; Scudiero, D.; Monks, A.; McMahon, J.; Vistica, D.; Warren, J. T.; Bokesch,; Kenny, S.; Boyd, M. R. New Colorimetric Cytotoxicity Assay for Anticancer-Drug Screening. *J. Natl. Cancer Inst.* 1990, 82, 1107-1112.
59. Chou, T.-C.; O'Connor, O. A.; Tong, W. P.; Guan, Y.-B.; Zhang, X.-G.; Stachel, S. J.; Lee, S.; Danishefsky, S. J. The Synthesis, Discovery and Development of a Highly Promising Class of Microtubule Stabilization Agents: Curative Effects of Desoxyepothilones B and F against Human Tumor Xenografts in Nude *Mice. Proc. Natl. Acad. Sci. USA* 2001, 98, 8113-8118.
60. Chou, T.-C. and Martin, N. CompuSyn for Drug Combinations: PC Software and User's Guide: A Computer Program for Quantitation of Synergism and Antagonism in Drug Combinations, and the Determination of $IC_{50}$ and $ED_{50}$ and $LD_{50}$ Values. ComboSyn, Inc., Paramus, N.J. 2005.
61. Chou, T.-C.; Talalay, P. Quantitative Analysis of Dose-Effect Relationships: the Combined Effects of Multiple Drugs or Enzyme Inhibitors. *Adv. Enzyme Regul.* 1984, 22, 27-55.
62. Chou, T.-C. Theoretical basis, experimental design and computerized simulation of synergism and antagonism in drug combination studies. *Pharmacol. Rev.* 2006, 58, 621-681.

We claim:
1. A compound of the following Formula VIII or salt thereof:

Formula VIII

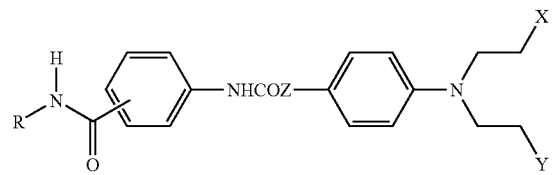

Wherein X and Y are independently selected from the group consisting of Cl, Br, I and $OSO_2Me$.

Z is NH or O;

and wherein R is $(CH_2)_n NR^1R^2$, $(CH_2)_n CH(OH)CH_2OH$, $(CH_2)_n$—N-morpholine, piperidine, 4-piperidinopiperidine, or morpholine;

$R^1$ and $R^2$ are each independently $C_1$-$C_6$ alkyl; and n is 1-5.

2. The compound of claim 1 wherein R is $(CH_2)_n NR^1R^2$, and the compound is a salt formed with an acid.

3. The compound of claim 2 wherein the acid is selected from the group consisting of HCl, HBr, $H_1$, $H_2SO_4$, HCOOH, $CH_3COOH$, citric acid, oxalic acid, and tartaric acid.

4. The compound of claim 1 being 3-(3-{4-[bis-(2-chloroethyl)amino]phenyl}-ureido)-N-(2-dimethylaminoethyl) benzamide hydrochloride (23, BO-1055).

* * * * *